(12) United States Patent
Hong et al.

(10) Patent No.: US 12,178,306 B2
(45) Date of Patent: Dec. 31, 2024

(54) MASK AND SKIN CARE DEVICE INCLUDING SAME

(71) Applicant: LG INNOTEK CO., LTD., Seoul (KR)

(72) Inventors: Beom Sun Hong, Seoul (KR); Hae Rok Son, Seoul (KR); Joon Jae Oh, Seoul (KR); Gyu Lin Lee, Seoul (KR)

(73) Assignee: LG INNOTEK CO., LTD., Seoul (KR)

( * ) Notice: Subject to any disclaimer, the term of this patent is extended or adjusted under 35 U.S.C. 154(b) by 487 days.

(21) Appl. No.: 17/616,264

(22) PCT Filed: May 29, 2020

(86) PCT No.: PCT/KR2020/007032
§ 371 (c)(1),
(2) Date: Dec. 3, 2021

(87) PCT Pub. No.: WO2020/251200
PCT Pub. Date: Dec. 17, 2020

(65) Prior Publication Data
US 2022/0312940 A1    Oct. 6, 2022

(30) Foreign Application Priority Data

Jun. 14, 2019  (KR) .................. 10-2019-0070502
Jun. 14, 2019  (KR) .................. 10-2019-0070592
(Continued)

(51) Int. Cl.
*A45D 44/00*    (2006.01)
*A61N 7/02*    (2006.01)
(Continued)

(52) U.S. Cl.
CPC ............. *A45D 44/002* (2013.01); *A61N 7/02* (2013.01); *B06B 1/0276* (2013.01);
(Continued)

(58) Field of Classification Search
CPC .. A61M 2205/3368; A61M 2205/3375; A61M 2205/0294; A61M 37/0092;
(Continued)

(56) References Cited

U.S. PATENT DOCUMENTS 8,733,153 B2    5/2014   Reimer et al.
9,061,128 B2    6/2015   Hall et al.
(Continued)

FOREIGN PATENT DOCUMENTS

KR    20-0279590    6/2002
KR    20-0421421    7/2006
(Continued)

OTHER PUBLICATIONS

International Search Report dated Sep. 11, 2020 issued in Application No. PCT/KR2020/007032.

*Primary Examiner* — Gerald Johnson
(74) *Attorney, Agent, or Firm* — KED & Associates LLP

(57) ABSTRACT

A mask, according to an embodiment, comprises: a first wiring disposed on a first base layer; a piezoelectric element disposed on the first wiring; a second wiring disposed on the piezoelectric element; a second base layer disposed on the second wiring; a protective layer disposed between the first and second base layers and surrounding the first wire, the second wire, and the piezoelectric element; and a control unit which controls a driving frequency of the piezoelectric element. The control unit controls the driving frequency of the piezoelectric element in a frequency band defined as a first range, and the temperature of the piezoelectric element changes by means of the control of the driving frequency of the control unit.

19 Claims, 40 Drawing Sheets

(30) Foreign Application Priority Data

Jul. 17, 2019 (KR) .................. 10-2019-0086080
Jul. 17, 2019 (KR) .................. 10-2019-0086099
Jul. 26, 2019 (KR) .................. 10-2019-0090955

(51) Int. Cl.
*B06B 1/02* (2006.01)
*B06B 1/06* (2006.01)
*A61N 7/00* (2006.01)

(52) U.S. Cl.
CPC ...... B06B 1/0629 (2013.01); *A45D 2200/155* (2013.01); *A45D 2200/207* (2013.01); *A61N 2007/0034* (2013.01)

(58) Field of Classification Search
CPC ............... A61B 5/0878; A61B 5/6803; A61B 2562/0271; A61B 5/015; A61N 1/403; A61N 7/00; A61N 2007/0034; A61N 1/328; A61N 1/06; A61N 1/28; A61N 1/30

See application file for complete search history.

(56) References Cited

U.S. PATENT DOCUMENTS

| 11,273,274 | B1* | 3/2022 | Schatz | A61M 15/0085 |
| 2010/0198064 | A1 | 8/2010 | Perl et al. | |
| 2013/0236713 | A1 | 9/2013 | Park et al. | |
| 2015/0011889 | A1 | 1/2015 | Lee | |
| 2015/0044442 | A1 | 2/2015 | Huang et al. | |
| 2018/0287045 | A1* | 10/2018 | Tabuchi | H10N 30/878 |
| 2018/0352937 | A1* | 12/2018 | Vandier | A61B 5/6803 |
| 2020/0315576 | A1 | 10/2020 | Kim et al. | |

FOREIGN PATENT DOCUMENTS

| KR | 10-0665328 | 1/2007 |
| KR | 10-0920239 | 10/2009 |
| KR | 10-2010-0031652 | 3/2010 |
| KR | 10-2012-0053621 | 5/2012 |
| KR | 10-2015-0006519 | 1/2015 |
| KR | 10-2015-0020054 | 2/2015 |
| KR | 10-2015-0135335 | 12/2015 |
| KR | 10-2016-0006573 | 1/2016 |
| KR | 10-2016-0052846 | 5/2016 |
| KR | 10-2016-0069399 | 6/2016 |
| KR | 10-1638053 | 7/2016 |
| KR | 10-2017-0126579 | 11/2017 |
| KR | 10-1834596 | 3/2018 |
| KR | 10-1866371 | 7/2018 |

* cited by examiner

FIG. 18
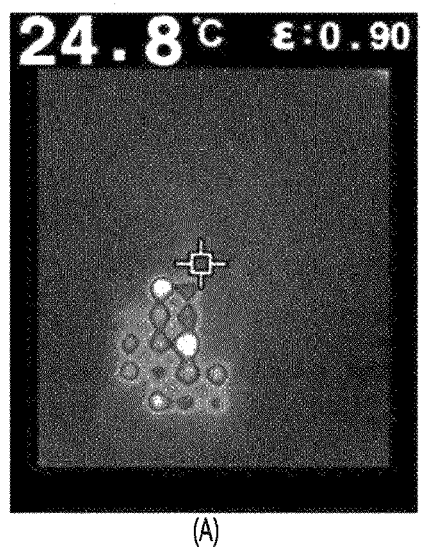
(A)
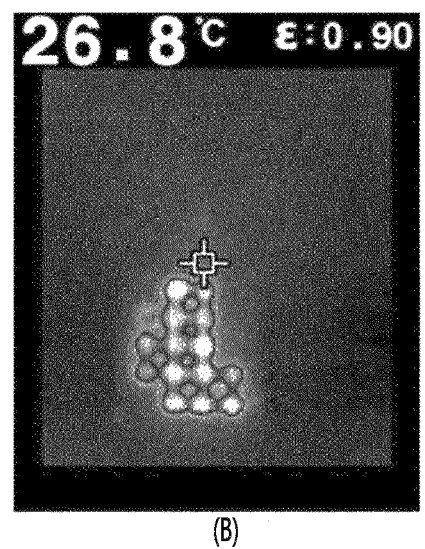
(B)

MASK AND SKIN CARE DEVICE INCLUDING SAME

CROSS-REFERENCE TO RELATED PATENT APPLICATIONS

This application is a U.S. National Stage Application under 35 U.S.C. § 371 of PCT Application No. PCT/KR2020/007032, filed May 29, 2020, which claims priority to Korean Patent Application Nos. 10-2019-0070502, filed Jun. 14, 2019, 10-2019-0070592, filed Jun. 14, 2019, 10-2019-0086080 filed Jul. 17, 2019, 10-2019-0086099, filed Jul. 17, 2019 and 10-2019-0090955, filed Jul. 26, 2019, whose entire disclosures are hereby incorporated by reference.

TECHNICAL FIELD

An embodiment relates to a mask and a skin care device including the same.

BACKGROUND ART

Human skin may be damaged or contaminated depending on external factors such as environmental pollution, ultraviolet rays, stress, and the like, and wrinkles may occur due to internal factors such as aging, hormonal changes, and the like. Recently, as interest in the skin has increased, various devices for skin treatment, beauty, and anti-aging have been developed.

In detail, a device has been developed, which is capable of applying thermal energy to the skin, for example, a device capable of improving skin elasticity by applying infrared energy. In addition, a device using sound waves or light rays has been developed in order to effectively inject cosmetics or drugs into the skin. For example, a device has been developed, which is capable of forming a path through which cosmetics or drugs are injected into the skin using sonophoresis and laserporation. In addition, a device using electric propulsion force has been developed in order to effectively inject cosmetics or drugs into the skin. For example, a device has been developed, which is capable of effectively injecting ionic substances contained in cosmetics or drugs into the skin using iontophoresis, electroporation, and electroosmosis. That is, various devices have been developed, which is capable of caring or treating a user's skin by providing light energy, microcurrent, vibration, or the like to the skin.

In general, the above-described devices may be provided in a form of a patch detachable to the skin, and the devices are attached to a specific skin region to care or treat the skin of the attached region. In addition, the above-described devices are provided in a form of a mask pack disposed to cover the entire user's face to care or treat the facial skin.

However, since the devices are formed to have a predetermined thickness, it may be difficult to effectively adhere to the user's skin.

In addition, the devices are difficult to effectively adhere to the user's skin in curved regions such as both cheeks, nose, and the like. In detail, it may be difficult to effectively adhere to the user's skin due to materials and variable characteristics of the device. Accordingly, the device may be operated in a state in which the device is not completely adhered to the user's skin, and the device may be separated from the user's skin due to the user's movement or vibration of the device during the operation thereof. Accordingly, a care or treatment effect using the device may be insignificant.

In addition, there is a problem that the device is deformed while the device is adhered to the user's skin. Accordingly, there is a problem that transmittance characteristics of ultrasonic waves generated from a piezoelectric element of the device are deteriorated.

In addition, there is a problem that an internal electric wiring is damaged due to the deformation of the device that occurs while the device is adhered to the user's skin. In particular, there is a problem that an electric wiring of the device in a region corresponding to a relatively curved skin is disconnected due to deformation of the device that occurs when the device is worn.

In addition, when the device includes a heating function, a separate heating member may be disposed inside the device. However, there is a problem that the overall thickness of the device increases by the heating member, and there is a problem that the adhesion to the user's skin is deteriorated due to the increase in thickness.

Accordingly, the device has a problem that it is difficult to effectively transmit ultrasonic energy to the user's skin and it is difficult to evenly transmit the ultrasonic energy to the entire skin region.

Therefore, a new mask capable of solving the above-described problem is required.

DISCLOSURE

Technical Problem

An embodiment is to provide a mask and a skin care device that have variability and improved reliability.

In addition, an embodiment is to provide a mask and a skin care device capable of effectively adhering to a user's skin.

In addition, an embodiment is to provide a mask and a skin care device capable of providing uniform ultrasonic energy to a user's skin.

In addition, an embodiment is to provide a mask and a skin care device capable of providing a heating function to a user without including a separate heating member.

In addition, an embodiment is to provide a mask and a skin care device capable of providing a cooling function to a user without including a separate cooling member.

In addition, an embodiment is to provide a mask and skin care device capable of reducing the overall thickness and weight.

In addition, an embodiment is to provide a mask and a skin care device capable of minimizing the loss of ultrasonic energy generated during operation.

Technical Solution

A mask according to an embodiment includes a first wiring disposed on a first base layer, a piezoelectric element disposed on the first wiring, a second wiring disposed on the piezoelectric element, a second base layer disposed on the second wiring, a protective layer disposed between the first and second base layers and surrounding the first wiring, the second wiring, and the piezoelectric element, and a control unit for controlling a driving frequency of the piezoelectric element, wherein the control unit controls the driving frequency of the piezoelectric element in a frequency band defined as a first range, and a temperature of the piezoelectric element is changed by controlling the driving frequency by the control unit.

Advantageous Effects

A mask according to an embodiment may be elastically deformed depending on a shape of a curved skin of a user by a first base layer, a second base layer, or the like. Accordingly, the mask can be effectively adhered to the skin of the user.

In addition, the mask according to the embodiment may include a plurality of piezoelectric elements, and the piezoelectric elements may generate ultrasonic energy in the entire region of the mask. Accordingly, it is possible to provide ultrasonic energy having a uniform intensity to a user wearing the mask.

In addition, the piezoelectric elements according to the embodiment may be disposed at different intervals from each other depending on a face shape of the user. For example, the piezoelectric elements disposed in a relatively curved region such as nose, cheeks, and the like and a planar region such as forehead of the user are disposed at different intervals from each other, and accordingly, it is possible to provide ultrasonic energy having a uniform intensity to the curved region of the user's face.

In addition, the mask according to the embodiment may operate in various modes. For example, the mask may include a cooling mode, a heating mode, and the like, and may provide a cooling effect, a heating effect, and the like to the user's skin. In this case, the mask can provide the above-described effect by controlling a driving frequency of the piezoelectric element without a separate heating member and cooling member. Therefore, the mask according to the embodiment can be provided slimmer.

In addition, the mask according to the embodiment may include a sensing unit that senses a temperature of the mask. In detail, the mask may sense the temperature by the sensing unit and may correct the driving frequency of the mask based on the sensed temperature. Accordingly, the embodiment can control the temperature of the mask and prevent the user from suffering damage such as a low-temperature burn or the like due to the temperature.

DESCRIPTION OF DRAWINGS

FIGS. 18(A) and (B) are data comparing ultrasonic power of a mask according to the second embodiment and Comparative Example.

FIGS. 33(a) to 37 are views for describing a method of manufacturing a mask according to an embodiment.

MODES OF THE INVENTION

Figure 1:
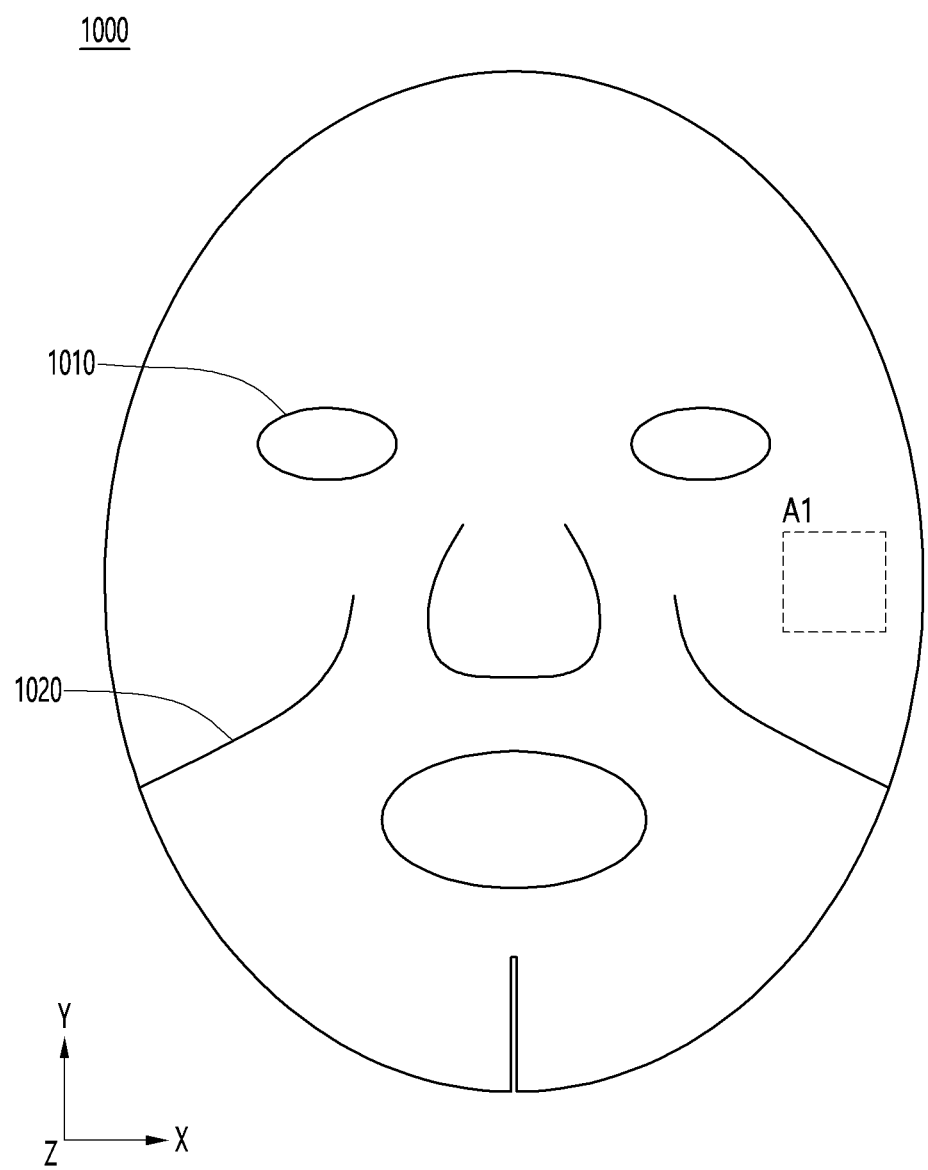
FIG. 1 is a front view of a mask according to an embodiment.
Figure 2:
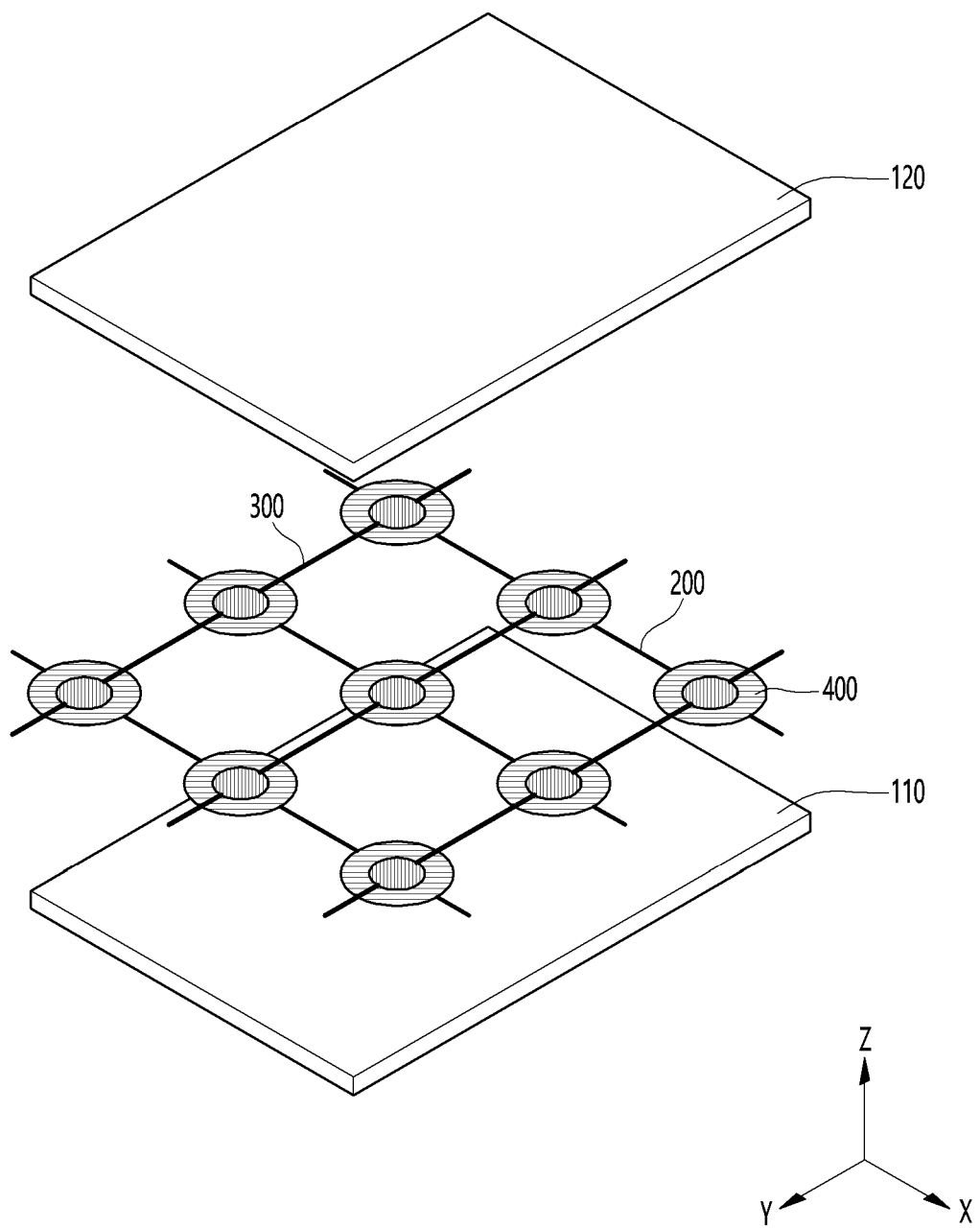
FIG. 2 is an exploded perspective view of region A1 in FIG. 1.

Hereinafter, embodiments of the present invention will be described in detail with reference to the accompanying drawings.

However, the spirit and scope of the present invention is not limited to a part of the embodiments described, and may be implemented in various other forms, and within the spirit and scope of the present invention, one or more of the elements of the embodiments may be selectively combined and replaced.

In addition, unless expressly otherwise defined and described, the terms used in the embodiments of the present invention (including technical and scientific terms may be construed the same meaning as commonly understood by one of ordinary skill in the art to which this invention belongs, and the terms such as those defined in commonly used dictionaries may be interpreted as having a meaning that is consistent with their meaning in the context of the relevant art.

In addition, the terms used in the embodiments of the present invention are for describing the embodiments and are not intended to limit the present invention. In this specification, the singular forms may In addition include the plural forms unless In detail stated in the phrase, and may include at least one of all combinations that may be combined in A, B, and C when described in "at least one (or more) of A (and), B, and C".

In addition, in describing the elements of the embodiments of the present invention, the terms such as first, second, A, B, (A, and (b) may be used. These terms are only used to distinguish the elements from other elements, and the terms are not limited to the essence, order, or order of the elements. Further, when an element is described as being "connected", "coupled", or "connected" to another element, it may include not only when the element is directly "connected" to, "coupled" to, or "connected" to other elements, but also when the element is "connected", "coupled", or "connected" by another element between the element and other elements.

Further, when described as being formed or disposed "on (over)" or "under (below)" of each element, the "on (over)" or "under (below)" may include not only when two elements are directly connected to each other, but also when one or more other elements are formed or disposed between two elements. Furthermore, when expressed as "on (over)" or "under (below)", it may include not only the upper direction but also the lower direction based on one element.

In addition, before describing the embodiments of the present invention, a first direction may refer to an x-axis direction shown in the drawings, and a second direction may be a different direction from the first direction. As an example, the second direction may refer to a y-axis direction shown in the drawing in a direction perpendicular to the first direction. In addition, a horizontal direction may refer to the first and second directions, and a vertical direction may refer to a direction perpendicular to at least one of the first and second directions. For example, the horizontal direction may refer to the x-axis and y-axis directions of the drawing, and the vertical direction may be a z-axis direction of the drawing and a direction perpendicular to the x-axis and y-axis directions.

Referring to FIGS. 1 to 6, a mask 1000 according to an embodiment may have a shape corresponding to a shape of a user's face. The mask 1000 according to the embodiment may be provided in a predetermined size to cover the user's face and have a predetermined elasticity in order to be adhered to the user's face. The mask 1000 may include one surface in contact with a user's skin and the other surface opposite to the one surface, and the one surface of the mask 1000 may be made of a material that is harmless to the human body, so that it is harmless despite being in contact with the user's skin for a long time.

The mask 1000 may include at least one of an opening 1010 and a cutout portion 1020. In detail, the opening 1010 may be formed in a portion corresponding to the user's eyes or mouth. The opening 1010 is a region penetrating through one surface and the other surface of the mask 1000 facing the user's skin, and when the user wears the mask 1000, the user's eyes and mouth may be inserted into the opening 1010, and a region excluding the opening 1010 may be adhered to the user's face.

In addition, the cutout portion 1020 may be formed in a portion corresponding to both cheek lines, chin, and the like, which are relatively curved in order to improve adhesion between the mask 1000 and the skin, but the embodiment is not limited thereto. The cutout portion 1020 may have a form in which one surface and the other surface of the mask 1000 are partially cut.

The mask 1000 may provide ultrasonic waves to the user's skin through a piezoelectric member adhered to the user's skin and included therein. Accordingly, drugs or cosmetics between the mask 1000 and the skin may be effectively provided to the user.

The region excluding the opening 1010 in the mask 1000 according to the embodiment may include a first base layer 110, a first wiring 200, a piezoelectric element 400, a second wiring 300, a second base layer 120, a protective layer 550, and a control unit 1200. In detail, the mask 1000 may include the first wiring 200, the piezoelectric element 400, the second wiring 300, and the second base layer 120 sequentially disposed on the first base layer 110, and may include the protective layer 550 disposed between the first base layer 110 and the second base layer 120.

The first base layer 110 may include a material harmless to the human body. In addition, the first base layer 110 may include a material having softness and elasticity. For example, the first base layer 110 may include at least one material of silicone, a thermoplastic resin, a thermoplastic silicone resin, a thermoplastic elastomer, a polyurethane elastomer, an ethylene vinyl acetate (EVA), a polyvinyl chloride (PVC) in which a harmless plasticizer and a stabilizer are added. Preferably, the first base layer 110 may include a silicone elastomer that is relatively light, may minimize irritation upon contact with the user's skin, and has a predetermined elasticity.

The first base layer 110 may reflect wavelengths emitted from the piezoelectric element 400 to be described later in a direction of one surface of the mask 1000. That is, the first base layer 110 may be a reflective layer.

To this end, a thickness t1 of the first base layer 110 may be equal to or smaller than a thickness t2 of the second base layer 120 to be described later. In detail, the thickness t1 of the first base layer 110 may be equal to or smaller than the thickness t2 of the second base layer 120 in order to reflect the wavelengths emitted from the piezoelectric element 400 toward the first substrate 110 to the first base layer 110. That is, the second base layer 120 may be a base layer facing the user's skin, and the first base layer 110 may be a base layer disposed in a region opposite to the second base layer 120.

The thickness t1 of the first base layer 110 may be about 50 µm to about 10 mm. When the thickness t1 of the first base layer 510 is less than about 50 µm, the thickness t1 of the first base layer 510 is relatively small, so that components disposed on the first base layer 110 may not be effectively protected. In detail, when the mask 1000 is elastically deformed and the first base layer 110 is elastically deformed, the wirings 200 and 300 and the piezoelectric element 400 on the first base layer 110 may not be effectively protected.

In addition, when the thickness t1 of the first base layer 110 exceeds about 10 mm, the thickness of the entire mask 1000 may be increased, and most of the wavelengths emitted from the piezoelectric element 400 toward the first substrate 110 pass through the first base layer 110, so that an amount of reflection in the direction of one surface of the mask 1000 may be small.

In addition, when the thickness t1 of the first base layer 110 exceeds about 10 mm, a required thickness of the second base layer 120 may be increased for reflection in the direction of one surface of the mask 1000, and a region range of the wavelengths generated from the piezoelectric element 400 is high for reflection, and thus it may not be suitable for use in the mask 1000.

In addition, when the thickness t1 of the first base layer 110 exceeds about 10 mm, elastic deformation characteristics of the mask 1000 may be deteriorated. Accordingly, the mask 1000 may not be elastically deformed effectively in a form corresponding to the user's skin.

Therefore, it is preferable that the thickness t1 of the first base layer 110 satisfies the above-described range in order to prevent the above-described problems. More preferably, the thickness t1 of the first base layer 110 may be about 100 μm to about 1000 μm. That is, it is preferable that the first base layer 110 has a thickness range of about 100 μm to about 1000 μm in consideration of reliability, reflective properties, variability, thickness, weight, and ultrasonic impedance characteristics of the mask 1000 to be manufactured.

In addition, the first base layer 110 may have grooves, pores, or the like formed therein in order to effectively reflect the wavelengths generated from the piezoelectric element 400. For example, the grooves and pores may be disposed in a region overlapping the piezoelectric element 400 for effective reflection, but the embodiment is not limited thereto.

The first wiring 200 may be disposed on the first base layer 110. The first wiring 200 may be disposed on one surface of the first base layer 110 facing the piezoelectric element 400. The first wiring 200 may extend in a first direction (x-axis direction) on the first base layer 110. The first wiring 200 may be in direct contact with one surface of the first base layer 110. The first wiring 200 may be formed on one surface of the first base layer 110 by a process such as deposition, printing, bonding, or the like. The first wiring 200 may be electrically connected to the piezoelectric element 400.

The first wiring 200 may include a conductive material. As an example, the first wiring 200 may include at least one metal of aluminum (Al), copper (Cu), silver (Ag), gold (Au), chromium (Cr), nickel (Ni), molybdenum (Mo), titanium (Ti), and alloys thereof. In addition, the first wiring 200 may include a non-metal such as carbon, and the like, and may include a conductive elastic body.

The first wiring 200 may have a single layer or a multiple layer structure. As an example, the first wiring 200 may have a single layer structure including one selected from the above-described materials. In addition, the first wiring 200 may have a multiple layer structure including a metal material selected from the above-described materials and the conductive elastic body.

The first wiring 200 may include a plurality of first sub-wirings 201 disposed on the first base layer 110. Each of the plurality of first sub-wirings 201 may extend in a first direction and may be disposed to be spaced apart from each other in a second direction different from the first direction. The plurality of first sub-wirings 201 may be electrically connected to each other. Here, the second direction may be a direction different from the first direction and a direction perpendicular to the first direction, but the embodiment is not limited thereto.

A thickness of the first sub-wiring 201 may be about 2 μm to about 50 μm. In detail, the thickness of the first sub-wiring 201 may be about 2 μm to about 40 μm. When the thickness of the first sub-wiring 201 is less than about 2 μm, electrical characteristics may be deteriorated, and it may be difficult to form uniformly. In addition, when the thickness of the first sub-wiring 201 exceeds about 50 μm, the overall thickness of the mask 1000 may be increased, and a manufacturing time of the first wiring 210 may be increased. In addition, the thickness of the first sub-wiring 201 is too thick, and thus stretchable characteristics may be deteriorated. Preferably, the thickness of the first sub-wiring 201 may be about 5 μm to about 35 μm or less in consideration of stretchable characteristics in the horizontal direction, reliability, and process efficiency.

In addition, a line width of the first sub-wiring 201 may be about 50 μm to about 500 μm. In detail, the line width of the first sub-wiring 201 may be about 100 μm to about 450 μm. The line width of the first sub-wiring 201 may be greater than the thickness of the first sub-wiring 201. When the line width of the first sub-wiring 201 is less than about 50 μm, the reliability may be deteriorated, and when the line width of the first sub-wiring 201 exceeds about 500 μm, an elongation may be decreased and the stretchable characteristics may be deteriorated. Preferably, the line width of the first sub-wiring 201 may be about 100 μm to about 400 μm in consideration of the stretchable characteristics.

The first wiring 200 may include a first connection portion 210 and a first extension portion 220. For example, one of the first sub-wirings 201 may include the first connection portion 210 and the first extension portion 220 connected to the first connection portion 210.

The first connection portion 210 may be disposed in a region corresponding to a lower surface of the piezoelectric element 400. In detail, the first connection portion 210 may be disposed in a region overlapping the lower surface of the piezoelectric element 400 in the vertical direction. The first connection portion 210 may face the lower surface of the piezoelectric element 400. The first connection portion 210 may be provided in a number corresponding to the piezoelectric element 400.

The first connection portion 210 may have a shape corresponding to the lower surface of the piezoelectric element 400. The first connection portion 210 may have a width corresponding to the lower surface of the piezoelectric element 400. As an example, a width of the first connection portion 210 in the horizontal direction may be equal to or smaller than a width of the lower surface of the piezoelectric element 400 in the horizontal direction. In detail, the width of the first connection portion 210 in the horizontal direction may be about 50% to about 100% of the width of the lower surface of the piezoelectric element 400 in the horizontal direction. When the width of the first connection portion 210 in the horizontal direction is less than about 50%, electrical characteristics between the first wiring 200 and the piezoelectric element 400 may be deteriorated. In addition, when the width of the first connection portion 210 in the horizontal direction is greater than the width of the lower surface of the piezoelectric element 400, the transmittance of ultrasonic energy may be deteriorated. Therefore, it is preferable that the width of the first connection portion 210 in the horizontal direction satisfies the above-described range.

The first extension portion 220 may extend in the first direction from the first connection portion 210. The first extension portion 220 may be disposed between a plurality of first connection portions 210. In detail, the first extension portion 220 may be disposed between the first connection portions 210 spaced apart in the first direction. That is, the first extension portion 220 may connect between adjacent first connection portions 210.

Figure 3:
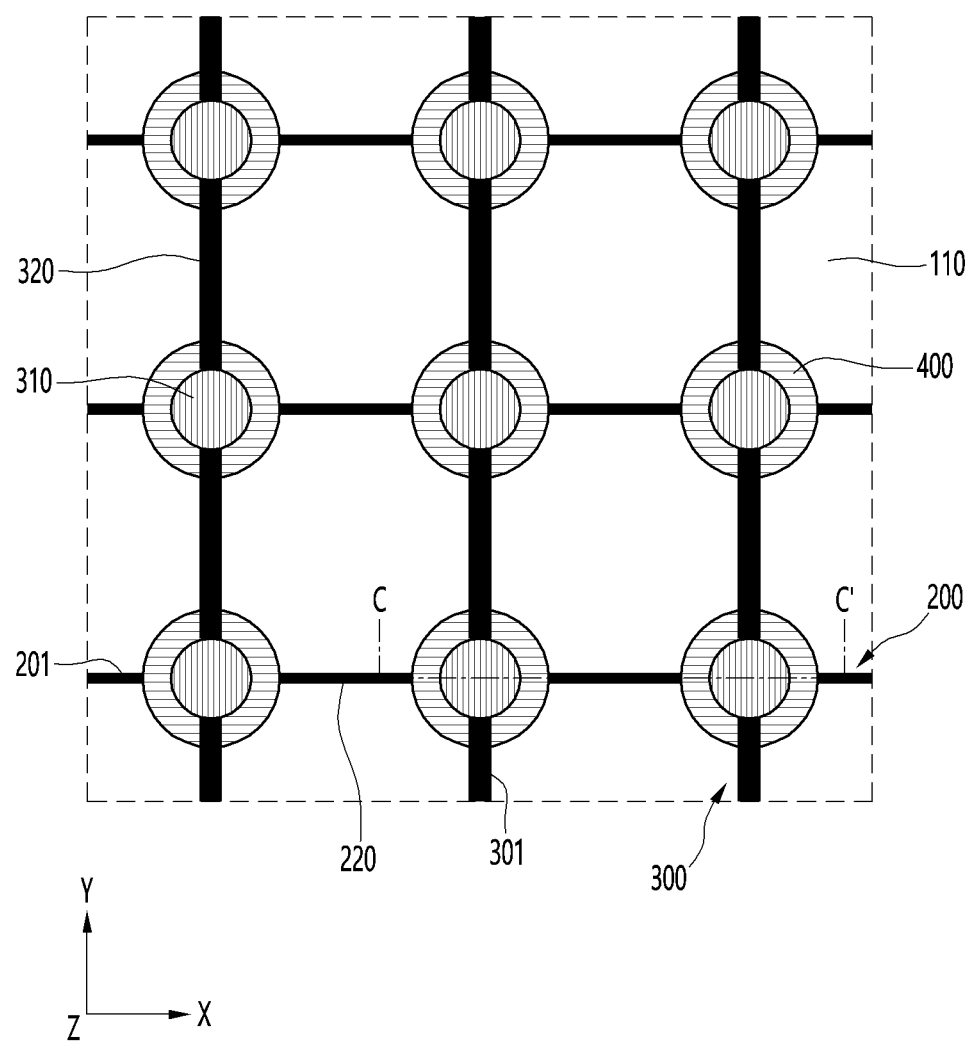
FIG. 3 is a top view of the region A1 in FIG. 1.

The first wiring 200 may have various shapes. For example, when viewed in a plane, each of the plurality of first sub-wirings 201 may extend in the first direction in a linear shape as shown in FIG. 3. In detail, the plurality of first sub-wirings 201 may be spaced apart from the adjacent first sub-wirings 201 in the second direction at equivalent intervals and may extend in the first direction in the linear shape. That is, the first extension portion 220 of the first wiring 200 may have the linear shape extending in the first direction.

Figure 4:
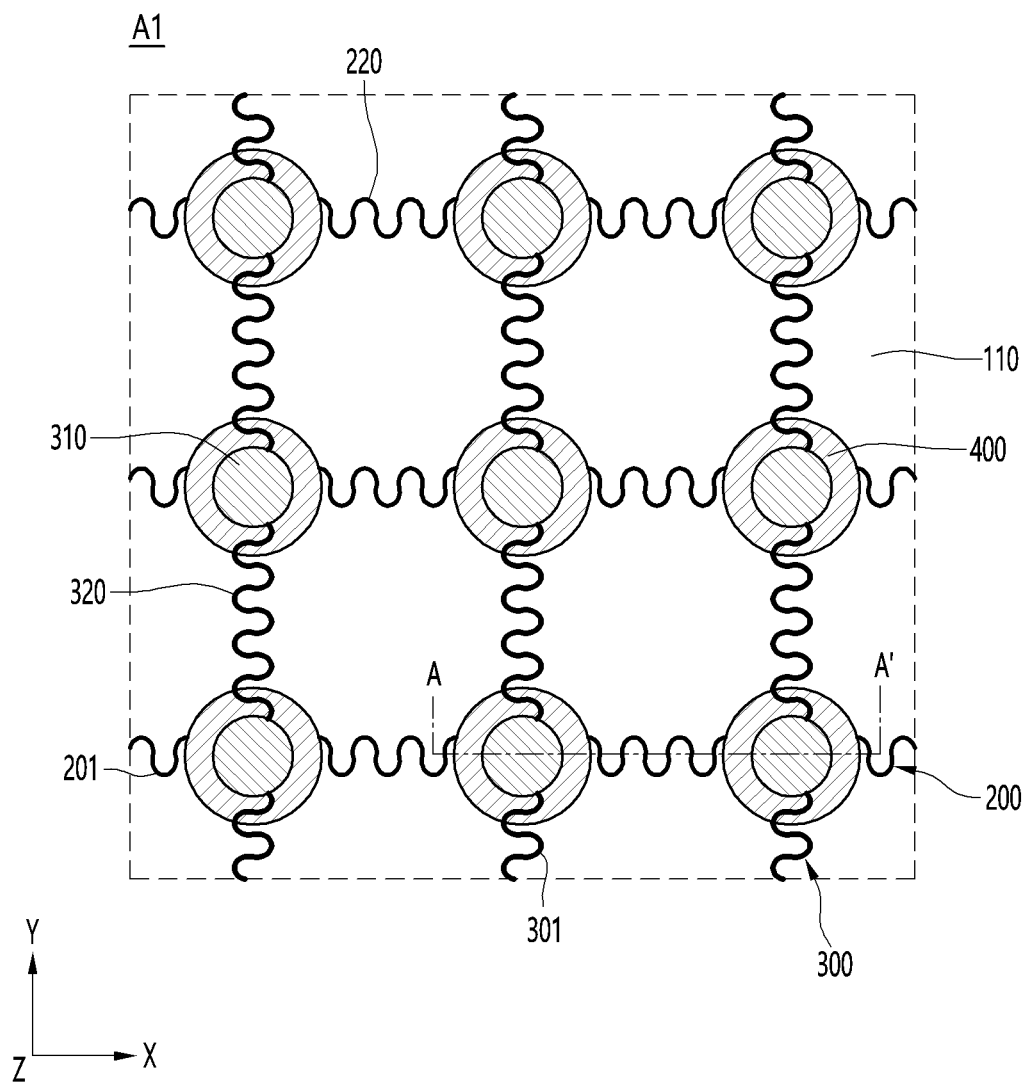
FIG. 4 is another top view of the region A1 in FIG. 1.
Figure 5:
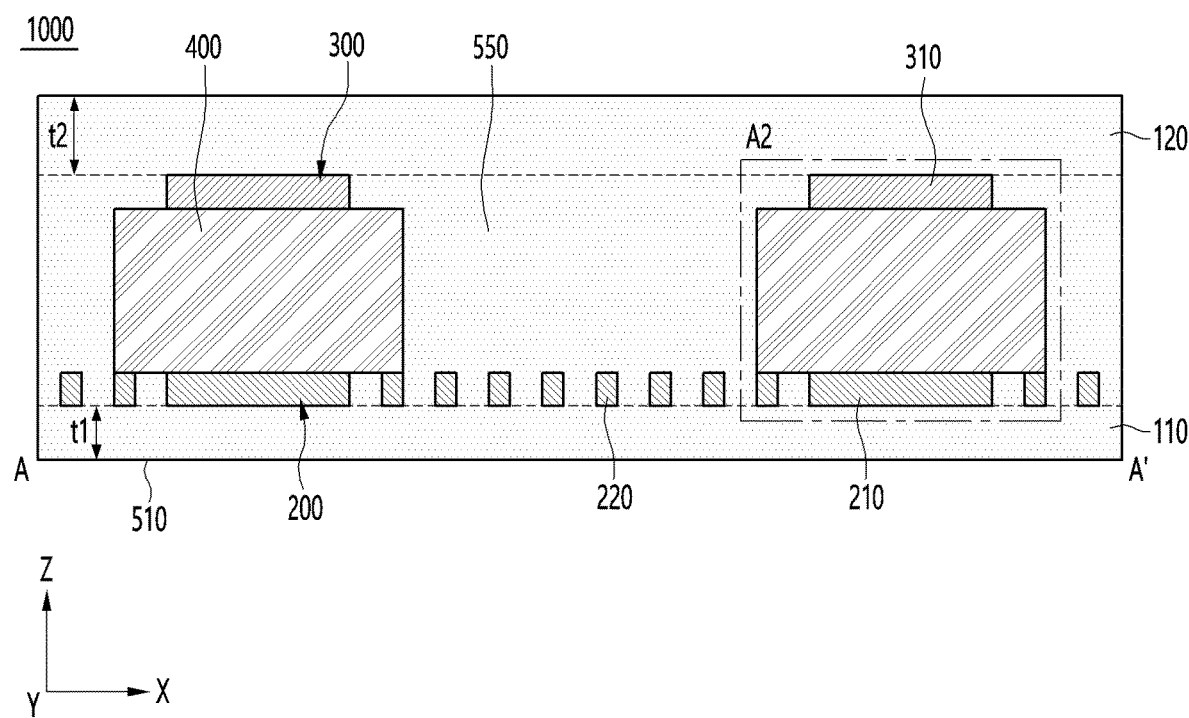
FIG. 5 is a cross-sectional view taken along line A-A' of FIG. 4.

Alternatively, when viewed in a plane, each of the plurality of first sub-wirings 201 may extend in the first direction in a curved shape as shown in FIG. 4. For example, each of the plurality of first sub-wirings 201 may be provided in a form in which a wavy pattern is repeated. That is, the first extension portion 220 of the first wiring 200 may have the curved shape extending in the first direction.

In this case, the first extension portion 220 may have a curvature pattern of about 3R to about 20R (mm). Accordingly, when the mask 1000 is stretched or contracted in one direction, the first wiring 200 may have the stretchable characteristics and may not be cut. Preferably, the first extension portion 220 may have a curvature pattern of about 5R to about 15R (mm). In addition, the first extension portion 220 may have an elongation of about 10% to about 50%. Accordingly, the first wiring 200 may have more improved stretchable characteristics, thereby improving reliability and improving adhesion to the user's skin.

Still alternatively, although not shown in the drawing, the first extension portion 220 may have a shape in which a pattern in which a straight line and a curve extending in the first direction are mixed is repeated. For example, when viewed from a plane, the first extension portion 220 positioned in a region overlapping a relatively curved region (nose, cheeks, etc.) of the user's face may be provided in the curved shape, and the first extension portion 220 positioned in a region overlapping a relatively planar region (forehead, etc.) may be provided in the linear shape. Accordingly, when the mask 1000 is attached to the user's face, it is possible to prevent the first wiring 200 from being damaged due to deformation of the mask 1000. In addition, the first extension portion 220 may be provided in a form in which the straight line and the curve are mixed to maintain electrical characteristics and reduce a ratio occupied by the first wiring 200. Therefore, the embodiment may reduce manufacturing costs of the first wiring 200 and minimize the loss of ultrasonic energy emitted from the piezoelectric element 400.

The piezoelectric element 400 may be disposed on the first base layer 110. The piezoelectric element 400 may be disposed on the first wiring 200. In detail, the piezoelectric element 400 may be disposed on the first extension portion 220 of the first wiring 200 to be electrically connected to the first wiring 200.

The piezoelectric element 400 may include a ceramic material. As an example, the piezoelectric element 400 may include at least one of ZnO, AlN, LiNbO$_4$, lead antimony stannate, lead magnesium tantalate, lead nickel tantalate, titanates, tungstates, zirconates, or lead including lead zirconate titanate [Pb(Zr$_x$Ti$_{1-x}$)O$_3$(PZT)], lead lanthanum zirconate titanate (PLZT), lead niobium Zirconate titanate (PNZT), BaTiO$_3$, SrTiO$_3$, lead magnesium niobate, lead nickel niobate, lead manganese niobate, lead zinc niobate, lead including lead titanate, barium, bismuth, or niobates of strontium.

The piezoelectric element 400 may be disposed on the first wiring 200 in plural. The plurality of piezoelectric elements 400 may be disposed to be spaced apart from each other on the first sub-wiring 201. For example, the plurality of piezoelectric elements 400 may be disposed on the first connection portion 210 on the first sub-wiring 201. In detail, one piezoelectric element 400 may be disposed on one first connection portion 210. A center of the lower surface of the piezoelectric element 400 may overlap the first sub-wiring 201 in the vertical direction. In detail, the center of the lower surface of the piezoelectric element 400 may overlap the first connection portion 210. In more detail, the center of the lower surface of the piezoelectric element 400 may overlap a center of the first connection portion 210.

The plurality of piezoelectric elements 400 may be spaced apart at equivalent intervals on the first sub-wiring 201. For example, the plurality of piezoelectric elements 400 disposed on one first sub-wiring 201 may be disposed at equivalent intervals based on the first direction. In addition, the piezoelectric elements 400 disposed on the adjacent first sub-wirings 201 may be disposed at equivalent intervals based on the second direction. Accordingly, a virtual line connecting centers of the adjacent plurality of piezoelectric elements 400 in the first direction and the second direction may have a mesh shape.

In addition, a piezoelectric element 400 disposed on one first sub-wiring 201 may overlap or not overlap a piezoelectric element 400 disposed on the first sub-wiring 201 closest to the one first sub-wiring 201 in the second direction. As an example, when viewed in a plane, the piezoelectric element 400 may be disposed in a zigzag shape on the adjacent first sub-wiring 201

In addition, a distance between some of the piezoelectric elements 400 may be disposed at equivalent intervals, and the remaining piezoelectric elements 400 may not be disposed at equivalent intervals. For example, the distance between the piezoelectric elements 400 may be disposed at equivalent intervals in a region overlapping a relatively planar region of a surface of the user's face. However, the distance between the piezoelectric elements 400 may not be disposed at equivalent intervals in a region overlapping a relatively curved skin region. That is, the distance between the piezoelectric elements 400 may be relatively narrow or large depending on the degree of curvature of the skin surface. As an example, the distance between the piezoelectric elements 400 of the region overlapping the curved region such as a user's nose and cheeks, may be relatively narrow. Accordingly, the mask 1000 according to the embodiment may effectively provide ultrasonic energy even to the curved skin.

The piezoelectric element 400 may be disposed on the entire region of the mask 1000 to generate evenly the ultrasonic energy. For example, the piezoelectric element 400 may generate ultrasonic energy of about 1 MHz or less by an applied current. In detail, the piezoelectric element 400 may generate ultrasonic energy of about 10 KHz to about 1 MHz. In more detail, the piezoelectric element 400 may generate ultrasonic energy of about 100 KHz to about 800 KHz. The ultrasonic energy generated by the piezoelectric element 400 may move in a direction of one surface of the mask 1000, and may be transmitted to the user's skin to massage the user's skin.

A thickness of the piezoelectric element 400 may be about 1500 μm or less. In detail, the thickness of the piezoelectric element 400 may be about 1200 μm or less. Preferably, the thickness of the piezoelectric element 400 may be about 1000 μm or less. It is preferable that the thickness of the piezoelectric element 400 satisfies the above-described range in consideration of the overall thickness and variable characteristics of the mask 1000.

The piezoelectric element 400 may have various shapes. For example, the piezoelectric element 400 may have a polygonal column shape in which lower and upper surfaces are polygonal, and the lower and upper surfaces may have a circular column shape. In addition, the piezoelectric element 400 may have a pillar shape in which one surface of the lower and upper surfaces is a polygonal and the other surface is circular. As an example, an area of at least one of the lower surface and the upper surface of the piezoelectric element 400 may be about 100 $mm^2$ or less.

As described above, the piezoelectric element 400 may have various pillar shapes, and intensity and an oscillation direction of ultrasonic energy generated according to the pillar shape may be controlled. In addition, the intensity of ultrasonic energy transmitted to the user's skin may be adjusted according to a size, arrangement interval, arrangement density, and the like of the piezoelectric element 400.

The piezoelectric element 400 may generate various waves. As an example, the piezoelectric element 400 may generate at least one wave of a transverse wave in which a traveling direction of wave and a vibration direction of medium are perpendicular, and a longitudinal wave in which the traveling direction of wave and the vibration direction of medium are the same. In addition, the piezoelectric element 400 may multiple-resonate. For example, the piezoelectric element 400 may include at least one via hole and may multiple-resonate by the formed via holes. In this case, an upper area of the via holes may be about 10% to about 45% of an area of the upper surface of the piezoelectric element 400 for multiple resonance. In addition, when the piezoelectric element 400 multiple-resonates by the via holes, the number of multiple resonant frequency regions may correspond to the number of the via holes. That is, the piezoelectric element 400 may emit wavelengths of various frequency ranges, for example, ultrasonic energy, as the number of the via holes increases in a set number range of via holes.

The second base layer 120 may be disposed on the piezoelectric element 400. The second base layer 120 is a portion that may be in contact with the skin while facing the user's skin, and may include a material harmless to the human body. In addition, the second base layer 120 may include a material having softness and elasticity. For example, the second base layer 120 may include at least one material of silicone, a thermoplastic resin, a thermoplastic silicone resin, a thermoplastic elastomer, a polyurethane elastomer, an ethylene vinyl acetate (EVA), a polyvinyl chloride (PVC) in which a harmless plasticizer and a stabilizer are added. Preferably, the second base layer 120 may include a silicone elastomer that is relatively light, may minimize irritation upon contact with the user's skin, and has a predetermined elasticity. The first base layer 110 may be provided with the same material as the second base layer 120.

The second base layer 120 may pass through the wavelengths emitted from the piezoelectric element 400 in the direction of one surface of the mask 1000 to transmit the wavelengths to the user's skin. That is, the second base layer 120 is transmission layer and may be a matching layer.

To this end, the thickness t2 of the second base layer 120 may vary depending on an impedance of the second base layer 120 and a driving frequency of the piezoelectric element 300. In addition, the thickness t2 of the second base layer 120 may be equal to or greater than the thickness of the first base layer 110.

As an example, when the driving frequency of the piezoelectric element 400 is about 1 MHz or less, the thickness t2 of the second base layer 120 may be about 50 μm to about 1 mm. When the thickness t2 of the second base layer 120 is less than about 50 μm, the thickness t2 of the second base layer 120 is relatively small, so that components disposed on the second base layer 120 may not be effectively protected. In detail, when the mask 1000 is elastically deformed and the second base layer 120 is elastically deformed, the wirings 200 and 300 and the piezoelectric element 400 on the second base layer 120 may not be effectively protected.

In addition, when the thickness t2 of the second base layer 120 exceeds about 10 mm, the thickness of the entire mask 1000 may be increased. It is preferable that the thickness t2 of the second base layer 120 satisfies the above-described range in order to effectively pass through the wavelengths emitted from the piezoelectric element 400. Preferably, the thickness t2 of the second base layer 120 may have a thickness range of 100 μm to about 1000 μm in consideration of reliability, transmission characteristics, variability, thickness, weight, and ultrasonic impedance characteristics of the mask 1000 to be manufactured.

That is, some of the ultrasonic energy emitted from the piezoelectric element 400 according to the embodiment may be emitted toward the second base layer 120 and pass through the second base layer 120 to be transmitted to the user's skin. In addition, another part of the ultrasonic energy may be emitted toward the first base layer 110 and reflected toward the second base layer 120 by the first base layer 110. Thereafter, the reflected ultrasonic energy may pass through the second base layer 120 to be transferred to the user's skin.

The second wiring 300 may be disposed on the second base layer 120. The second wiring 300 may be disposed on one surface of the second base layer 120 facing the piezoelectric element 400. The second wiring 300 may extend in a different direction from the first wiring 200 on the second base layer 120. For example, the second wiring 300 may extend in a second direction (y-axis direction) perpendicular to the first direction. The second wiring 300 may be in direct contact with one surface of the second base layer 120. The second wiring 300 may be formed on one surface of the second base layer 120 by a process such as deposition, printing, bonding, or the like. The second wiring 300 may be electrically connected to the piezoelectric element 400.

The second wiring 300 may include a conductive material. As an example, the second wiring 300 may include at least one metal of aluminum (Al), copper (Cu), silver (Ag), gold (Au), chromium (Cr), nickel (Ni), molybdenum (Mo), titanium (Ti), and alloys thereof. In addition, the second wiring 300 may include a non-metal such as carbon, and the like, and may include a conductive elastic body. The second wiring 300 may include the same material as the first wiring 200.

The second wiring 300 may have a single layer or a multiple layer structure. As an example, the second wiring 300 may have a single layer structure including one selected from the above-described materials. In addition, the second wiring 300 may have a multiple layer structure including a metal selected from the above-described materials and the conductive elastic body. The second wiring 300 may include the same material as the first wiring 200.

The second wiring 300 may include a plurality of second sub-wirings 301 disposed on the second base layer 120. Each of the plurality of second sub-wirings 301 may extend in the second direction and may be disposed to be spaced apart from each other in the first direction. The plurality of second sub-wirings 301 may be electrically connected to each other.

A thickness of the second sub-wiring 301 may be about 2 μm to about 50 μm. In detail, the thickness of the second sub-wiring 301 may be about 2 μm to about 40 μm. When the thickness of the second sub-wiring 301 is less than about 2 μm, electrical characteristics may be deteriorated, and it may be difficult to form uniformly. In addition, when the thickness of the second sub-wiring 301 exceeds about 50 μm, the overall thickness of the mask 1000 may be increased, and a manufacturing time of the second wire 300 may be increased. In addition, the thickness of the second sub-wiring 301 is too thick, and thus stretchable characteristics may be deteriorated. Preferably, the thickness of the second sub-wiring 301 may be about 5 μm to about 35 μm or less in consideration of stretchable characteristics in the horizontal direction, reliability, and process efficiency.

In addition, a line width of the second sub-wiring 301 may be about 50 μm to about 500 μm. In detail, the line width of the second sub-wiring 301 may be about 100 μm to about 450 μm. The line width of the second sub-wiring 301 may be greater than the thickness of the second sub-wiring 301. When the line width of the second sub-wiring 301 is less than about 50 μm, the reliability may be degraded, and when the line width of the second sub-wiring 301 exceeds about 500 μm, an elongation may be decreased and the stretchable characteristics may be deteriorated. Preferably, the line width of the second sub-wiring 301 may be about 100 μm to about 400 μm in consideration of the stretchable characteristics.

The second wiring 300 may include a second connection portion 310 and a second extension portion 320. For example, one of the second sub-wirings 301 may include the second connection portion 310 and the second extension portion 320 connected to the second connection portion 310.

The second connection portion 310 may be disposed in a region corresponding to an upper surface of the piezoelectric element 400. In detail, the second connection portion 310 may be disposed in a region overlapping the upper surface of the piezoelectric element 400 in the vertical direction. The second connection portion 310 may face the upper surface of the piezoelectric element 400. The second connection portion 310 may be provided in a number corresponding to the piezoelectric element 400.

The second connection portion 310 may have a shape corresponding to the upper surface of the piezoelectric element 400. The second connection portion 310 may have a width corresponding to the upper surface of the piezoelectric element 400. As an example, a width of the second connection portion 310 in the horizontal direction may be equal to or smaller than a width of the upper surface of the piezoelectric element 400 in the horizontal direction. In detail, the width of the second connection portion 310 in the horizontal direction may be about 50% to about 100% of the width of the upper surface of the piezoelectric element 400 in the horizontal direction. When the width of the second connection portion 310 in the horizontal direction is less than about 50%, electrical characteristics between the second wiring 300 and the piezoelectric element 400 may be deteriorated. In addition, when the width of the second connection portion 310 in the horizontal direction is greater than the width of the lower surface of the piezoelectric element 400, the transmittance of ultrasonic energy may be deteriorated. Therefore, it is preferable that the width of the second connection portion 310 in the horizontal direction satisfies the above-described range.

The second extension portion 320 may extend in the second direction from the second connection portion 310. The second extension portion 320 may be disposed between a plurality of second connection portions 310. In detail, the second extension portion 320 may be disposed between the second connection portions 310 spaced apart in the second direction. That is, the second extension portion 320 may connect between adjacent second connection portions 310.

The second wiring 300 may have various shapes. For example, when viewed in a plane, each of the plurality of second sub-wirings 301 may extend in the second direction in the linear shape as shown in FIG. 3. In detail, the plurality of second sub-wirings 301 may be spaced apart from the adjacent second sub-wirings 301 in the first direction at equivalent intervals and may extend in the second direction in the linear shape. That is, the second extension portion 320 of the second wiring 300 may have the linear shape extending in the second direction.

Alternatively, when viewed in a plane, each of the plurality of second sub-wirings 301 may extend in the second direction in the curved shape as shown in FIG. 4. For example, each of the plurality of second sub-wirings 301 may be provided in a form in which a wavy pattern is repeated. That is, the second extension portion 320 of the second wiring 300 may have the curved shape extending in the second direction.

In this case, the second extension portion 320 may have a curvature pattern of about 3R to about 20R (mm). Accordingly, when the mask 1000 is stretched or contracted in one direction, the second wiring 300 may have the stretchable characteristics and may not be cut. Preferably, the second extension portion 320 may have a curvature pattern of about 5R to about 15R (mm). In addition, the second extension portion 320 may have an elongation of about 10% to about 50%. Accordingly, the second wiring 300 may have more improved stretchable characteristics, thereby improving reliability and improving adhesion to the user's skin.

Still alternatively, although not shown in the drawing, the second extension portion 320 may have a shape in which a pattern in which a straight line and a curve extending in the first direction are mixed is repeated. For example, when viewed from a plane, the second extension portion 320 positioned in a region overlapping a relatively curved region (nose, cheeks, etc.) of the user's face may be provided in the curved shape, and the second extension portion 320 positioned in a region overlapping a relatively planar region (forehead, etc.) may be provided in the linear shape. Accordingly, when the mask 1000 is attached to the user's face, it is possible to prevent the second wiring 300 from being damaged due to deformation of the mask 1000. In addition, the second extension portion 320 may be provided in a form in which the straight line and the curve are mixed to maintain electrical characteristics and reduce a ratio occupied by the second wiring 300. Therefore, the embodiment may reduce manufacturing costs of the second wiring 300 and minimize the loss of ultrasonic energy emitted from the piezoelectric element 400.

The first wiring 200 and the second wiring 300 may be disposed to cross each other. In detail, when viewed in a plane as shown in FIG. 3, the first sub-wiring 201 and the second sub-wiring 301 may be disposed to cross each other in a mesh shape, and, an open region in which the wirings 200 and 300 are not disposed may be formed between the sub-wirings 201 and 301.

The piezoelectric element 400 may be disposed on a region where the first wiring 200 and the second wiring 300 cross each other. In detail, a center of the piezoelectric element 400 may overlap an intersection point of the first sub-wiring 201 and the second sub-wiring 301. In more detail, a center of each of the lower and upper surfaces of the piezoelectric element 400 may overlap a center of the first connection portion 210 of the first wiring 200 and a center of the second connection portion 310 of the second wiring 300.

In addition, although not shown in the drawings, a vibration member (not shown) may be further disposed on the piezoelectric element. In order to improve vibration characteristics of the piezoelectric element 400, the vibration member may be further disposed on the upper surface of the piezoelectric element 400. For example, the vibration member may be a vibration plate. The vibration member may be disposed between the piezoelectric element 400 and the second wiring 300.

The vibration member may be electrically connected to the piezoelectric element 400. The vibration member may include a metal material. As an example, the vibration member may include at least one metal of aluminum (Al), copper (Cu), zinc (Zn), iron (Fe), nickel (Ni), chromium (Cr), silver (Ag), gold (Pt), stainless steel (SUS), and alloys thereof.

The vibration member may have a shape corresponding to the piezoelectric element 400. For example, the vibration member may have a planar shape corresponding to the upper surface of the piezoelectric element 400. In addition, the vibration member may have a width in the horizontal direction corresponding to the upper surface of the piezoelectric element 400.

A thickness of the vibration member may be about 1500 μm or less. In detail, the thickness of the vibration member may be about 1200 μm or less. Preferably, the thickness of the vibration member may be about 1000 μm or less. It is preferable that the thickness of the vibration member satisfies the above-described range in consideration of the variable characteristics of the mask 1000 and the vibration characteristics of the piezoelectric element 400.

The mask 1000 according to the embodiment may include the protective layer 550. The protective layer 550 may be disposed between the first base layer 110 and the second base layer 120. The protective layer 550 may be disposed in direct contact with one surface of the first base layer 110 and one surface of the second base layer 120.

The protective layer 550 may be disposed between the first base layer 110 and the second base layer 120 to protect the piezoelectric element 400. In detail, the protective layer 550 may be disposed to surround the piezoelectric element 400 and the wirings 200 and 300 between the base layers 110 and 120 to protect the components.

The protective layer 550 may include a material having softness and elasticity. For example, the protective layer 550 may include at least one material of silicone, a thermoplastic resin, a thermoplastic silicone resin, a thermoplastic elastomer, a polyurethane elastomer, an ethylene vinyl acetate (EVA), a polyvinyl chloride (PVC) in which a harmless plasticizer and a stabilizer are added. The protective layer 550 may be preferable to include a silicone elastomer that is relatively light, may minimize irritation upon contact with the user's skin, and has a predetermined elasticity.

The protective layer 550 may be connected to the first base layer 110 and the second base layer 120. For example, the protective layer 550 may be integrally formed with the first base layer 110 and the second base layer 120. The protective layer 550 may be physically connected to the first base layer 110 and the second base layer 120 to protect components disposed therein.

The protective layer 550 may include the same material as the first base layer 110 and the second base layer 120. That is, the first base layer 110, the second base layer 120, and the protective layer 550 may include the same kind of material, thereby having an improved bonding force.

Figure 6:
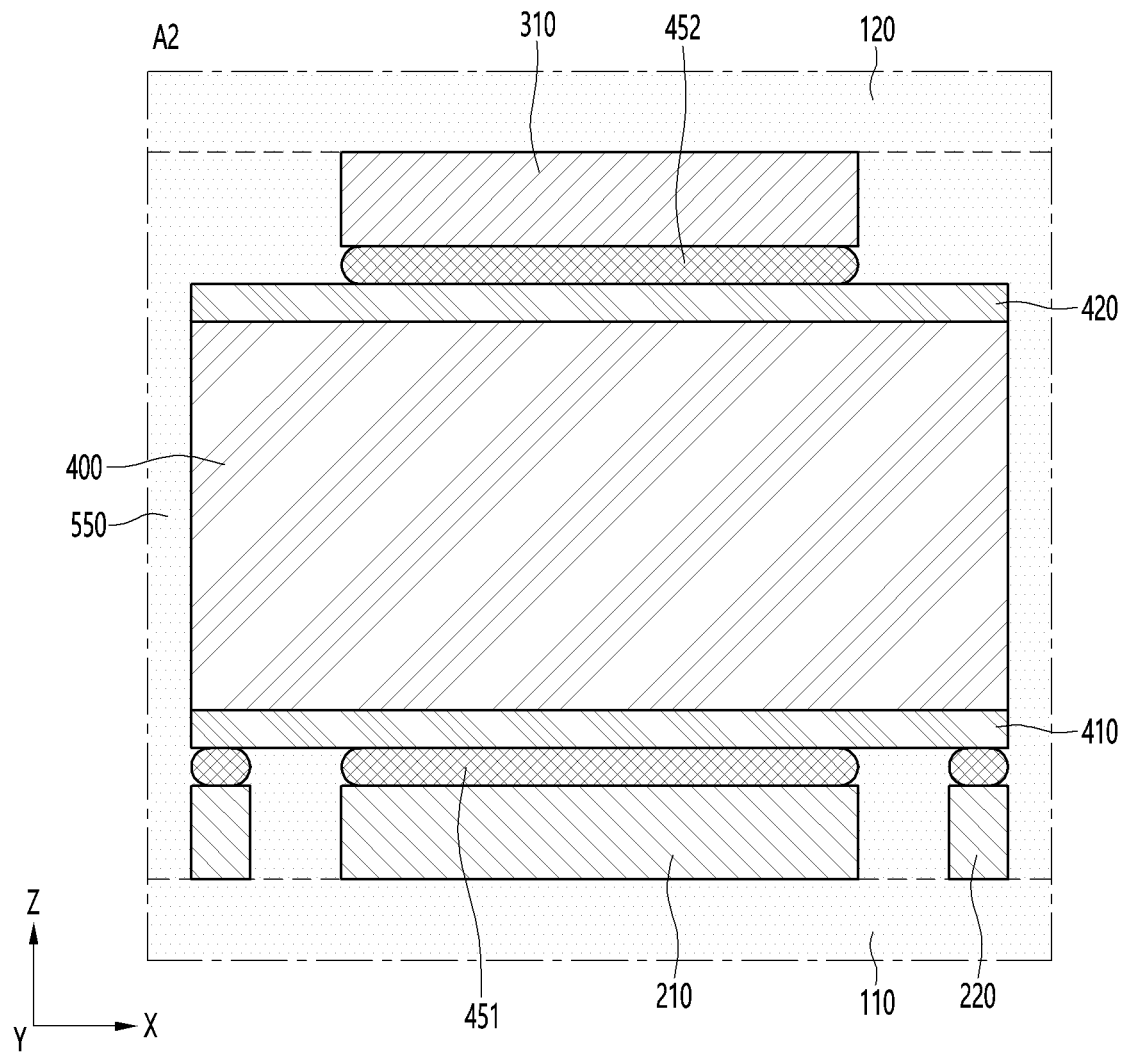
FIG. 6 is an enlarged view of region A2 in FIG. 5.

Referring to FIG. 6, a connection relationship between the piezoelectric element 400, the first wiring 200, and the second wiring 300 will be described in more detail.

Referring to FIG. 6, the piezoelectric element 400 may be electrically connected to the first wiring 200 and the second wiring 300. In detail, the piezoelectric element 400 may include a first electrode 410 disposed on a lower surface thereof. The first electrode 410 may be disposed in an area of about 80% or more of the entire area of the lower surface of the piezoelectric element 400 in consideration of electrical characteristics. The first electrode 410 may be disposed in an area of about 90% of the entire area of the lower surface of the piezoelectric element 400. In addition, the first electrode 410 may be disposed on the entire region of the lower surface of the piezoelectric element 400.

The first electrode 410 may include a conductive material. As an example, the first electrode 410 may include a metal material. In detail, the first electrode 410 may include at least one metal of aluminum (Al), copper (Cu), silver (Ag), gold (Au), chromium (Cr), nickel (Ni), molybdenum (Mo), titanium (Ti), and alloys thereof.

The first electrode 410 may be disposed facing the first wire 200 and may be electrically connected to the first wire 200. In detail, a first bonding layer 451 may be disposed between the first electrode 410 and the first wiring 200. The first bonding layer 451 may physically and electrically connect the first electrode 410 and the first wiring 200. An overlapping ratio between the first bonding layer 451 and the first wiring 200 may be about 20% or more in consideration of physical and electrical characteristics. In detail, an overlapping ratio of one surface of the first wiring 200 facing the piezoelectric element 400 and the first bonding layer 451 may be about 20% or more.

The first bonding layer 451 may include at least one metal of aluminum (Al), copper (Cu), silver (Ag), gold (Au), chromium (Cr), nickel (Ni), molybdenum (Mo), titanium (Ti), and alloys thereof.

A thickness of the first bonding layer 451 may be about 100 μm or less. In detail, the thickness of the first bonding layer 451 may be about 20 μm to about 80 μm. Preferably, the thickness of the first bonding layer 451 may be about 30 μm to about 60 μm.

The first bonding layer 451 may be disposed between the first electrode 410 and the first wiring 200 to serve as a conductive adhesive. As an example, the first bonding layer 451 may be applied in a form of a paste on the first wiring 200, and the piezoelectric element 400 including the first electrode 410 may be disposed on the first bonding layer 451. Accordingly, the piezoelectric element 400 may be physically and electrically connected to the first wiring 200.

The piezoelectric element 400 may include a second electrode 420 disposed on an upper surface thereof. The second electrode 420 may be disposed in an area of about 80% or more of the entire area of the upper surface of the piezoelectric element 400 in consideration of electrical characteristics. In detail, the second electrode 420 may be disposed in an area of about 90% of the entire area of the upper surface of the piezoelectric element 400. In addition, the second electrode 420 may be disposed on the entire region of the lower surface of the piezoelectric element 400.

The second electrode 420 may include a conductive material. As an example, the second electrode 420 may include a metal material. In detail, the second electrode 420 may include at least one metal of aluminum (Al), copper (Cu), silver (Ag), gold (Au), chromium (Cr), nickel (Ni), molybdenum (Mo), titanium (Ti), and alloys thereof.

The second electrode 420 may be disposed facing the second wiring 300 and may be electrically connected to the second wiring 300. In detail, a second bonding layer 452 may be disposed between the second electrode 420 and the second wiring 300. The second bonding layer 452 may physically and electrically connect the second electrode 420 and the second wiring 300. An overlapping ratio between the second bonding layer 452 and the second wiring 300 may be about 20% or more in consideration of physical and electrical characteristics. In detail, an overlapping ratio between one surface of the second wiring 300 facing the piezoelectric element 400 and the second bonding layer 452 may be about 20% or more.

The second bonding layer 452 may include at least one metal of aluminum (Al), copper (Cu), silver (Ag), gold (Au), chromium (Cr), nickel (Ni), molybdenum (Mo), titanium (Ti), and alloys thereof.

A thickness of the second bonding layer 452 may be about 100 μm or less. In detail, the thickness of the second bonding layer 452 may be about 20 μm to about 80 μm. Preferably, the thickness of the second bonding layer 452 may be about 30 μm to about 60 μm.

The second bonding layer 452 may be disposed between the second electrode 420 and the second wiring 300 to serve as a conductive adhesive. As an example, the second bonding layer 452 may be applied in the form of the paste on the second wiring 300, and the piezoelectric element 400 including the second electrode 420 may be disposed on the second bonding layer 452. Accordingly, the piezoelectric element 400 may be physically and electrically connected to the second wiring 300.

The thickness of the first bonding layer 451 may be the same as or different from the thickness of the second bonding layer 452. As an example, the thickness of the first bonding layer 451 may be provided with the same thickness as the second bonding layer 452 to improve the variability of the mask 1000. As another example, the thickness of the first bonding layer 451 may be greater than the thickness of the second bonding layer 452. Accordingly, the wavelengths emitted from the piezoelectric element 400 toward the first base layer 110 may be reflected by the first bonding layer 451 to move toward the second base layer 120.

The protective layer 550 may be disposed to surround the piezoelectric element 400, the first wiring 200, the second wiring 300, the first electrode 410, the second electrode 420, the first bonding layer 451, and the second bonding layer 452, and it is possible to prevent the components from being exposed to the outside.

Figure 7:
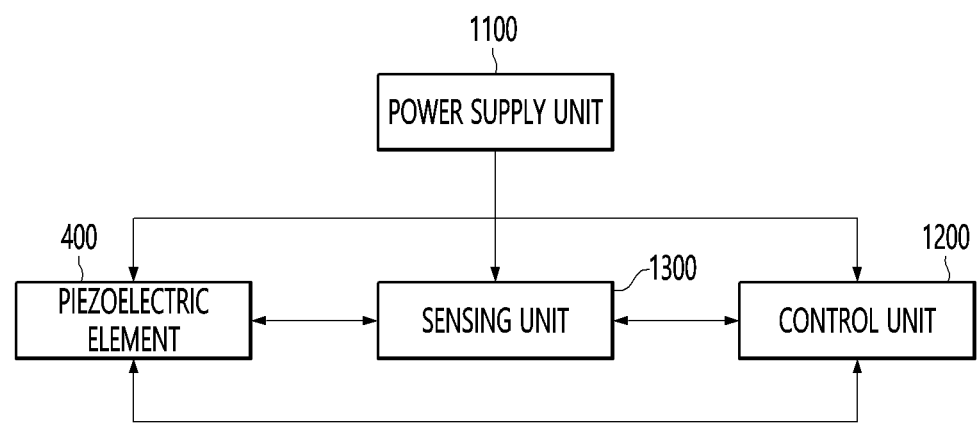
FIG. 7 is a block diagram illustrating a component of a mask according to a first embodiment.

FIG. 7 is a block diagram illustrating a component of a mask according to a first embodiment.

The mask 1000 according to the first embodiment may include a power supply unit 1100. The power supply unit 1100 may supply power to the mask 1000. As an example, the power supply unit 1100 may be a separate external power connected to the mask 1000. In addition, the power supply unit 1100 may be a battery disposed inside and outside the mask 1000. The power supply unit 1100 may supply power to the piezoelectric element 400, a control unit 1200, and a sensing unit 1300 to be described later.

The mask 1000 according to the first embodiment may include the control unit 1200. The control unit 1200 may control the driving frequency of the piezoelectric element 400. In general, a piezoelectric element has a resonant frequency and drives the resonant frequency as a driving frequency for optimal ultrasonic output.

However, the mask 1000 according to the first embodiment may change the driving frequency of the piezoelectric element 400 by the control unit 1200 and operate in various frequency bands. For example, the piezoelectric element 400 may be driven at a resonant frequency or a different frequency from the resonant frequency by the control unit 1200.

In detail, the control unit 1200 may control the driving frequency of the piezoelectric element 400 in a frequency band defined as a first range. The first range is a range determined by the resonant frequency and an anti-resonant frequency of the piezoelectric element 400 and may satisfy the following [Equation 1].

$$fo = fr \pm k^*(fa-fr) \qquad \text{[Equation 1]}$$

(fo is the driving frequency of the piezoelectric element according to the embodiment, fr is the resonant frequency of the piezoelectric element according to the embodiment. In addition, k is a constant value, and fa is the anti-resonant frequency of the piezoelectric element)

In this case, a value of the constant k in [Equation 1] may be about 0.2 to about 0.3. In detail, the value of the constant k may be about 0.22 to about 0.27. When the value of the constant k is less than about 0.2, a change in the driving frequency of the piezoelectric element 400 may be insignificant. In addition, when the value of the constant k exceeds about 0.3, a change in the driving frequency of the piezoelectric element 400 may be too large, and some ultrasonic energy may be lost. In addition, a change in temperature of the piezoelectric element 400 according to a change in driving frequency of the piezoelectric element 400 may be too large to be suitable for use on the user's skin.

Preferably, the value of the constant k may be about 0.25 in consideration of effects such as effective transmission of ultrasonic energy to the user's skin and cooling and heating. In this case, the driving frequency fo of the piezoelectric element may satisfy the following [Equation 2].

$$fo = fr \pm 0.25^*(fa-fr) \qquad \text{[Equation 2]}$$

(fo is the driving frequency of the piezoelectric element according to the embodiment. In addition, fr is the resonant frequency of the piezoelectric element according to the embodiment, and fa is the anti-resonant frequency of the piezoelectric element.)

That is, the control unit 1200 may control the driving frequency of the piezoelectric element 400 within the first range according to the Equations, and the mask 1000 may operate at the driving frequency controlled by the control unit 1200.

The control unit 1200 may set a first frequency defined as a frequency band higher than the resonant frequency fr of the piezoelectric element 400 as the driving frequency within the first range. In addition, the control unit 1200 may set a second frequency defined as a frequency band lower than the resonant frequency within the first range as the driving frequency.

The control unit 1200 may control a temperature of the mask 1000. For example, when the mask 1000 operates at the first frequency compared to when the mask 1000 operates at a resonant frequency, the temperature of the piezoelectric element 400 may decrease. Accordingly, the overall temperature of the mask 1000 may be reduced compared to the mask 1000 operating at the resonant frequency.

In addition, when the mask 1000 operates at the second frequency, the temperature of the piezoelectric element 400 may be increased. Accordingly, the overall temperature of the mask 1000 may be increased compared to the mask 1000 operating at the resonant frequency.

That is, the temperature of the mask 1000 according to the first embodiment may change according to the driving frequency of the piezoelectric element 400, and the user may select an operation mode of the mask 1000 to set the temperature of the mask 1000. In detail, the user may select the operation mode of the mask 1000 to control a surface temperature of the mask 1000 in direct contact with the user's skin, for example, a surface temperature of the second base layer 120.

For example, the user may select the operation mode of the mask 1000 as a normal mode, and the mask 1000 may operate at the resonant frequency of the piezoelectric element 400 in the normal mode.

In addition, the user may select the operation mode of the mask 1000 as a cooling mode. Here, the cooling mode may refer to a mode operating at a temperature lower than a temperature when the mask 1000 operates at a resonant frequency. In this case, the mask 1000 may operate at the first frequency, for example, a frequency higher than the resonant frequency. Accordingly, the temperature of the piezoelectric element 400 may be driven at a temperature lower than when the piezoelectric element 400 operates at the resonant frequency, and heat generation of the entire mask 1000 may be reduced.

In addition, the user may select the operation mode of the mask 1000 as a heating mode. Here, the thermal mode may refer to a mode operating at a temperature higher than a temperature when the mask 1000 operates at a resonant frequency. In this case, the mask 1000 may operate at the second frequency, for example, a frequency lower than the resonant frequency. Accordingly, the temperature of the piezoelectric element 400 may be driven at a temperature higher than when the piezoelectric element 400 operates at the resonant frequency, and heat generation of the entire mask 1000 may be increased.

In more detail, when the mask 1000 is operated in the normal mode, the control unit 1200 may control the driving frequency of the piezoelectric element 400 so as to have a temperature defined as a first temperature when the mask 1000 is operated.

In addition, when the mask 1000 is operated in the cooling mode operating at the first frequency described above, the control unit 1200 may control the driving frequency of the piezoelectric element 400 so as to have a temperature defined as a second temperature lower than the first temperature when the mask 1000 is operated. In this case, as a difference between the first frequency and the resonant frequency increases, the second temperature may gradually decrease.

In addition, when the mask 1000 is operated in the heating mode operating at the second frequency described above, the control unit 1200 may control the driving frequency of the piezoelectric element 400 so as to have a temperature defined as a third temperature higher than the first temperature when the mask 1000 is operated. In this case, as a difference between the second frequency and the resonant frequency increases, the second temperature may gradually increase.

The mask 1000 according to the first embodiment may include the sensing unit 1300. The sensing unit 1300 may be connected to the control unit 1200 to sense the temperature of the mask 1000. In detail, the sensing unit 1300 is disposed in the mask 1000 to sense a temperature of at least one of the piezoelectric element 400, the protective layer 550, the first base layer 110, and the second base layer 120. For example, the sensing unit 1300 may sense the surface temperature of the mask 1000 in direct contact with the user's skin, for example, the surface temperature of the second base layer 120.

The sensing unit 1300 may include a temperature sensor. As an example, the sensing unit 1300 may include at least one sensor selected from a thermocouple, resistance temperature detectors (RTD) sensor, a thermistor sensor, and a bimetal type.

When the mask 1000 is operated in the normal mode and/or the cooling mode described above, the mask 1000 may operate at a relatively low temperature. In addition, when the mask 1000 is operated in the heating mode described above, the mask 1000 may operate at a relatively high temperature.

In this case, the temperature of the mask 1000 may directly affect the user's skin. For example, an appropriate heating temperature and cooling temperature may widen or narrow pores of the user to help absorb cosmetics or drugs and obtain a skin soothing effect. However, excessive heating and cooling temperatures may adversely affect the user's skin. As an example, when the mask 1000 is operated in the heating mode for a long time, a burn such as a low-temperature burn may occur on the user's skin, and an excessive cooling temperature may block pores to prevent absorption of cosmetics or drugs.

However, the mask 1000 according to the first embodiment may prevent the above-described problem by the sensing unit 1300. That is, the sensing unit 1300 may transmit temperature information of the mask 1000 to the control unit 1200, and the control unit 1200 may correct the operation of the piezoelectric element 400 and/or the driving frequency of the piezoelectric element 400 based on the received information.

Figure 8:
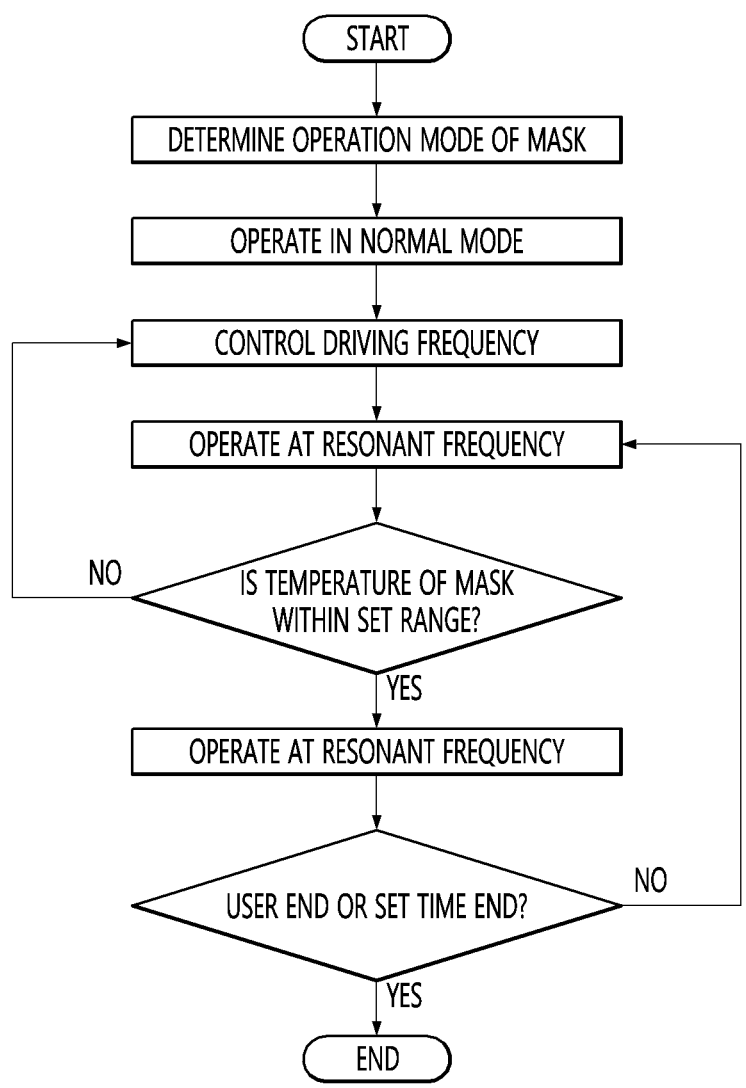
FIGS. 8 to 10 are flowcharts for each operation mode of the mask according to the first embodiment.
Figure 9:
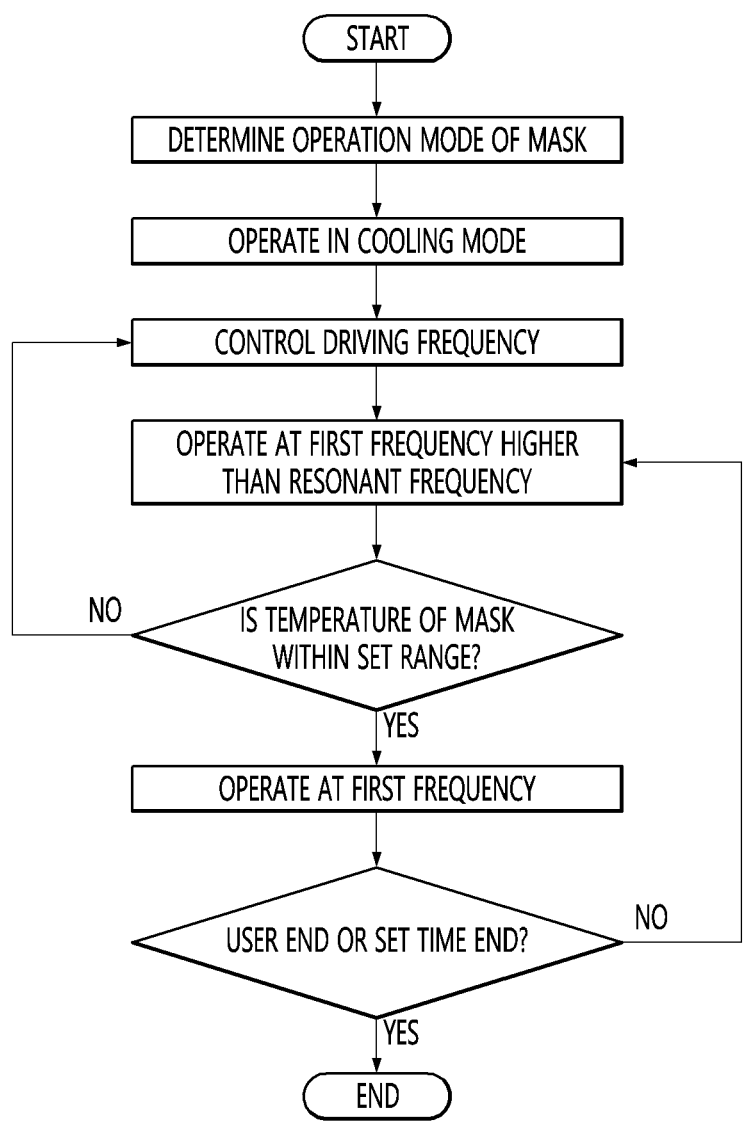
Figure 10:
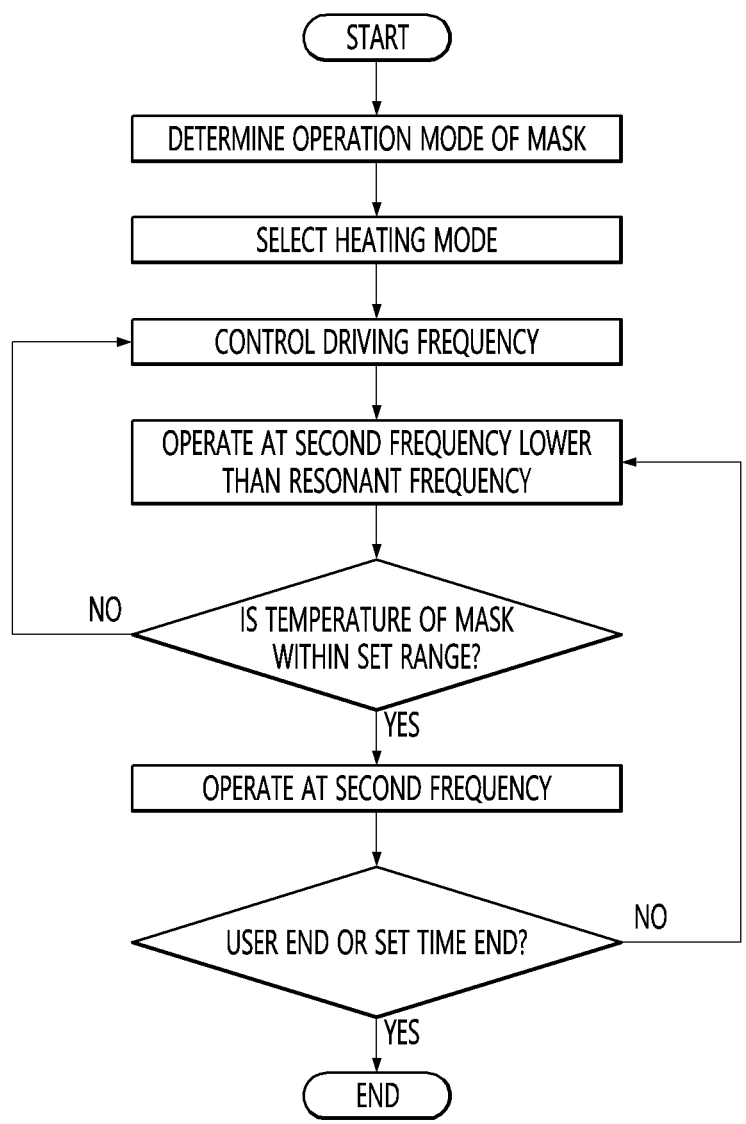

This will be described in more detail with reference to FIGS. 8 to 10. FIGS. 8 to 10 are flowcharts of operation modes of the mask according to the first embodiment.

First, referring to FIG. 8, the mask 1000 may operate in the normal mode according to a user's selection. In this case, the control unit 1200 may set a frequency corresponding to the normal mode as the driving frequency of the piezoelectric element 400. Accordingly, the mask 1000 may operate at the resonant frequency.

While the mask 1000 operates in the normal mode, the sensing unit 1300 may sense the temperature of the mask 1000. As an example, when the temperature of the mask 1000, for example, the surface temperature of the second base layer 120, satisfies the set temperature, the mask 1000 may operate until a time at which the resonant frequency is set to the drive frequency or until the end time of the user.

However, when the temperature of the mask 1000 sensed by the sensing unit 1300 is less than or exceeds the set temperature, the control unit 1200 may control the driving frequency of the piezoelectric element 400. In detail, the control unit 1200 may correct the driving frequency of the piezoelectric element 400 to be higher or lower than the current driving frequency to control the temperature of the mask 1000 so as to correspond to the normal mode. Thereafter, when the temperature of the mask 1000 reaches a set temperature range, the control unit 1200 may control the driving frequency of the piezoelectric element 400 to the resonant frequency again.

In addition, referring to FIG. 9, the mask 1000 may operate in the cooling mode according to a user's selection. In this case, the control unit 1200 may set a frequency corresponding to the cooling mode as the driving frequency of the piezoelectric element 400. Accordingly, the mask 1000 may operate at the first frequency.

While the mask 1000 operates in the cooling mode, the sensing unit 1300 may sense the temperature of the mask 1000. As an example, when the temperature of the mask 1000 satisfies the set temperature, the mask 1000 may operate until a time at which the first frequency is set to the drive frequency or until the end time of the user.

However, when the temperature of the mask 1000 sensed by the sensing unit 1300 exceeds the set temperature, the control unit 1200 may control the driving frequency of the piezoelectric element 400. For example, when the temperature of the mask 1000 is lower than the set temperature, the control unit 1200 may correct the driving frequency of the piezoelectric element 400 to be lower than the current driving frequency. In more detail, the control unit 1200 may lower the driving frequency of the piezoelectric element 400 from the first frequency to the resonant frequency band, or may lower the driving frequency from the first frequency to the second frequency region. Accordingly, since the temperature of the mask 1000 may be increased, it is possible to prevent the user's skin from being damaged. Thereafter, when the temperature of the mask 1000 reaches the set temperature range, the control unit 1200 may control the driving frequency of the piezoelectric element 400 to the first frequency again.

In addition, referring to FIG. 10, the mask 1000 may operate in the heating mode according to a user's selection. In this case, the control unit 1200 may set a frequency corresponding to the heating mode as the driving frequency of the piezoelectric element 400. Accordingly, the mask 1000 may operate at the second frequency.

While the mask 1000 operates in the heating mode, the sensing unit 1300 may sense the temperature of the mask 1000. As an example, when the temperature of the mask 1000 satisfies the set temperature, the mask 1000 may operate until a time at which the second frequency to the driving frequency or until the end time of the user.

However, when the temperature of the mask 1000 sensed by the sensing unit 1300 exceeds the set temperature, the control unit 1200 may control the driving frequency of the piezoelectric element 400. In detail, the control unit 1200 may correct the driving frequency of the piezoelectric element 400 to be higher than the current driving frequency. In more detail, the control unit 1200 may higher the driving frequency of the piezoelectric element 400 from the second frequency to the resonant frequency band, or may higher from the second frequency to the first frequency region. Accordingly, since the temperature of the mask 1000 may be decreased, it is possible to prevent the user's skin from being damaged. Thereafter, when the temperature of the mask 1000 reaches the set temperature range, the control unit 1200 may control the driving frequency of the piezoelectric element 400 to the second frequency again.

Figure 11:
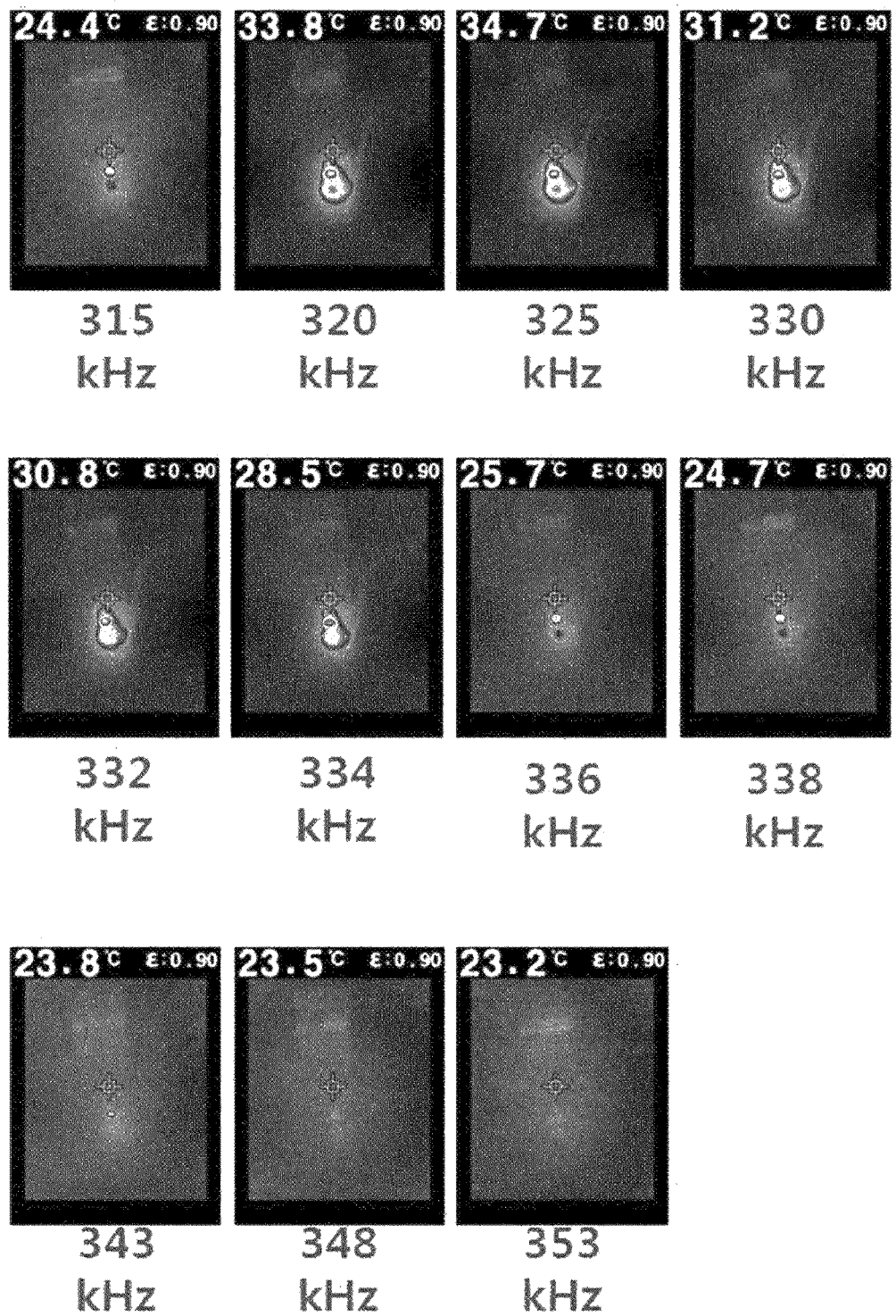
FIG. 11 is data on a temperature for each driving frequency of a piezoelectric element according to the first embodiment.
Figure 12:
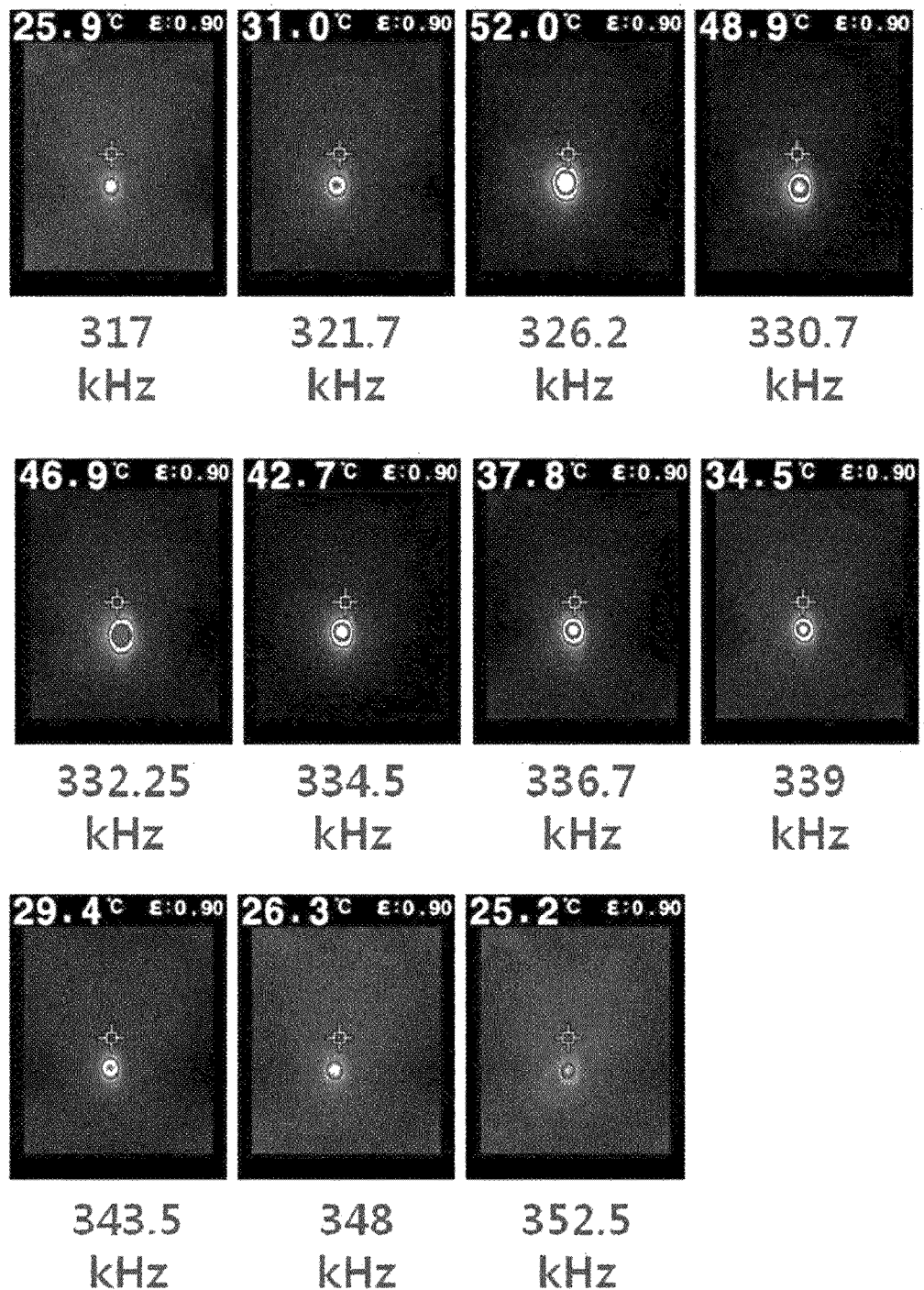
FIG. 12 is data on a temperature of the mask for each driving frequency of the mask according to the first embodiment.

FIG. 11 is data on the temperature of the piezoelectric element according to the driving frequency according to the first embodiment, and FIG. 12 is data on the temperature of the mask according to the driving frequency of the mask according to the first embodiment. In addition, FIG. 13 is a graph of a temperature and impedance for each driving frequency of the piezoelectric element according to the first embodiment, and FIG. 14 is data on a temperature and impedance of the mask for each driving frequency of the mask according to the first embodiment.

Figure 13:
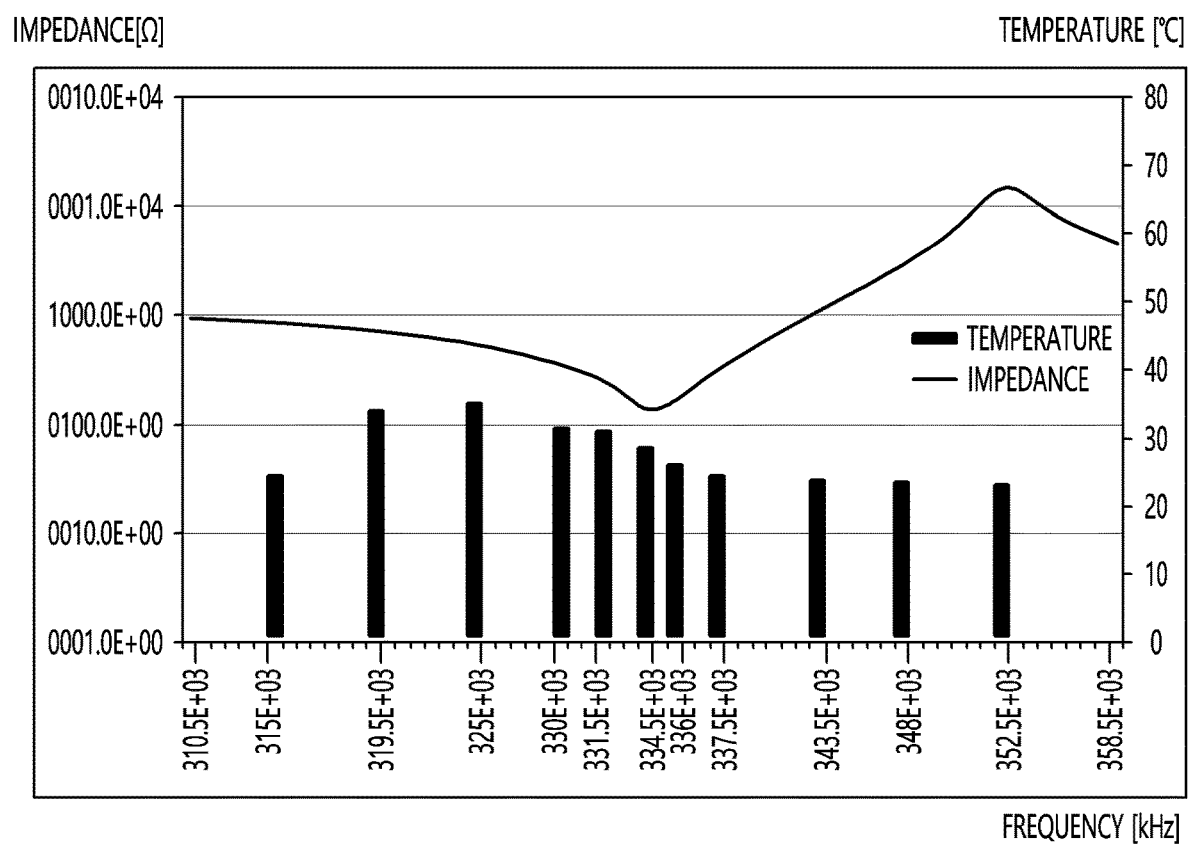
FIG. 13 is a graph of a temperature and impedance for each driving frequency of the piezoelectric element according to the first embodiment.

In detail, FIGS. 11 and 13 are data obtained by measuring temperature and impedance for each frequency by omitting the first base layer 110, the second base layer 120, and the protective layer 550 and connecting only electrodes to the piezoelectric element 400.

Figure 14:
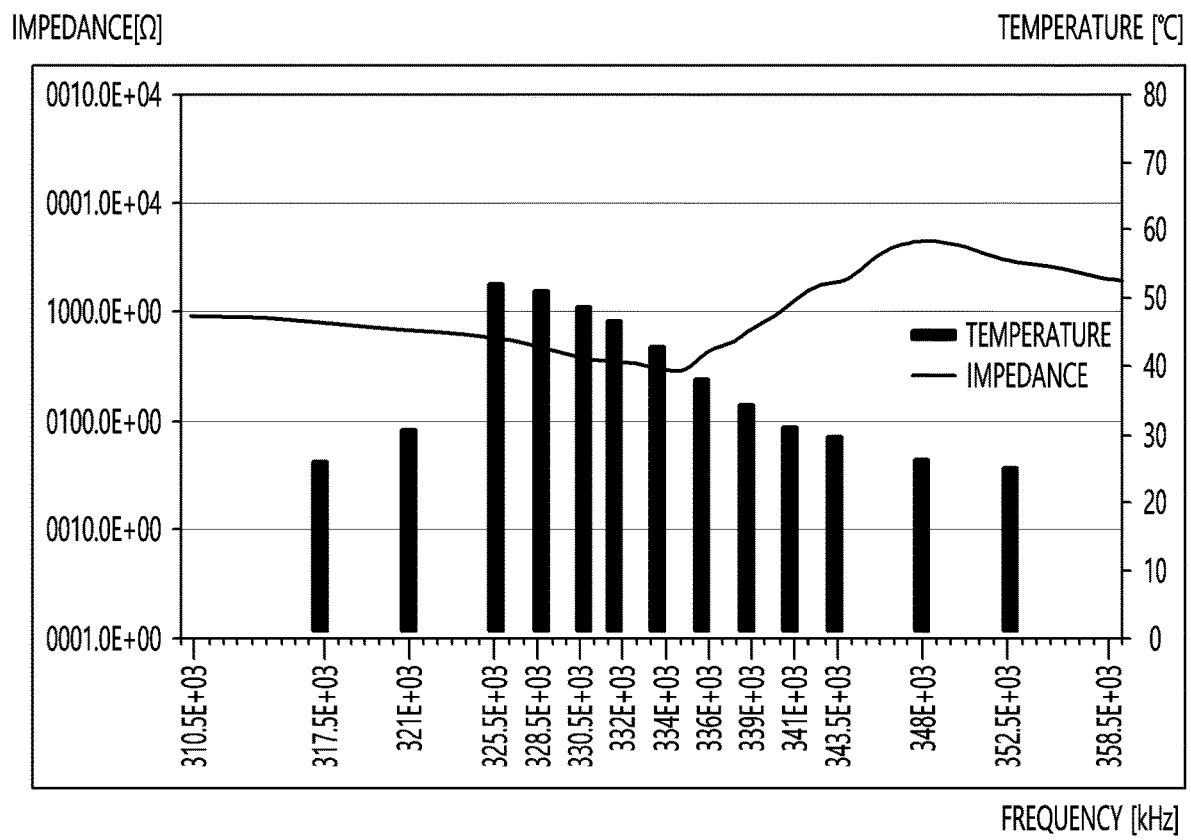
FIG. 14 is data on a temperature and impedance of the mask for each driving frequency of the mask according to the first embodiment.

In addition, FIGS. 12 and 14 are data obtained by measuring the temperature and impedance of the mask 1000 for each driving frequency by disposing the first base layer 110 and the second base layer 120 on the upper and lower portions of the protective layer 550 and disposing the piezoelectric element 400 and electrodes in the protective layer 550 to manufacture the mask. In detail, FIG. 12 is data obtained by measuring the surface temperature of the second base layer 120 in contact with the user's skin for each driving frequency of the piezoelectric element 400.

In addition, in FIGS. 11 and 12, the closer to red, the higher the temperature, and the closer to blue, the lower the temperature.

Referring to FIGS. 11 to 14, the resonant frequency of the piezoelectric element 400 according to the first embodiment may be about 334 kHz. When the mask 1000 is driven at the resonant frequency, it is possible to provide ultrasonic waves of about 334.5 kHz to the user's skin. In this case, the temperature of the piezoelectric element 400 may be about 28.5° C., and the temperature of the mask 1000 defined as the above-described first temperature may be about 42.7° C.

In addition, when the resonant frequency of the piezoelectric element 400 is about 334 khz, the anti-resonant frequency of the piezoelectric element 400 may be about 353 khz, and a minimum and maximum driving frequency range of the piezoelectric element 400 may be about 329.25 khz to about 338.75 khz according to [Equation 2] described above.

$$fo = fr \pm 0.25*(fa-fr) \quad \text{[Equation 2]}$$

(fo is the driving frequency of the piezoelectric element according to the embodiment. In addition, fr is the resonant frequency of the piezoelectric element according to the embodiment, and fa is the anti-resonant frequency of the piezoelectric element.)

That is, when the mask 1000 operates in a maximum frequency value of the above-described equation, for example, in the cooling mode (about 338.75 khz), the temperature of the piezoelectric element 400 may be about 24.7° C. (338 khz in FIG. 11), and the temperature of the mask 1000 defined as the above-described second temperature may be about 34.5° C. (339 khz in FIG. 12). That is, the mask 1000 may operate at a temperature lower than a body temperature of the user to provide the cooling effect to the user.

In this case, when the driving frequency of the piezoelectric element 400 is out of the above-described range, the temperature of the mask 1000 may be too low. For example, when the driving frequency of the piezoelectric element 400 is about 353 khz (see FIG. 11), the temperature of the piezoelectric element 400 may be about 23.2° C., and the temperature of the mask 1000 is about 25.2° C. (see FIG.

12). That is, an excessively low temperature may be provided to the user's skin, which may damage the user's skin.

In addition, when the mask 1000 operates in a minimum frequency value of the above-described equation, for example, in a heating mode (about 329.25 kHz), the temperature of the piezoelectric element 400 may be about 31.2° C. (330 kHz in FIG. 11), and the temperature of the mask 1000 defined as the above-described third temperature may be about 48.9° C. (330.7 kHz in FIG. 12). That is, the mask 1000 may operate at a temperature higher than the body temperature of the user to provide a heating effect to the user.

In this case, when the driving frequency of the piezoelectric element 400 is out of the above-described range, the temperature of the mask 1000 may be too high. For example, when the driving frequency of the piezoelectric element 400 is about 325 khz (see FIG. 11), the temperature of the piezoelectric element 400 may be about 34.7° C., and the temperature of the mask 1000 may be about 52° C. (see FIG. 12). That is, the heat effect on the user's skin may be excessive, which may cause a low-temperature burn on the user's skin.

The mask 1000 according to the first embodiment may operate in various modes to provide various temperatures to the user's skin. For example, the mask 1000 may operate in the normal mode, the cooling mode, the heating mode, or the like to provide the cooling or heating effect to the user's skin. Therefore, the mask 1000 according to the embodiment may provide the cooling or heating effect to the user's skin by omitting a separate heating member, a cooling member, and the like and using the piezoelectric element 400.

In addition, the mask 1000 according to the embodiment may include the sensing unit 1300, and the control unit 1200 may control the driving frequency and temperature of the mask 1000 based on temperature information sensed by the sensing unit 1300. Accordingly, the mask 1000 according to the embodiment may prevent the skin of a user who uses the mask 1000 from being damaged, and may control so that cosmetics or drugs may be effectively supplied to the user's skin.

Hereinafter, a mask according to a second embodiment will be described with reference to FIGS. 15 to 18.

Figure 15:
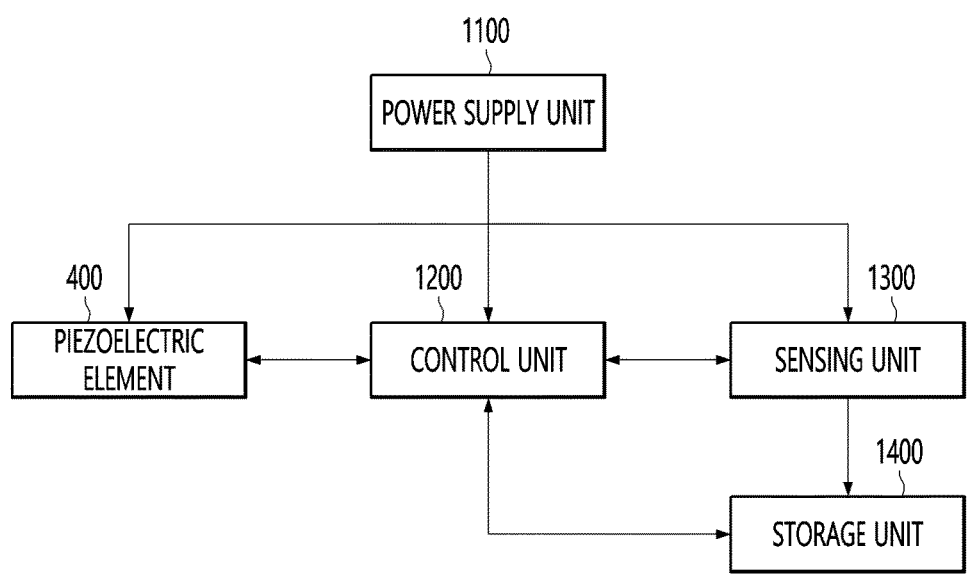
FIG. 15 is a block diagram illustrating a component of a mask according to a second embodiment.

First, referring to FIG. 15, a mask 1000 according to the second embodiment may include a power supply unit 1100. The power supply unit 1100 may supply power to the mask 1000. As an example, the power supply unit 1100 may be a separate external power connected to the mask 1000. In addition, the power supply unit 1100 may be a battery disposed inside and outside the mask 1000. The power supply unit 1100 may supply power to the piezoelectric element 400 and the control unit 1200.

The mask 1000 according to the second embodiment may include the control unit 1200. The control unit 1200 may control the driving frequency of the piezoelectric element 400 within a set range. In detail, the control unit 1200 may control driving frequencies of the plurality of piezoelectric elements 400 to reduce a driving deviation of each of the plurality of piezoelectric elements 400. Descriptions of the control unit 1200 will be described in more detail with reference to FIGS. 8 and 9 to be described later.

The mask 1000 according to the second embodiment may include a sensing unit 1300. The sensing unit 1300 may sense an output voltage of the piezoelectric element 400. The sensing unit 1300 may sense the output voltage of the piezoelectric element 400 and convert a sensed analog signal into a digital signal. As an example, the sensing unit 1300 may include an ADC driver (analog to digital converter). In addition, the mask 1000 may include a storage unit 1400.

The storage unit 1400 may store a signal sensed by the sensing unit 1300. For example, the storage unit 1400 may store a signal value corresponding to the output voltage of the piezoelectric element 400. The control unit 1200 may control the driving frequency of the piezoelectric element 400 using the signal stored in the storage unit 1400.

Figure 16:
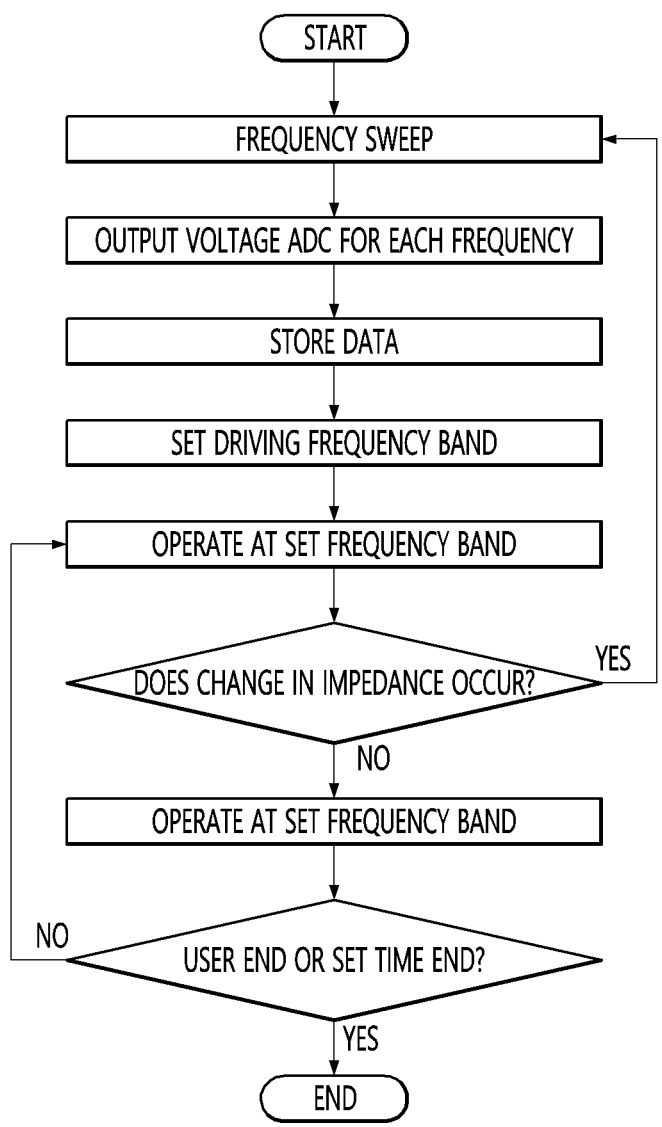
FIG. 16 is a flowchart of an operation of the mask according to the second embodiment.
Figure 17:
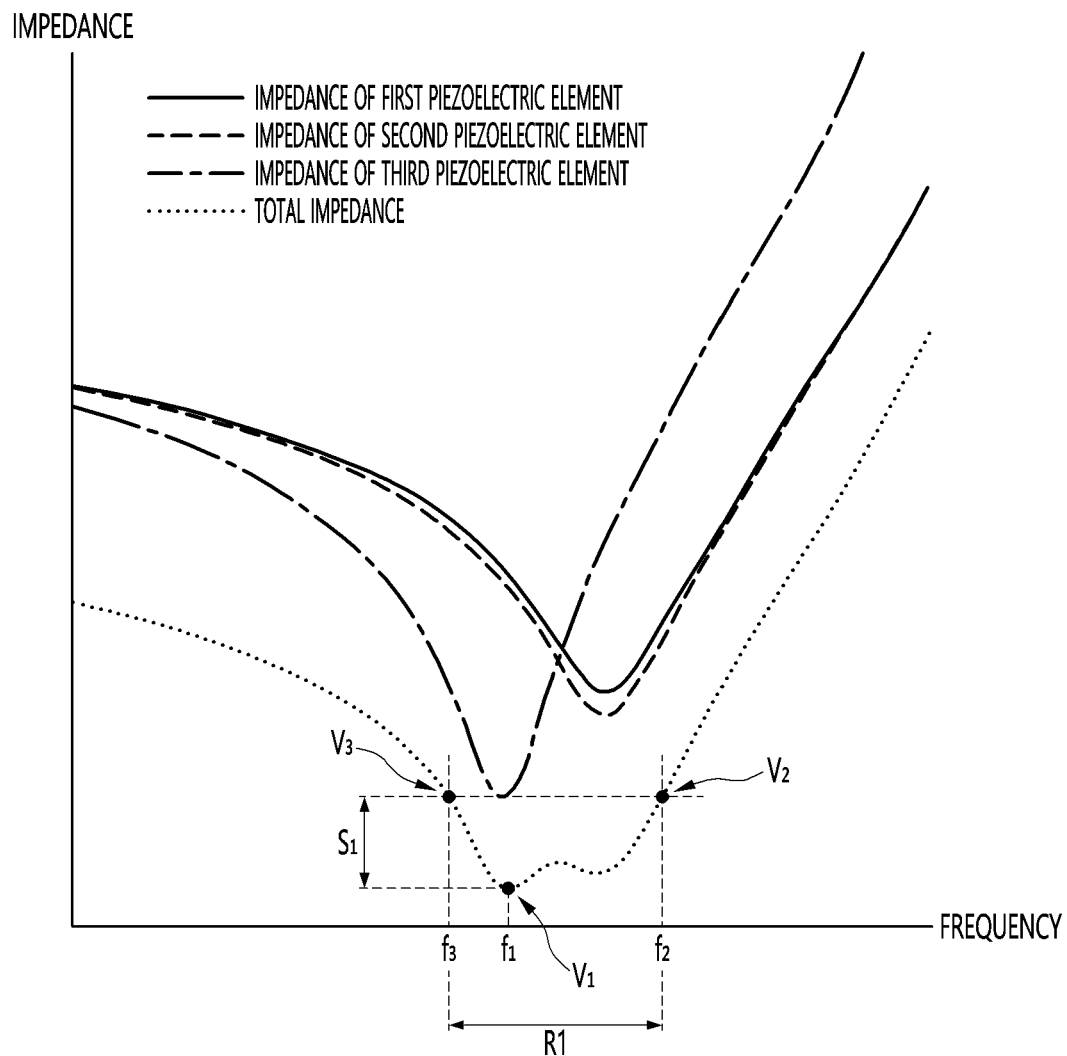
FIG. 17 is a graph illustrating impedance characteristics of a plurality of piezoelectric elements according to the second embodiment.

Referring to FIGS. 15 to 17, the mask 1000 according to the second embodiment may include the control unit 1200 that controls driving frequencies of the plurality of piezoelectric elements 400. In general, the mask 1000 has a resonant frequency fr, and when operating at the resonant frequency fr, ultrasonic efficiency is maximized and an impedance is minimized.

The mask 1000 according to the embodiment may include the plurality of piezoelectric elements 400. In this case, the plurality of piezoelectric elements 400 may have the same or similar impedance characteristics within a set error range. However, while wearing the mask 1000 or the mask 1000 operates, the impedance characteristics of the plurality of piezoelectric elements 400 may be changed.

The impedance characteristic may be a factor that may be changed by an external environment and may be changed by pressure applied to the mask 1000 while the user wears the mask 1000, and may be changed by various factors such as the process by which the mask 1000 is stretchable.

In addition, the impedance characteristic may be changed by a movement of the user wearing while the mask 1000 operates and may be changed depending on an arrangement region of each of the plurality of piezoelectric elements 400. For example, a piezoelectric element 400 disposed in a region corresponding to a relatively curved skin region may have impedance characteristics different from those of a piezoelectric element 400 disposed in a region corresponding to a relatively flat region. Accordingly, there is a problem that the resonant frequency of the piezoelectric element 400 is changed, so that ultrasonic performance is deteriorated, and there is a problem that the ultrasonic efficiency provided to the user's skin is deteriorated.

In order to solve the above-described problem, the mask 1000 according to the embodiment may operate at various driving frequencies. In detail, the control unit 1200 may set a driving frequency band of the plurality of piezoelectric elements 400, and the mask 1000 may operate while changing a driving frequency in the set frequency band.

For example, referring to an operation method of the mask 1000 according to the embodiment, first, the operation method may include supplying power to the mask 1000. The supplying of power may be applying a set driving voltage to the piezoelectric element 400 by the power supply unit 1100.

In addition, the operation method may include sweeping the driving frequency. The sweeping of the frequency may be continuously changing the driving frequencies of the plurality of piezoelectric elements 400. For example, the sweeping may be changing the driving frequencies of the plurality of piezoelectric elements 400 into a set predetermined range from the resonant frequency fr.

In addition, the operation method may include sensing an output voltage for each frequency sensed within the range. The sensing of the output voltage may be sensing an output voltage for each frequency of each of the plurality of piezoelectric elements 400. In the sensing of the output voltage, the sensing unit 1300 may sense the output voltage for each frequency swept in the sweeping. In the step, the sensing unit 1300 may convert a signal of the sensed output voltage. As an example, in the step, the sensing unit 1300 may convert an analog signal corresponding to the sensed output voltage into a digital signal. In addition, the converted signal may be stored in the storage unit 1400.

The control unit 1200 according to the embodiment may control driving frequencies of the plurality of piezoelectric elements 400 based on output voltages for each frequency. For example, the control unit 1200 may control the driving frequencies of the plurality of piezoelectric elements 400 based on the data stored in the storage unit 1400. The control unit 1200 may set a driving frequency band of the plurality of piezoelectric elements 400 based on the data, and the mask 1000 may operate the set frequency band as the driving frequency.

In addition, while the mask 1000 operates, the sweeping of the driving frequency and the sensing of the output voltage for each frequency may be repeatedly operated. In detail, the step may be performed for a short time that the user does not recognize, and the steps may be repeated every set time to continuously sense a change in impedance of the mask 1000.

As an example, the mask 1000 may operate a first frequency band set through the step as the driving frequency. Thereafter, the mask 1000 may perform the sweeping of the driving frequency after a time set in a process of operating in the first frequency band and the sensing of the output voltage for each frequency again. When the change in impedance is not sensed as a result of the step, the mask 1000 may operate until a time at which the first frequency band is set to the driving frequency or until the end time of the user.

On the other hand, when the change in impedance occurs, the process may be repeated in order to set a new frequency band. In detail, in the operation method, the sweeping of the driving frequency and the sensing of the sensed output voltage for each frequency may be performed again, and the control unit 1200 may newly set the driving frequency bands of the plurality of piezoelectric elements 400 based on new data sensed by the sensing unit 1300. Subsequently, the mask 1000 may operate in a newly set driving frequency band, and the control unit 1200 may control the driving frequency by continuously monitoring the change in impedance. The mask 1000 may operate by repeating this process, and may operate until a set time or until the end time of the user. Accordingly, the mask 1000 according to the embodiment may control a continuously changing resonant frequency and a resonance deviation of the piezoelectric element 400.

In more detail, the mask 1000 may include the plurality of piezoelectric elements 400. For example, the plurality of piezoelectric elements 400 may include first to third piezoelectric elements. In this case, the first to third piezoelectric elements may have different impedance characteristics as shown in FIG. 17 due to an external environment or the like. In addition, the total impedance of the mask 1000 may have a form as shown in FIG. 17.

In detail, the mask 1000 may include a first driving frequency f1 defined as the resonant frequency fr from a total impedance curve. The resonant frequency fr may be a frequency corresponding to the lowest output voltage in the sensing of the above-described output voltage. Here, the lowest output voltage may be defined as a first voltage V1.

That is, the first voltage V1 may be an output voltage of a frequency having a minimum impedance magnitude in the impedance curve. In detail, the first voltage V1 may be the lowest output voltage among output voltages of the first to third piezoelectric elements. The first voltage V1 may be a minimum voltage value among output voltages in a first region R1 to be described later.

In addition, the mask 1000 may include a second driving frequency f2 defined as a frequency different from the first driving frequency f1.

The second driving frequency f2 may be a frequency corresponding to a specific voltage sensed in the sensing of the output voltage described above. In detail, the second driving frequency f2 may be a frequency corresponding to a second voltage V2 having a predetermined voltage difference from the first voltage V1 in the total impedance curve. Here, the predetermined voltage difference may be defined as a first voltage difference S1. The second voltage V2 may refer to an output voltage value greater than the first voltage V1 by the first voltage difference S1.

The total impedance curve may include a point defined as a first point. The first point may be a point corresponding to the second voltage V2 and the second driving frequency f2. That is, the first point may be a point at which a voltage difference occurs from the first voltage V1 by the first voltage difference S1. The first point may be a point having an impedance greater than a point corresponding to the first driving frequency f1 in the total impedance curve. The second driving frequency f2, which is a frequency corresponding to the first point, may be a frequency higher than the first driving frequency f1.

In addition, the mask 1000 may include a third driving frequency f3 defined as a frequency different from the first driving frequency f1.

The third driving frequency f3 may be a frequency corresponding to a specific voltage sensed in the sensing of the output voltage described above. In detail, the third driving frequency f3 may be a frequency corresponding to a third voltage V3 having the first voltage difference S1 from the first voltage V1 in the total impedance curve. The third voltage V3 may be the same output voltage value as the second voltage V2.

The total impedance curve may include a point defined as a second point. The second point may be a point corresponding to the third voltage V3 and the third driving frequency f3. That is, the second point may be a point at which a voltage difference occurs from the third voltage V3 by the first voltage difference S1. The second point may be a point having an impedance greater than a point corresponding to the resonant frequency fr, for example, the first driving frequency f1 in the total impedance curve. The third driving frequency f3, which is a frequency corresponding to the second point, may be a frequency lower than the first driving frequency f1.

The control unit 1200 according to the second embodiment may set a driving frequency band defined as the first region R1. In detail, the control unit 1200 may set the first region R1 defined as the driving frequency band of the plurality of piezoelectric elements 400 (first to third piezoelectric elements in FIG. 9). The control unit 1200 may set the first region R1 from impedances of the first and second points that are different from the output voltage of the resonant frequency f1 by the first voltage difference S1. The mask 1000 may operate the frequency band of the first region R1 as the driving frequency.

In this case, the first voltage difference S1 may be about 2.5 decibels (db) to about 3.5 decibels (db). In detail, the first voltage difference S1 may be about 2.8 decibels to about 3.2 decibels.

When the first voltage difference S1 is less than about 2.5 decibels, a range of the first region R1 set by the control unit 1200 may be narrow. That is, there may be no significant difference in the driving frequency band in which the piezoelectric element 400 may be variable compared to the first driving frequency f1. Accordingly, the effect of reducing a deviation of ultrasonic energy of each of the plurality of piezoelectric elements 400 may be insignificant.

In addition, when the first voltage difference S1 exceeds about 3.5 decibels, the range of the first region R1 set by the control unit 1200 may be too large. That is, there may be a too large difference in the driving frequency band in which the plurality of piezoelectric elements 400 may be variable compared to the first driving frequency f1. Accordingly, the deviation of ultrasonic energy of each of the plurality of piezoelectric elements 400 may be greater. Preferably, the first voltage difference S1 may be about 3 decibels in consideration of variations in operating temperatures and ultrasonic power of the plurality of piezoelectric elements 400.

The mask 1000 according to the second embodiment may operate while changing the driving frequency in the first region R1. In detail, the plurality of piezoelectric elements 400 may operate while changing driving frequencies in the first region R1. The plurality of piezoelectric elements 400 may operate while continuously changing their frequency for a predetermined time. That is, the plurality of piezoelectric elements 400 may operate while sweeping the frequency in the first region R1.

For example, the plurality of piezoelectric elements 400 may operate at an interval set in the first region R1. The set interval may be about 0.5 kHz to about 2 kHz. In detail, the set interval may be about 0.8 kHz to about 1.2 kHz. That is, the plurality of piezoelectric elements 400 may operate while the driving frequencies vary at intervals of about 0.8 kHz to about 1.2 kHz in the frequency band of the first region R1.

When the interval is less than about 0.5 kHz, a gap of the interval is too narrow, and thus a high clock control unit may be required in order to secure a frequency resolution. Accordingly, power consumption and manufacturing costs of the mask 1000 may increase. In addition, when the interval exceeds about 2 kHz, there is no significant difference from a frequency deviation of the plurality of piezoelectric elements 400, and thus the frequency variable effect may be insignificant. Preferably, the set interval may be about 1 kHz in consideration of power consumption, ultrasonic deviation, and the like.

In addition, the plurality of piezoelectric elements 400 may operate at a dwell time set in the first region R1. Here, the dwell time may refer to an operation time at a specific frequency. The set dwell time may be about 0.1 seconds to 3 seconds. In detail, the set dwell time may be about 0.2 seconds to about 2.5 seconds. Preferably, the set dwell time may be about 0.5 seconds to about 2 seconds in consideration of reducing the ultrasonic deviation and heating characteristics of the plurality of piezoelectric elements 400.

That is, the plurality of piezoelectric elements 400 may operate for about 0.2 seconds to 2.5 seconds at a specific frequency selected in the first region R1, and then the frequency may be varied by a set interval. As an example, the set interval may be 1 kHz and the dwell time may be 1 second, and the second driving frequency f2 and the third driving frequency f3 may be 333 kHz and 325 kHz, respectively. In this case, the plurality of piezoelectric elements 400 may operate at a start frequency of 325 kHz for 1 second. Thereafter, the driving frequencies of the plurality of piezoelectric elements 400 may be varied by the interval and may operate at a frequency of 326 kHz for 1 second.

The plurality of piezoelectric elements 400 may operate in an up-sweep method in which a driving frequency changes from a low frequency to a high frequency according to the dwell time set in the frequency band of the first region R1. In addition, the plurality of piezoelectric elements 400 may operate in a down-sweep method in which a driving frequency changes from a high frequency to a low frequency in the frequency band of the first region R1. In addition, the plurality of piezoelectric elements 400 may operate by mixing the up-sweep method and the down-sweep method in the first region R1. That is, the driving frequencies of the plurality of piezoelectric elements 400 may change and operate in at least one of the up-sweep method and the down-sweep method in the first region R1.

Accordingly, the mask 1000 according to the second embodiment may maximize ultrasonic efficiency. In detail, as the mask 1000 operates while changing the driving frequency in the set frequency band, it is possible to compensate for a change in impedance component and a change in resonant frequency of a specific piezoelectric element 400 caused by the external environment, thereby maximizing the ultrasonic performance.

In addition, the mask 1000 may monitor the first driving frequency f1 defined as the resonant frequency fr and a resonance deviation of the plurality of piezoelectric elements 400 while repeating the above-described steps in the operation process. Accordingly, the user may receive uniform ultrasonic energy while using the mask 1000.

In addition, the mask 1000 may control the heating characteristics of the plurality of piezoelectric elements 400. In detail, the control unit 1200 may set the driving frequency band in consideration of the resonance deviation of the plurality of piezoelectric elements 400, and accordingly, it is possible to prevent the specific piezoelectric element 400 having a changed impedance component from excessively heating. Therefore, it is possible to prevent the user from getting a burn such as a low temperature burn due to heat generated by an abnormal operation of the specific piezoelectric element 400 during the operation of the mask 1000.

Hereinafter, the operation and effect of the mask according to the second embodiment will be described in more detail through Example and Comparative Example.

FIG. 18 is data comparing ultrasonic power of a mask according to Example and Comparative Example.

Comparative Example FIG. 18(A)

An ultrasonic mask was manufactured by disposing a plurality of piezoelectric elements having a cylindrical shape inside a silicone elastomer and spaced apart from each other, and disposing wirings for applying power to the piezoelectric elements inside the silicone elastomer.

Thereafter, a driving frequency of the ultrasonic mask was fixed at 328 kHz, operated for 10 seconds (s), and the ultrasonic intensity of the plurality of piezoelectric elements operating for 10 seconds was measured.

Example FIG. 18(B)

In the same manner as in Comparative Example, an ultrasonic mask in which a plurality of piezoelectric elements were disposed inside a silicone elastomer was manufactured.

Thereafter, a driving frequency of the ultrasonic mask was set in a range of 325 kHz to 333 kHz and operated for 10 minutes. At this time, the driving frequency of the mask was operated while varying at an interval of 1 kHz and a dwell time of 0.5 seconds in the set frequency band, and ultrasonic intensity of the plurality of piezoelectric elements operating for 10 seconds was measured.

In the data of FIG. 18, a plurality of circles expressed by yellow refers to a plurality of piezoelectric elements. In addition, the stronger the yellow color is expressed in the data may refer that the ultrasonic intensity is strong.

Referring to (A) of FIG. 18, it can be seen that the plurality of piezoelectric elements have different colors (brightness, saturation). That is, it can be seen that the plurality of piezoelectric elements of the mask according to the Comparative Example have different ultrasonic intensities. In detail, as the mask operates at a fixed frequency, it can be seen that the ultrasonic performance is relatively deteriorated in some piezoelectric elements of which impedance components are changed due to the external environment. Accordingly, when the user uses the mask, it may be difficult to effectively supply ultrasonic energy to a skin region corresponding to the piezoelectric element having deteriorated performance.

On the other hand, referring to (B) of FIG. 18, it can be seen that the plurality of piezoelectric elements have similar colors (brightness, saturation). That is, it can be seen that the plurality of piezoelectric elements of the mask according to the embodiment have similar ultrasonic intensity to each other. In detail, the mask according to the embodiment may operate while the driving frequency sweeps in the set frequency band, and accordingly, the ultrasonic performance of some piezoelectric elements of which impedance components are changed due to the external environment may be corrected. Accordingly, when the user uses the mask, the ultrasonic energy may be uniformly supplied to the entire region of the skin to be used.

Therefore, the mask 1000 according to the second embodiment may maximize the ultrasonic efficiency. That is, the mask 1000 may compensate for a distorted resonant frequency by analyzing the change in the impedance component generated by the external environment, thereby maximizing the ultrasonic performance and controlling the heating characteristics of the plurality of piezoelectric elements 400.

Hereinafter, a mask according to a third embodiment will be described with reference to FIGS. 19 to 23.

Figure 19:
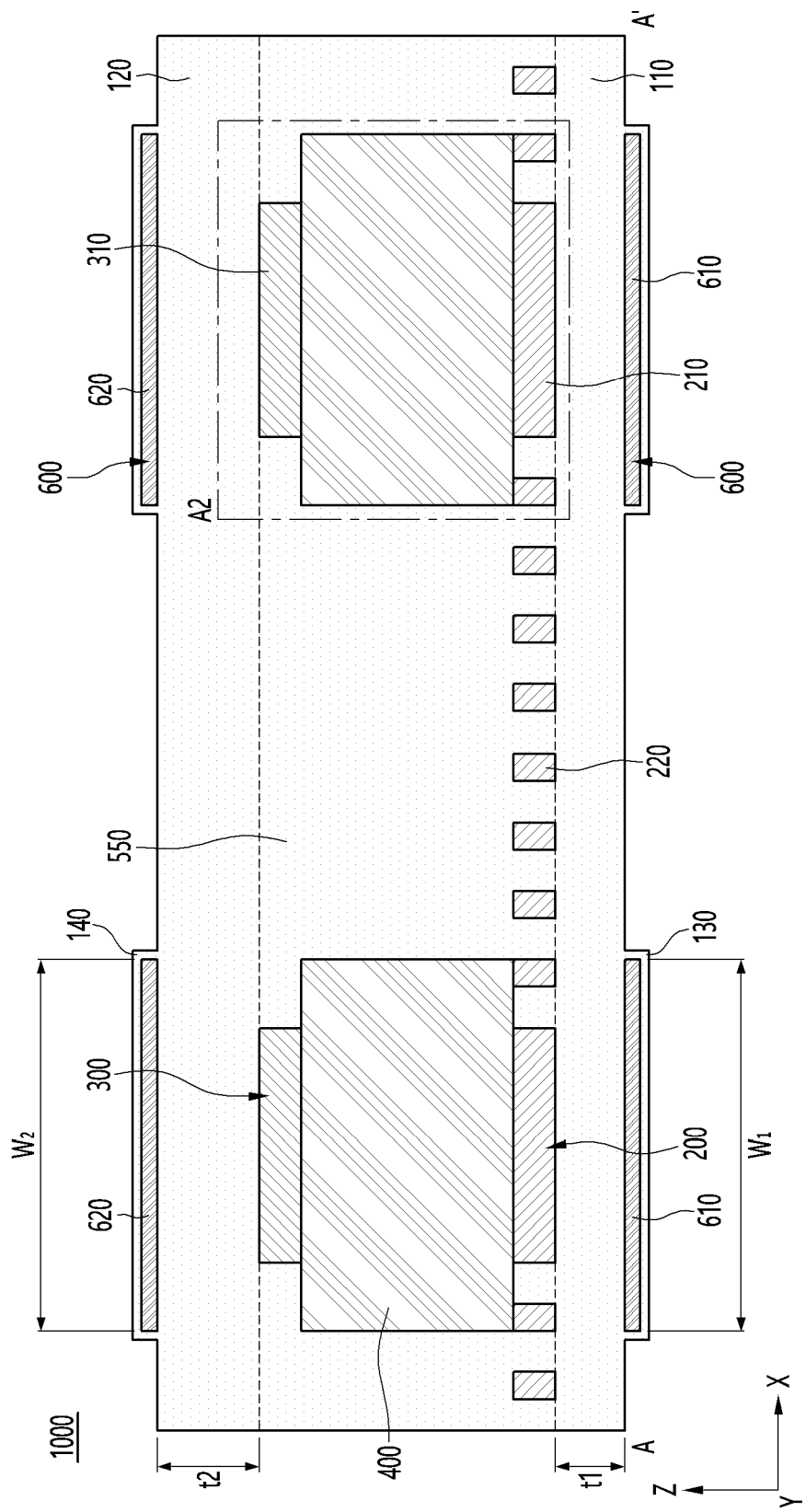
FIG. 19 is a cross-sectional view of a mask according to a third embodiment illustrating a cross-section taken along line A-A' of FIG. 4.

Referring to FIG. 19, the mask 1000 according to the third embodiment may include a barrier layer 600. The barrier layer 600 may maintain the thickness of the mask 1000 when the mask 1000 is elastically deformed, and may protect internal components of the mask 1000.

The barrier layer 600 may be disposed on at least one of the first wiring 200 and the second wiring 300. The barrier layer 600 may be disposed in a region corresponding to the piezoelectric element 400 in the vertical direction.

The barrier layer 600 may include at least one of a metal and a polymer material. For example, the barrier layer 600 may include at least one of polypropylene (PP), polyethylene (PE), polycarbonate (PC), polyimide, polyethylene terephthalate (PET), and polyetherether ketone (PEEK).

The barrier layer 600 may include a material having an elastic modulus lower than that of at least one selected from among the first base layer 110, the second base layer 120, and the protective layer 550. For example, the barrier layer 600 may be about 80% or less of the elastic modulus of the first base layer 110, the second base layer 120, and the protective layer 550. In detail, the elastic modulus of the barrier layer 600 may be about 70% or less of the elastic modulus of the components 110, 120, and 550.

A thickness of the barrier layer 600 may be smaller than a thickness of each of the first and second base layers 110 and 120. For example, the thickness of the barrier layer 600 may be about 1 μm to about 100 μm. When the thickness of the barrier layer 600 is less than about 1 μm, deterioration of the deformation characteristics of the components 110, 120, and 550 by the barrier layer 600 may be insignificant. In addition, when the thickness of the barrier layer 600 exceeds about 100 μm, the overall thickness of the mask 1000 may be increased, and elastic deformation characteristics may be deteriorated, so that adhesion to the user's skin may be deteriorated.

The barrier layer 600 may include a first barrier layer 610 disposed on the first base layer 110. The first barrier layer 610 may be disposed on the other surface opposite to one surface of the first base layer 110. The first barrier layer 610 may be disposed under the first base layer 110 based on the vertical direction.

The first barrier layer 610 may be disposed in a third base layer 130. As an example, the first barrier layer 610 may be disposed in the third base layer 130 disposed on the other surface of the first base layer 110.

The third base layer 130 may include a material harmless to the human body. The third base layer 130 may include a material having softness and elasticity. As an example, the third base layer 130 may include a silicone elastomer that is relatively light, may minimize irritation upon contact with the user's skin, and has a predetermined elasticity.

The third base layer 130 may be disposed to surround the first barrier layer 610. Accordingly, the third base layer 130 may prevent the first barrier layer 610 from being exposed to the outside. In addition, the third base layer 130 may include the same material as the first base layer 110. The third base layer 130 may be integrally formed with the first base layer 110. Accordingly, the third base layer 130 may have an improved bonding force with the first base layer 110.

The first barrier layer 610 may be disposed in a region corresponding to the piezoelectric element 400. In detail, the first barrier layer 610 may overlap the piezoelectric element 400 in the vertical direction. In more detail, a center of the first barrier layer 610 may overlap the center of the lower surface of the piezoelectric element 400 in the vertical direction. In addition, the first barrier layer 610 may overlap the first connection portion 210 in the vertical direction. In detail, the center of the first barrier layer 610 may overlap the center of the first connection portion 210 in the vertical direction.

A width of the first barrier layer 610 may be the same as or different from the width of the piezoelectric element 400. In detail, a width w1 of the first barrier layer 610 in the horizontal direction may be about 0.8 times to about 2 times the width of the lower surface of the piezoelectric element 400.

For example, when the width w1 of the first barrier layer 610 in the horizontal direction is less than about 0.8 times the width of the lower surface of the piezoelectric element 400, the reliability of the first wiring 200 may be deteriorated. In detail, the first barrier layer 610 may not deteriorate the elastic deformation characteristics of the protective layer 550 corresponding to a boundary between the first connection portion 210 and the first extension portion 220. Accordingly, a disconnection between the first connection portion 210 and the first extension portion 220 may be caused during repeated elastic deformation. In addition, when the width w1 in the horizontal direction of the first barrier layer 610 exceeds about twice the width of the lower surface of the piezoelectric element 400, the elastic deformation characteristic of the mask 1000 may be deteriorated. Accordingly, adhesion characteristics between the user and the mask 1000 may be deteriorated. Therefore, it is preferable that the width w1 of the first barrier layer 610 in the horizontal direction satisfies the above-described range in consideration of the reliability of the first wiring 200 and reflective characteristics of the first base layer 110.

More preferably, the width w1 in the horizontal direction of the first barrier layer 610 may be about 1 time to about 1.5 times the width of the lower surface of the piezoelectric element 400. Accordingly, the first wiring 200 may have improved reliability, and the first base layer 110 may effectively reflect the ultrasonic energy.

The barrier layer 600 may include a second barrier layer 620 disposed on the second base layer 120. The second barrier layer 620 may be disposed on the other surface opposite to one surface of the second base layer 120. The second barrier layer 620 may be disposed above the second base layer 120 based on the vertical direction.

The second barrier layer 620 may be disposed in a fourth base layer 140. As an example, the second barrier layer 620 may be disposed in the fourth base layer 140 disposed on the other surface of the second base layer 120.

The fourth base layer 140 may include a material harmless to the human body. The fourth base layer 140 may include a material having softness and elasticity. As an example, the fourth base layer 140 may include a silicone elastomer that is relatively light, may minimize irritation upon contact with the user's skin, and has a predetermined elasticity.

The fourth base layer 140 may be disposed to surround the second barrier layer 620. Accordingly, the fourth base layer 140 may prevent the second barrier layer 620 from being exposed to the outside. In addition, the fourth base layer 140 may include the same material as the second base layer 120. The fourth base layer 140 may be integrally formed with the second base layer 120. Accordingly, the fourth base layer 140 may have an improved bonding force with the second base layer 120.

The second barrier layer 620 may be disposed in a region corresponding to the piezoelectric element 400. In detail, the second barrier layer 620 may overlap the piezoelectric element 400 in the vertical direction. In more detail, a center of the second barrier layer 620 may overlap a center of the upper surface of the piezoelectric element 400 in the vertical direction. In addition, the second barrier layer 620 may overlap the second connection portion 310 in the vertical direction. In detail, the center of the second barrier layer 620 may overlap the center of the second connection portion 310 in the vertical direction.

A width of the second barrier layer 620 may be the same as or different from the width of the piezoelectric element 400. In detail, a width w1 of the second barrier layer 620 in the horizontal direction may be about 0.8 times to about 2 times the width of the upper surface of the piezoelectric element 400.

For example, when the width w2 of the second barrier layer 620 in the horizontal direction is less than about 0.8 times the width of the upper surface of the piezoelectric element 400, the reliability of the second wiring 300 may be degraded. In detail, the second barrier layer 620 may not deteriorate the elastic deformation characteristics of the protective layer 550 corresponding to a boundary between the second connection portion 310 and the second extension portion 320. Accordingly, a disconnection between the second connection portion 310 and the second extension portion 320 may be caused during repeated elastic deformation. In addition, when the width w2 in the horizontal direction of the second barrier layer 620 exceeds about twice the width of the lower surface of the piezoelectric element 400, the elastic deformation characteristic of the mask 1000 may be deteriorated. Accordingly, the adhesion characteristics between the user and the mask 1000 may be deteriorated. Therefore, it is preferable that the width w2 in the horizontal direction of the second barrier layer 620 satisfies the above-described range in consideration of the reliability of the second wiring 300 and the transmission characteristics of the second base layer 120.

More preferably, the width w2 of the second barrier layer 620 in the horizontal direction may be about 1 time to 1.5 times the width of the lower surface of the piezoelectric element 400. In addition, the width w2 of the second barrier layer 620 in the horizontal direction may be the same as the width w1 of the first barrier layer 610 in the horizontal direction. Accordingly, the second wiring 300 may have improved reliability, and the second base layer 120 may effectively transmit the ultrasonic energy.

In addition, the second barrier layer 620 may include the same material as the first barrier layer 610. Alternatively, the second barrier layer 620 may include a material different from the first barrier layer 610. For example, the first barrier layer 610 may include a material capable of reflecting the ultrasonic energy emitted from the piezoelectric element 400. In addition, the second barrier layer 620 may include a material capable of transmitting the ultrasonic energy emitted from the piezoelectric element 400. Accordingly, the thickness of the first base layer 110 and the second base layer 120 may be reduced, and a slimmer mask may be provided.

The mask 1000 according to the third embodiment may be elastically deformed due to the user's wearing or the like. In this case, the first base layer 110, the second base layer 120, and the protective layer 550 may be elastically deformed. In particular, when the mask 1000 is elastically deformed, the thicknesses t1 and t2 of the first base layer 110 and the second base layer 120 may be changed. For example, a predetermined stress may be applied to the mask 1000 in order for the user to adhere the mask 1000 to the skin, and the thicknesses t1 and t2 of the first base layer 110 and the second base layer 120 may be smaller compared to before the stress is applied. Accordingly, ultrasonic energy reflection characteristic of the first base layer 110 and ultrasonic energy transmission characteristic of the second base layer 120 may be changed.

However, the mask 1000 according to the third embodiment may deteriorate elastic deformation characteristics of some regions of the first base layer 110, the second base layer 120, and the protective layer 550. In detail, the embodiment may include the first barrier layer 610 and the second barrier layer 620 disposed in the region corresponding to the piezoelectric element 400 in the vertical direction. Accordingly, elastic deformation characteristics of the first base layer 110, the second base layer 120, and the protective layer 550 on which the barrier layers 610 and 620 are disposed may be deteriorated. In detail, it is possible to minimize changes in the thicknesses t1 and t2 of each of the first and second base layers 110 and 120 in the region in which the barrier layers 610 and 620 are disposed.

Therefore, the mask 1000 according to the third embodiment may be elastically deformed effectively according to a shape of the user's skin to adhere to the skin. In addition, even when the mask 1000 is elastically deformed due to the user's wearing or the like, the ultrasonic energy may be effectively reflected and transmitted to be provided to the user. In addition, even though the user repeatedly uses and wears the mask 1000, the first wiring 200 and the second wiring 300 may have improved reliability.

In addition, although not shown in the drawings, the first and second barrier layers 610 and 620 may have a structure in which a hole is formed. As an example, when viewed in a plane, the first and second barrier layers 610 and 620 may have a ring shape in which the hole is formed in a central region. In this case, a plane area of the first barrier layer 610 may be about 10% or more of the area of the lower surface of the piezoelectric element 400. In addition, a plane area of the second barrier layer 620 may be about 10% or more of the area of the upper surface of the piezoelectric element 400.

Figure 20:
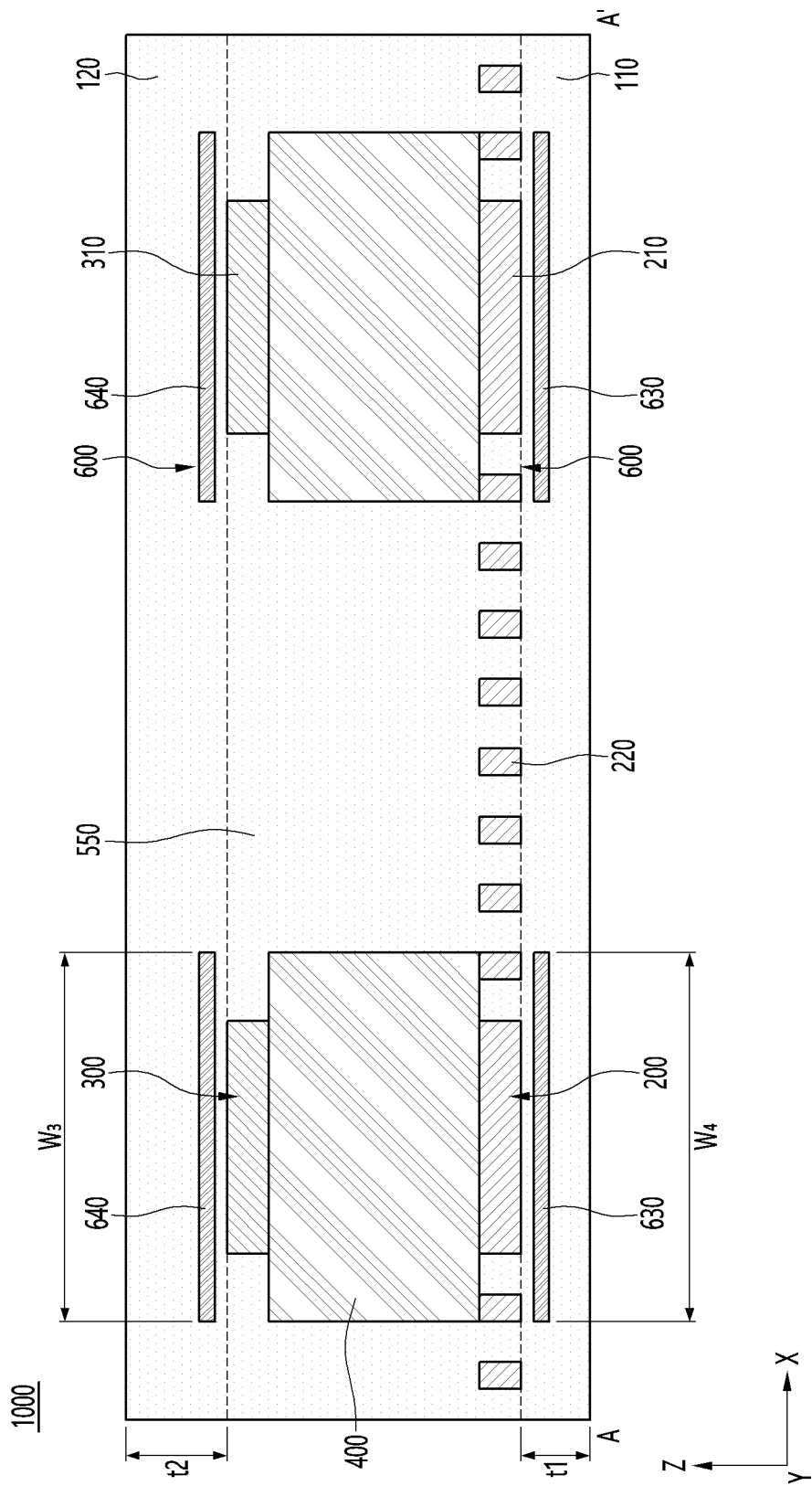
FIG. 20 is a cross-sectional view of the mask according to the third embodiment illustrating another cross-section taken along line A-A' of FIG. 4.
Figure 21:
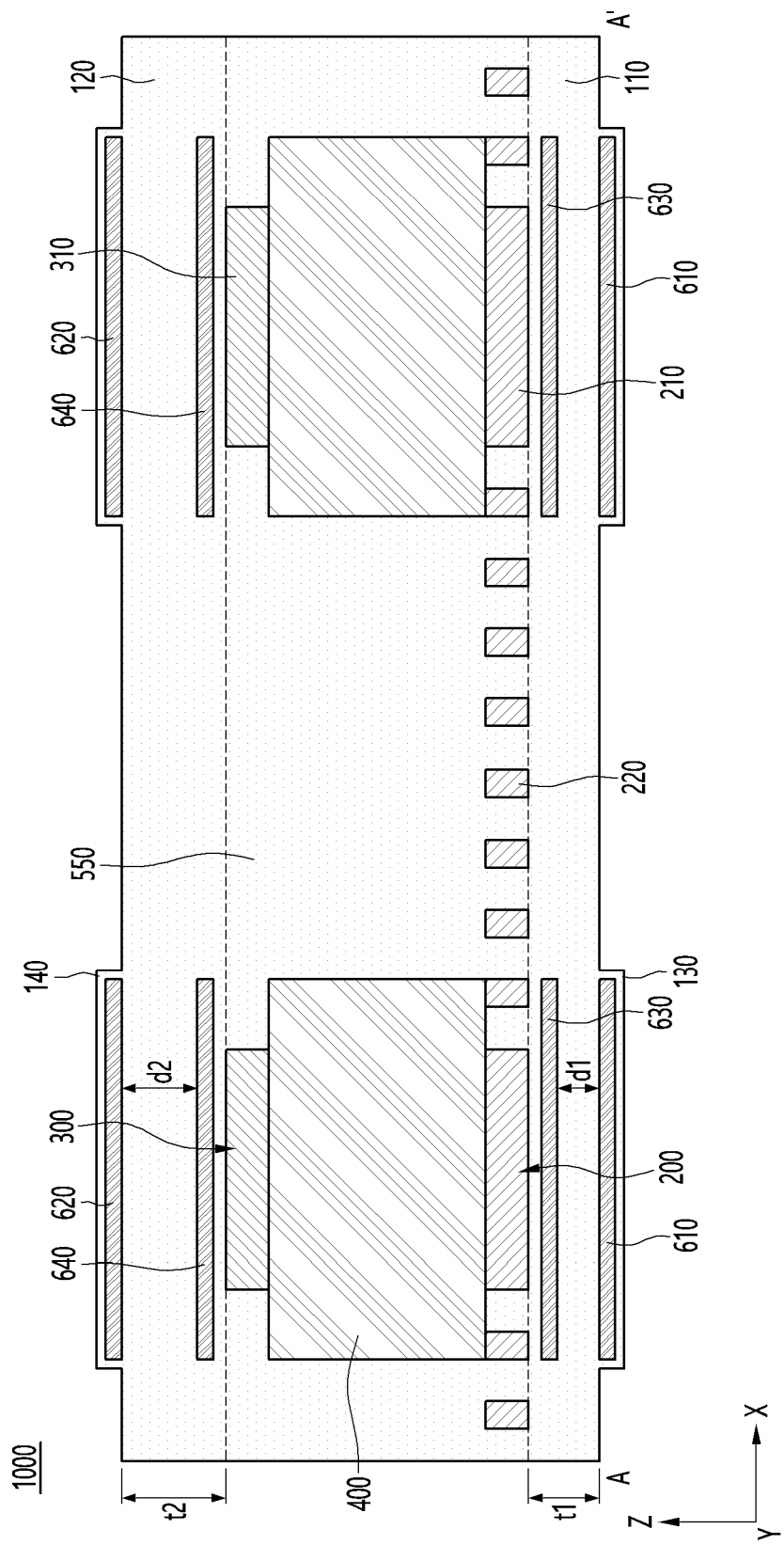
FIG. 21 is a cross-sectional view of the mask according to the third embodiment illustrating still another cross-sectional taken along line A-A' of FIG. 4.

FIGS. 20 and 21 are cross-sectional views of the mask according to the third embodiment illustrating another cross-sectional taken along line A-A' of FIG. 4.

Referring to FIG. 20, the barrier layer 600 may include a third barrier layer 630 and a fourth barrier layer 640.

The third barrier layer 630 may be disposed on the first wiring 200. The third barrier layer 630 may be spaced apart from the first wiring 200. For example, the third barrier layer 630 may be spaced apart from the first wiring 200 in the vertical direction and may be disposed under the first wiring 200. That is, the third barrier layer 630 may be closer to the other surface of the mask 1000 than the first wiring 200.

The third barrier layer 630 may be disposed in the first base layer 110. The third barrier layer 630 may be inserted and disposed in the first base layer 110. The first base layer 110 may be disposed to surround a circumference of the third barrier layer 630.

The third barrier layer 630 may be disposed in a region corresponding to the piezoelectric element 400. In detail, the third barrier layer 630 may overlap the piezoelectric element 400 in the vertical direction. In more detail, a center of the third barrier layer 630 may overlap the center of the lower surface of the piezoelectric element 400 in the vertical direction. In addition, the third barrier layer 630 may overlap the first connection portion 210 in the vertical direction. In detail, the center of the third barrier layer 630 may overlap the center of the first connection portion 210 in the vertical direction.

A width of the third barrier layer 630 may be the same as or different from the width of the piezoelectric element 400. In detail, a width of the third barrier layer 630 in the horizontal direction may be about 0.8 times to about 2 times the width of the lower surface of the piezoelectric element 400.

For example, when the width of the third barrier layer 630 in the horizontal direction is less than about 0.8 times the width of the lower surface of the piezoelectric element 400, the reliability of the first wiring 200 may be deteriorated. In detail, the third barrier layer 630 may not deteriorate the elastic deformation characteristics of the protective layer 550 corresponding to the boundary between the first connection portion 210 and the first extension portion 220. Accordingly, a disconnection between the first connection portion 210 and the first extension portion 220 may be caused during repeated elastic deformation. In addition, when the width of the third barrier layer 630 in the horizontal direction exceeds about twice the width of the lower surface of the piezoelectric element 400, the elastic deformation characteristics of the mask 1000 may be deteriorated. Accordingly, the adhesion characteristics between the user and the mask 1000 may be deteriorated. Therefore, it is preferable that the width of the third barrier layer 630 in the horizontal direction satisfies the above-described range in consideration of the reliability of the first wiring 200 and the reflection characteristics of the first base layer 110.

More preferably, the width of the third barrier layer 630 in the horizontal direction may be about 1 time to about 1.5 times the width of the lower surface of the piezoelectric element 400. Accordingly, the first wiring 200 may have improved reliability, and the first base layer 110 may effectively reflect the ultrasonic energy.

The fourth barrier layer 640 may be disposed on the second wiring 300. The fourth barrier layer 640 may be spaced apart from the second wiring 300. For example, the fourth barrier layer 640 may be spaced apart from the second wiring 300 in the vertical direction and disposed under the second wiring 300. That is, the fourth barrier layer 640 may be adjacent to one surface of the mask 1000 more than the second wiring 300.

The fourth barrier layer 640 may be disposed in the second base layer 120. The fourth barrier layer 640 may be inserted and disposed in the second base layer 120. The second base layer 120 may be disposed to surround a circumference of the fourth barrier layer 640.

The fourth barrier layer 640 may be disposed in a region corresponding to the piezoelectric element 400. In detail, the fourth barrier layer 640 may overlap the piezoelectric element 400 in the vertical direction. In more detail, a center of the fourth barrier layer 640 may overlap the center of the upper surface of the piezoelectric element 400 in the vertical direction. In addition, the fourth barrier layer 640 may overlap the second connection portion 310 in the vertical direction. In detail, the center of the fourth barrier layer 640 may overlap the center of the second connection portion 310 in the vertical direction.

A width of the fourth barrier layer 640 may be the same as or different from the width of the piezoelectric element 400. In detail, a width of the fourth barrier layer 640 in the horizontal direction may be about 0.8 times to about 2 times the width of the upper surface of the piezoelectric element 400.

For example, when the width of the fourth barrier layer 640 in the horizontal direction is less than about 0.8 times the width of the upper surface of the piezoelectric element 400, the reliability of the second wiring 300 may be deteriorated. In detail, the fourth barrier layer 640 may not deteriorate the elastic deformation characteristics of the protective layer 550 corresponding to the boundary between the second connection portion 310 and the second extension portion 320. Accordingly, a disconnection between the second connection portion 310 and the second extension portion 320 may be caused during repeated elastic deformation. In addition, when the width of the fourth barrier layer 640 in the horizontal direction exceeds about twice the width of the upper surface of the piezoelectric element 400, the elastic deformation characteristic of the mask 1000 may be deteriorated. Accordingly, the adhesion characteristics between the user and the mask 1000 may be deteriorated. Therefore, it is preferable that the width of the fourth barrier layer 640 in the horizontal direction satisfies the above-described range in consideration of the reliability of the second wiring 300 and the reflection characteristics of the second base layer 120.

More preferably, the width of the fourth barrier layer 640 in the horizontal direction may be about 1 time to about 1.5 times the width of the upper surface of the piezoelectric element 400. Accordingly, the second wiring 300 may have improved reliability, and the second base layer 120 may effectively transmit the ultrasonic energy.

In addition, the fourth barrier layer 640 may include the same material as the third barrier layer 630. Alternatively, the fourth barrier layer 640 may include a material different from that of the third barrier layer 630. For example, the third barrier layer 630 may include a material capable of reflecting the ultrasonic energy emitted from the piezoelectric element 400. In addition, the fourth barrier layer 640 may include a material capable of transmitting the ultrasonic energy emitted from the piezoelectric element 400. Accordingly, the thickness of the first base layer 110 and the second base layer 120 may be reduced, and a slimmer mask may be provided.

Referring to FIG. 21, the barrier layer 600 may include a plurality of barrier layers. For example, the barrier layer 600 may include the first barrier layer 610 disposed on the first base layer 110, the second barrier layer 620 disposed on the second base layer 120, the third barrier layer 630 disposed in the first base layer 110, and the fourth barrier layer 640 disposed in the second base layer 120.

The first barrier layer 610 and the third barrier layer 630 may overlap the piezoelectric element 400 in the vertical direction. In detail, the centers of each of the first barrier layer 610 and the third barrier layer 630 may overlap the center of the lower surface of the piezoelectric element 400 in the vertical direction.

The first barrier layer 610 and the third barrier layer 630 may be spaced apart in the vertical direction. For example, the first barrier layer 610 and the third barrier layer 630 may be spaced apart by a distance defined as a first interval d1. The first interval d1 may be about 5 μm to about 1000 μm. In detail, the first interval d1 may be about 10 μm to about 1000 μm. When the first interval d1 is less than about 5 μm, the elastic deformation characteristics of the first base layer 110 and the protective layer 550 corresponding to the barrier layers 610 and 630 may be rapidly deteriorated. Accordingly, the elastic deformation characteristics of the mask 1000 may be deteriorated, so that it may be difficult to effectively adhere to the user's skin. In addition, when the first interval d1 exceeds about 1000 μm, the thickness of the first base layer 110 may be increased, so that the overall thickness of the mask 1000 may be increased.

The first barrier layer 610 and the third barrier layer 630 may include the same material. As an example, the first barrier layer 610 and the third barrier layer 630 may include at least one of a metal and a polymer material. The first barrier layer 610 and the third barrier layer 630 may include a material capable of reflecting the ultrasonic energy emitted from the piezoelectric element 400.

The second barrier layer 620 and the fourth barrier layer 640 may overlap the piezoelectric element 400 in the vertical direction. In detail, the centers of each of the second barrier layer 620 and the fourth barrier layer 640 may overlap the center of the upper surface of the piezoelectric element 400 in the vertical direction.

The second barrier layer 620 and the fourth barrier layer 640 may be spaced apart in the vertical direction. For example, the second barrier layer 620 and the fourth barrier layer 640 may be spaced apart by a distance defined as a second interval d2. The second interval d2 may be about 5 μm to about 1000 μm. In detail, the second interval d2 may be about 5 μm to about 1000 μm. When the second interval d2 is less than about 5 μm, the elastic deformation characteristics of the second base layer 120 and the protective layer 550 corresponding to the barrier layers 620 and 640 may be rapidly deteriorated. Accordingly, the elastic deformation characteristics of the mask 1000 may be deteriorated, so that it may be difficult to effectively adhere to the user's skin. In addition, when the second interval d2 exceeds about 1000 μm, the thickness of the second base layer 120 may be increased, so that the overall thickness of the mask 1000 may be increased.

The second barrier layer 620 and the fourth barrier layer 640 may include the same material. As an example, the second barrier layer 620 and the fourth barrier layer 640 may include at least one of a metal and a polymer material. The second barrier layer 620 and the fourth barrier layer 640 may include a material capable of transmitting the ultrasonic energy emitted from the piezoelectric element 400.

In addition, the first and third barrier layers 610 and 630 may include the same material as the second and third barrier layers 620 and 640. Alternatively, the first and third barrier layers 610 and 630 may include a material different from those of the second and third barrier layers 620 and 640. As an example, the first and third barrier layers 610 and 630 may include a material capable of reflecting the ultrasonic energy, and the second and fourth barrier layers 620 and 640 may include a material capable of transmitting the ultrasonic energy. Accordingly, the thickness of the first base layer 110 and the second base layer 120 may be reduced, and a slimmer mask may be provided.

In addition, the mask 1000 according to the embodiment includes a plurality of barrier layers 610, 620, 630, and 640, so that it is possible to have more improved reliability, and it is possible to maximize efficiency of the ultrasonic energy provided in the direction of one surface of the mask 1000.

Figure 22:
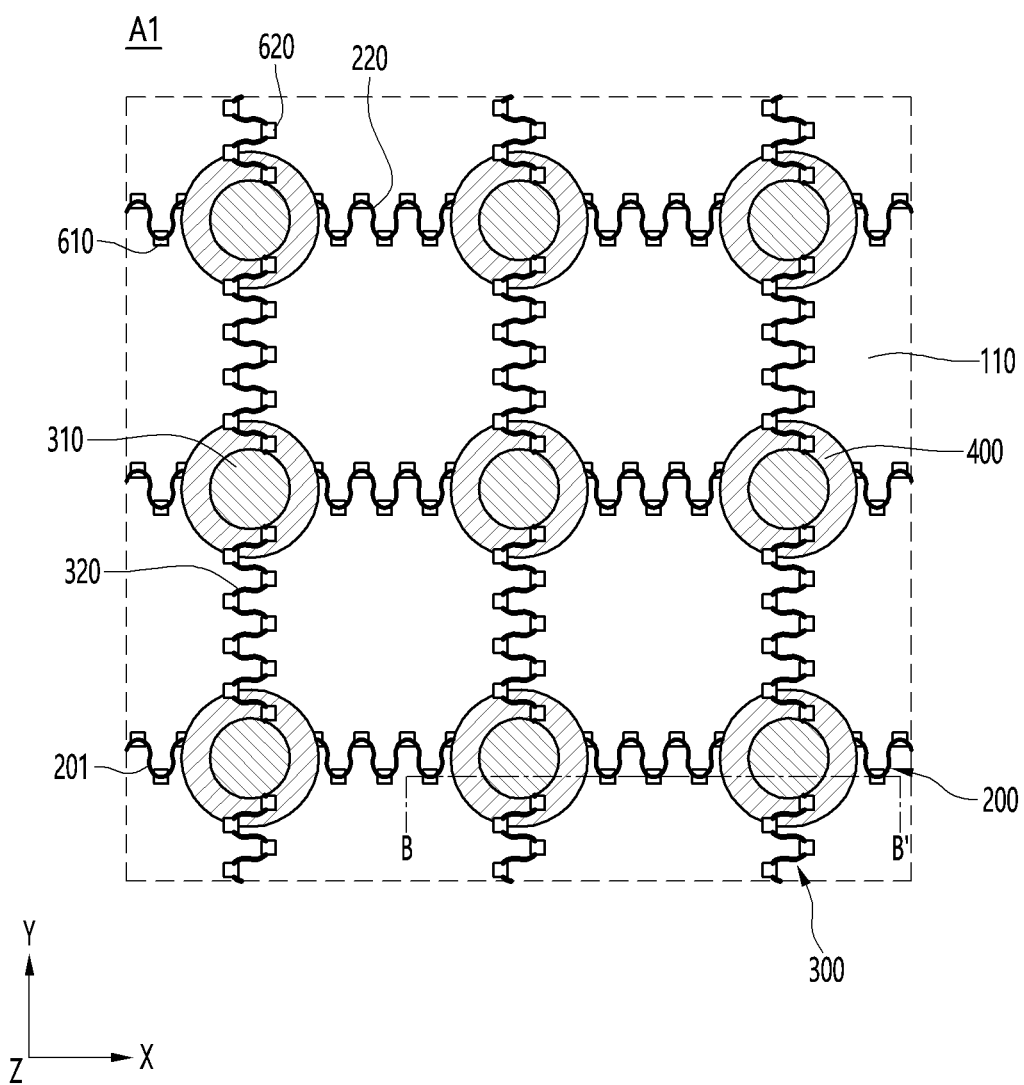
FIG. 22 is a top view of the mask according to the third embodiment illustrating the top view of the region A1 in FIG. 1.
Figure 23:
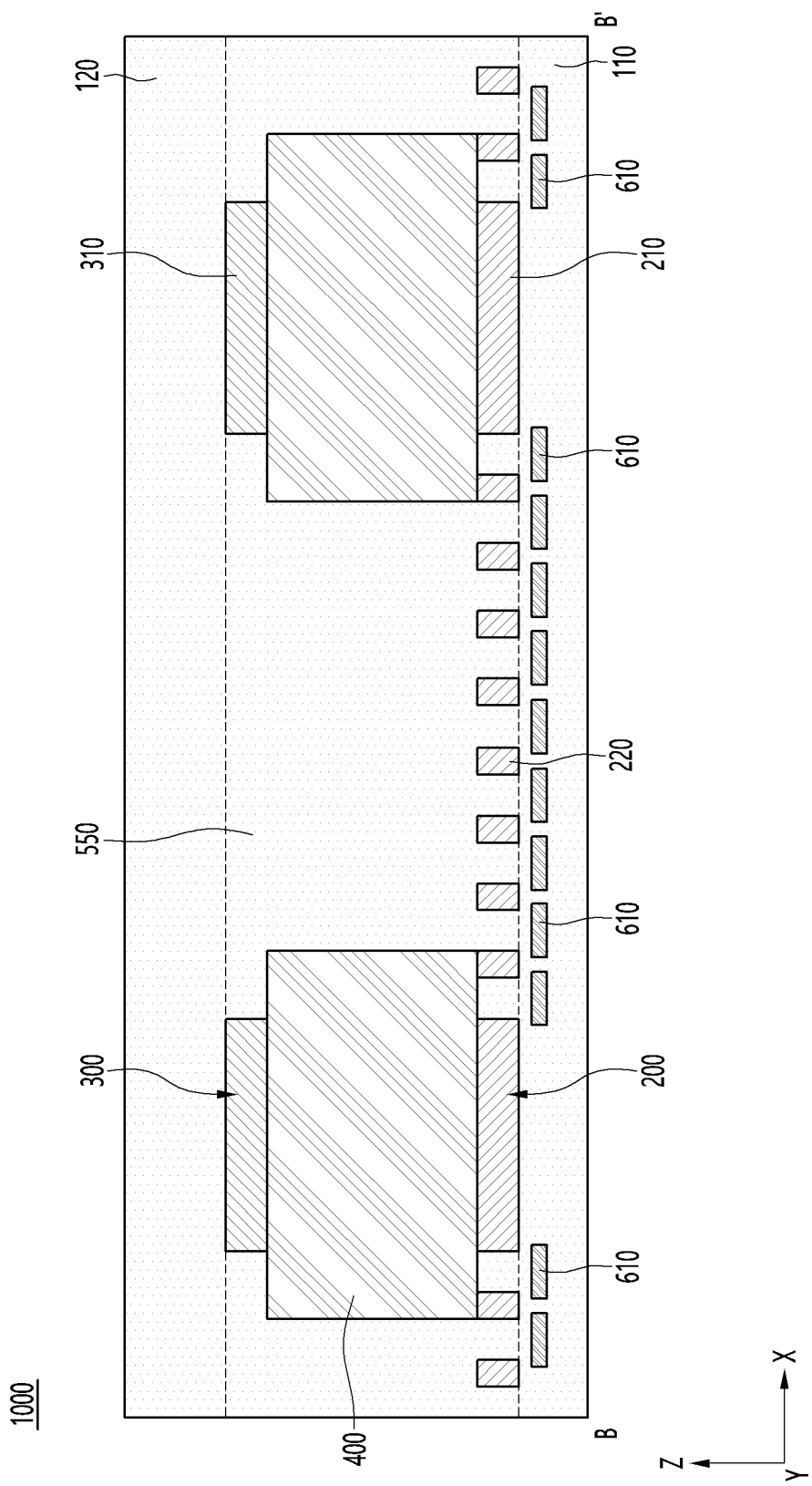
FIG. 23 is a cross-sectional view of the mask according to the third embodiment illustrating a cross section taken along line B-B' of FIG. 19.
Figure 24:
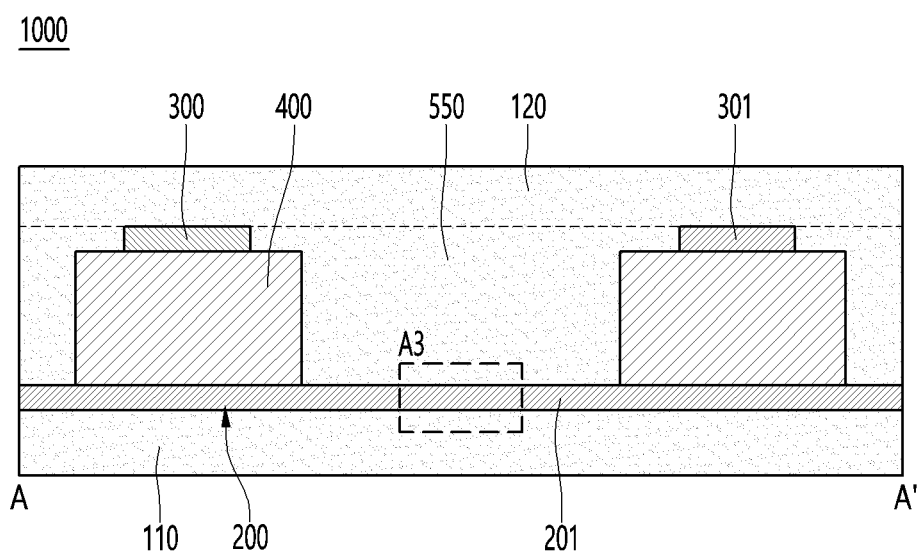
FIG. 24 is a cross-sectional view taken along line C-C' of FIG. 3.

Referring to FIGS. 22 and 23, the barrier layer 600 may be disposed on at least one of the first wiring 200 and the second wiring 300. The barrier layer 600 may be disposed in a region corresponding to the piezoelectric element 400 and the wirings 200 and 300.

The barrier layer 600 may include the third barrier layer 630 disposed on the first wiring 200 as shown in FIG. 7. The third barrier layer 630 may be disposed in a region corresponding to the piezoelectric element 400. In detail, a part of the third barrier layer 630 may overlap the piezoelectric element 400 in the vertical direction. In addition, the third barrier layer 630 may be disposed in a region that does not overlap in the vertical direction and is spaced apart from the center of the lower surface of the piezoelectric element 400.

In addition, the third barrier layer 630 may be disposed in a region corresponding to the first wiring 200. For example, a part of the third barrier layer 630 may overlap the first connection portion 210, and another part of the third barrier layer 630 may overlap the first extension portion 220. In detail, the third barrier layer 630 may be disposed in a region vertically overlapping the boundary between the first connection portion 210 and the first extension portion 220.

In addition, the third barrier layer 630 may be disposed in a region corresponding to a bending region of the first extension portion 220. For example, when the first extension portion 220 is provided in a curved shape in which a wavy pattern is repeated as shown in FIG. 9, the third barrier layer 630 may be disposed in a region vertically overlapping the bending region in which the extension direction is changed.

In addition, the barrier layer 600 may include the fourth barrier layer 640 disposed on the second wiring 300 as shown in FIG. 7. The fourth barrier layer 640 may be disposed in a region corresponding to the piezoelectric element 400. In detail, a part of the fourth barrier layer 640 may vertically overlap the piezoelectric element 400. In addition, the fourth barrier layer 640 may be disposed in a region that does not vertically overlap and is spaced apart from the center of the lower surface of the piezoelectric element 400.

In addition, the fourth barrier layer 640 may be disposed in a region corresponding to the second wiring 300. For example, a part of the fourth barrier layer 640 may overlap the second connection portion 310, and another part of the fourth barrier layer 640 may overlap the second extension portion 320. In detail, the fourth barrier layer 640 may be disposed in a region vertically overlapping the boundary between the second connection portion 310 and the second extension portion 320.

In addition, the fourth barrier layer 640 may be disposed in a region corresponding to a bending region of the second extension portion 320. For example, when the second extension portion 320 is provided in a curved shape in which a wavy pattern is repeated as shown in FIG. 9, the fourth barrier layer 640 may be disposed in a region vertically overlapping the bending region in which the extension direction is changed.

Each of the third and fourth barrier layers 630 and 640 may have a width in the horizontal direction smaller than that of the piezoelectric element 400. In detail, each of the third and fourth barrier layers 630 and 640 may be about 80% or less of the width of the piezoelectric element 400 in the horizontal direction.

Accordingly, the wirings 200 and 300 of the mask 1000 may have improved reliability. In detail, when the mask 1000 is elastically deformed, the wirings 200 and 300 may also be deformed. In this case, the third and fourth barrier layers 630 and 640 may be disposed on the boundary between the connection portions 210 and 310 and bending regions of the extension portions 220 and 320 that have relatively low reliability among the wirings 200 and 300. Therefore, the barrier layers 630 and 640 may deteriorate elastic deformability of a region in which the barrier layers 630 and 640 are disposed, thereby minimizing stress applied to the wirings 200 and 300.

In addition, although not shown in the drawings, each of the first and second barrier layers 610 and 620 may be disposed on a boundary between the first and second wirings 110 and 120 and bending regions like the third and fourth barrier layers 630 and 640, but the embodiment is not limited thereto.

Hereinafter, a mask according to a fourth embodiment will be described with reference to FIGS. 24 to 32.

Referring to FIGS. 25 to 32, at least one of the first wiring 200 and the second wiring 300 according to the embodiment may have a multiple layer structure. As an example, the first wiring 200 and the second wiring 300 may be provided in a multiple layer structure. In detail, the first sub-wiring 201 and the second sub-wiring 301 may be provided in the same multiple layer structure. That is, since the first wiring 200 and the second wiring 300 may have the same structure, the first wiring 200 will be mainly described for convenience of description in the description using FIGS. 6 to 11.

Figure 25:
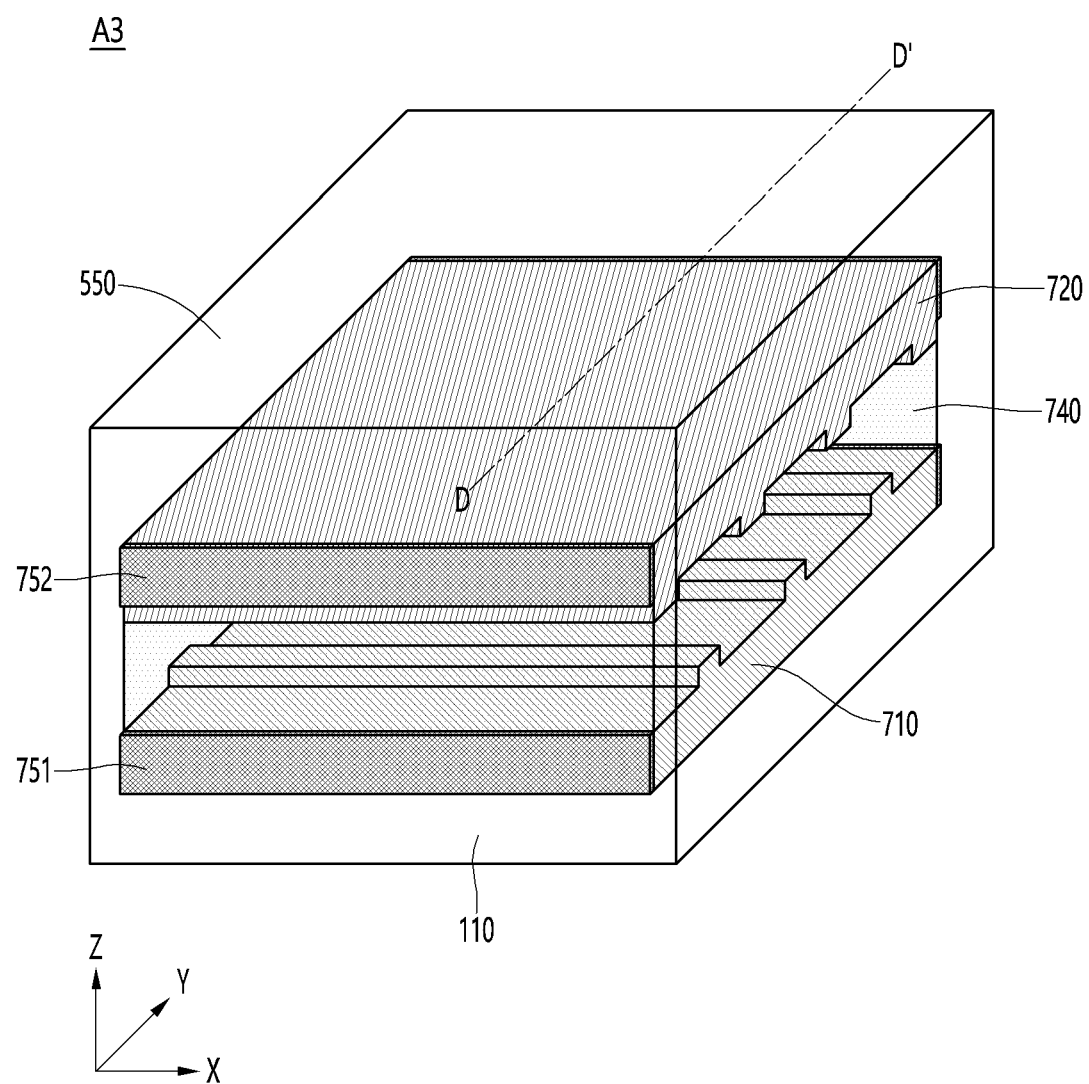
FIG. 25 is an enlarged view of a mask according to a fourth embodiment in which region A3 in FIG. 24 is enlarged.
Figure 26:
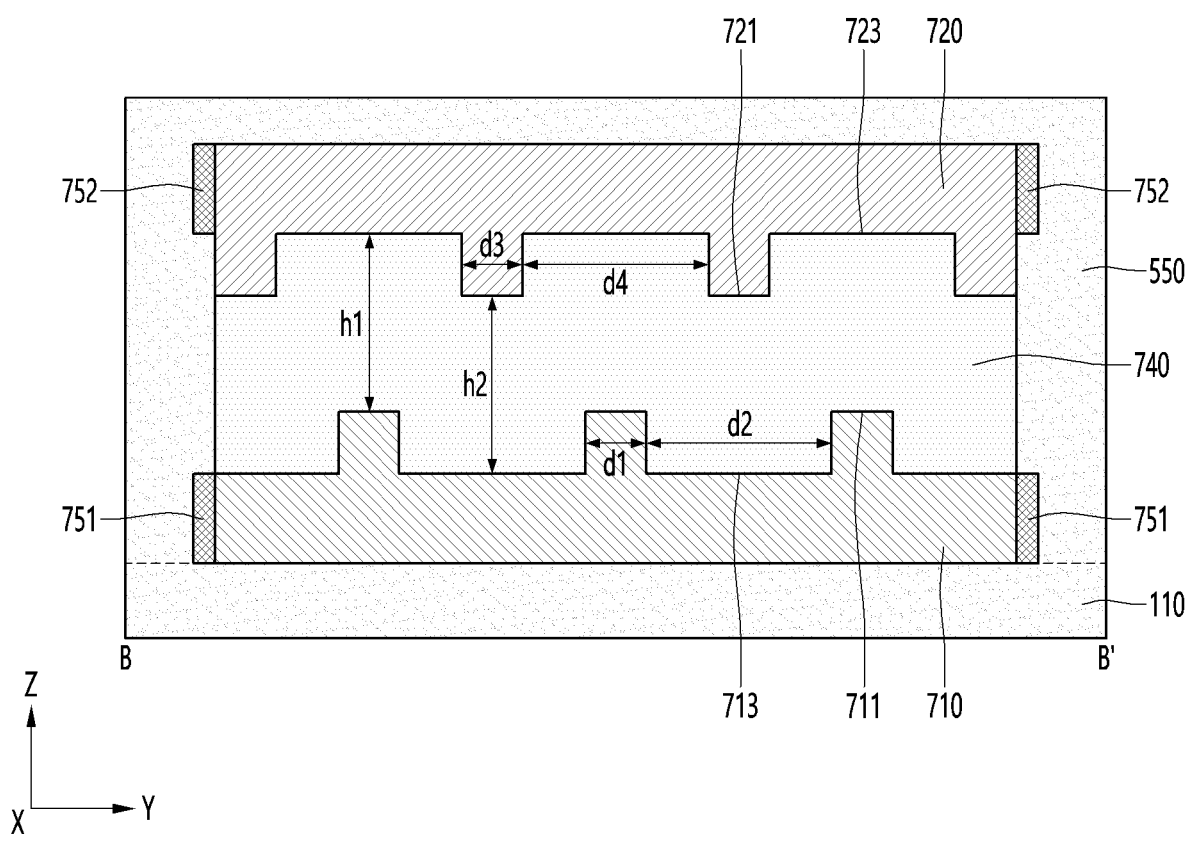
FIG. 26 is a cross-sectional view of the mask according to the fourth embodiment illustrating a cross-section taken along line D-D' of FIG. 25.

Referring to FIGS. 25 and 26, the first wiring 200 may include a first metal layer 710, a second metal layer 720, and a conductive elastic layer 740.

The first metal layer 710 may be disposed on the first base layer 110. The first metal layer 710 may be disposed on one surface of the first base layer 110. The first metal layer 710 may extend in the first direction.

The second metal layer 720 may be disposed on an upper surface of the first metal layer 710. The second metal layer 720 may be spaced apart from the first base layer 110. The second metal layer 720 may extend in the first direction. In addition, the second metal layer 720 may be spaced apart from the first metal layer 710 in the vertical direction (z-axis direction). The second metal layer 720 may be disposed closer to the piezoelectric element 400 than the first metal layer 710.

The second metal layer 720 may have a width in the horizontal direction corresponding to the first metal layer 710. As an example, the width of the second metal layer 720 in the horizontal direction (x-axis and y-axis) may be the same as the width of the first metal layer 710 in the horizontal direction (x-axis and y-axis).

The first metal layer 710 and the second metal layer 720 may include at least one metal of aluminum (Al), copper (Cu), silver (Ag), gold (Au), chromium (Cr), nickel (Ni), molybdenum (Mo), titanium (Ti), and alloys thereof. The first metal layer 710 and the second metal layer 720 may include the same material and may include different materials among the above-described materials.

The conductive elastic layer 740 may be disposed between the first metal layer 710 and the second metal layer 720. The conductive elastic layer 740 may be spaced apart from the first base layer 110 and may extend in the first direction. The conductive elastic layer 740 may be in direct contact with the first metal layer 710 and the second metal layer 720. The conductive elastic layer 740 may be physically and electrically connected to the first metal layer 710 and the second metal layer 720.

The conductive elastic layer 740 may have a width in the horizontal direction corresponding to the first metal layer 710 and the second metal layer 720. As an example, the width of the conductive elastic layer 740 in the horizontal direction (x-axis and y-axis) may be the same as the width of each of the first and second metal layers 710 and 720 in the horizontal direction (x-axis and y-axis).

The conductive elastic layer 740 may include a conductive elastic material. As an example, the conductive elastic layer 740 may include an elastic material such as silicone, a resin, or the like, and may further include a conductive material such as metal particles and carbon to have conductivity. However, the material of the conductive elastic layer 740 is not limited thereto, and the conductive elastic layer 740 may include various materials having elasticity and conductivity.

The first metal layer 710 may include a plurality of first protrusions 711. In detail, the first metal layer 710 may include the plurality of first protrusions 711 disposed on one surface facing the second metal layer 720. The first protrusion 711 may have a shape protruding toward the second metal layer 720.

The plurality of first protrusions 711 may extend in the horizontal direction. For example, each of the plurality of first protrusions 711 may have a width in the y-axis direction defined as a first width d1 and may extend in the x-axis direction. The plurality of first protrusions 711 may be spaced apart from each other. For example, the first protrusions 711 adjacent to each other may be spaced apart in the y-axis direction. In this case, the plurality of adjacent first protrusions 711 may be spaced apart at equivalent intervals.

The first metal layer 710 may include a plurality of first concave portions 713 disposed on one surface thereof. In detail, the first metal layer 710 may include a first concave portion 713 between the plurality of first protrusions 711.

The first concave portion 713 may extend in the horizontal direction. For example, each of the plurality of first concave portions 713 may have a width in the y-axis direction defined as a second width d2 and may extend in the x-axis direction. The plurality of first concave portions 713 may be spaced apart from each other. For example, the first concave portions 713 adjacent to each other may be spaced apart in the y-axis direction. In this case, the plurality of adjacent first concave portions 713 may be spaced apart at equivalent intervals.

Widths of the first protruding portion 711 and the first concave portion 713 may be the same or different from each other. In detail, the first width d1 of the first protrusion 711 may be equal to or smaller than the second width d2 of the first concave portion 713. For example, the first width d1 may be 100% or less of the second width d2. The first width d1 may be about 80% or less of the second width d2.

The second metal layer 720 may include a plurality of second protrusions 721. In detail, the second metal layer 720 may include the plurality of second protrusions 721 disposed on one surface facing the first metal layer 710. The second protrusion 721 may have a shape protruding toward the first metal layer 710.

The plurality of second protrusions 721 may extend in the horizontal direction. For example, each of the plurality of second protrusions 721 may have a width in the y-axis direction defined as a third width d3 and may extend in the x-axis direction. The plurality of second protrusions 721 may be spaced apart from each other. For example, the second protrusions 721 adjacent to each other may be spaced apart in the y-axis direction. In this case, the plurality of adjacent second protrusions 721 may be spaced apart at equivalent intervals.

The second protrusion 721 may be disposed in a region corresponding to the first concave portion 713 of the first metal layer 710. In detail, the second protrusion 721 may overlap the first concave portion 713 based on the vertical direction (z-axis direction), and may be disposed in a region that does not overlap the first protrusion 711.

The second metal layer 720 may include a plurality of second concave portions 723 disposed on one surface thereof. In detail, the second metal layer 720 may include a second concave portion 723 between the plurality of second protrusions 721.

The second concave portion 723 may extend in the horizontal direction. For example, each of the plurality of second concave portions 723 may have a width in the y-axis direction defined as a fourth width d4 and may extend in the x-axis direction. The plurality of second concave portions 723 may be spaced apart from each other. For example, the second concave portions 723 adjacent to each other may be spaced apart in the y-axis direction. In this case, the plurality of adjacent second concave portions 723 may be spaced apart at equivalent intervals.

The second concave portion 723 may be disposed in a region corresponding to the first protrusion 711 of the first metal layer 710. In detail, the second concave portion 723 may overlap the first protrusion 711 based on the vertical direction (z-axis direction), and may be disposed in a region that does not overlap the first concave portion 713.

Widths of the second protrusion 721 and the second concave portion 723 may be the same or different from each other. In detail, the third width d3 of the second protrusion 721 may be equal to or smaller than the fourth width d4 of the second concave portion 723. For example, the third width d3 may be 100% or less of the fourth width d4. The first width d1 may be about 80% or less of the second width d2.

In addition, the first protrusion 711 may have a width equal to or smaller than the second concave portion 723 facing each other, and the second protrusion 721 may have a width equal to or smaller than the first concave portion 713 facing each other. For example, the first width d1 may be about 100% or less of the fourth width d4, and the third width d3 may be about 100% or less of the second width d2. In detail, the first width d1 may be about 80% or less of the fourth width d4, and the third width d3 may be about 80% or less of the second width d2.

An upper surface of the first protrusion 711 may be spaced apart from a lower surface of the second concave portion 723 by a height defined as a first height h1. A lower surface of the first concave portion 713 may be spaced apart from an upper surface of the second protrusion 721 by a height defined as a second height h2. In this case, the first height h1 and the second height h2 may correspond to each other. For example, the first height h1 may be about 1.2 times to about 5 times a height of the first protrusion 711 and/or a depth of the second concave portion 723. In detail, the first height h1 may be about 1.5 times to about 3 times the height of the first protrusion 711 and/or the depth of the second concave portion 723. In addition, the second height h2 may be about 1.2 times to about 5 times a depth of the first concave portion 713 and/or a height of the second protrusion 721. In detail, the second height h2 may be about 1.5 times to about 3 times the depth of the first concave portion 713 and/or the height of the second protrusion 721.

Accordingly, when the first wiring 200 is elastically deformed, it is possible to prevent the first wiring 200 from being damaged by the deformation. For example, when the second protrusion 721 and the first protrusion 711 move in the horizontal direction and/or vertical direction, the first concave portion 713 and the second concave portion 723 may provide a space capable of accommodating the second and first protrusions 721 and 711. Accordingly, when the mask 1000 according to the embodiment is elastically deformed, it is possible to prevent the first and second metal layers 710 and 720 from being damaged by contacting each other.

In addition, as described above, each of the first metal layer 710 and the second metal layer 720 may have a concave-convex structure including the protrusions 711 and 721 and the concave portions 713 and 723, and the first wiring 200 may be effectively deformed by deformation of the conductive elastic layer 740 disposed between the two metal layers 210 and 220. In this case, the conductive elastic layer 740 may have an increased contact area with the two metal layers 210 and 220 and improved bonding force to the two metal layers 210 and 220 due to the concave-convex structure of the two metal layers 210 and 220.

At least one of barrier members 751 and 752 may be disposed on the first wiring 200. For example, the barrier members 751 and 752 may include a first barrier member 751 disposed on the first metal layer 710 and a second barrier member 752 disposed on the second metal layer 720.

The first barrier member 751 may be disposed to be adjacent to the first metal layer 710. The first barrier member 751 may be disposed on an outer surface of the first metal layer 710. As an example, the first barrier member 751 may be disposed on an outer surface extending in the first direction among a plurality of outer surfaces of the first metal layer 710. The first barrier member 751 may extend in the first direction (x-axis direction). The first barrier member 751 may correspond to a length of the first metal layer 710 in the horizontal direction (x-axis direction). The first barrier member 751 may be in direct contact with the outer surface of the first metal layer 710 as shown in the drawing. In addition, although not shown in the drawings, the first barrier member 751 may be spaced apart from the outer surface of the first metal layer 710 at a predetermined interval. In this case, the protective layer 550 may be disposed between the first barrier member 751 and the first metal layer 710.

The second barrier member 752 may be disposed to be adjacent to the second metal layer 720. The second barrier member 752 may be disposed on an outer surface of the second metal layer 720. As an example, the second barrier member 752 may be disposed on an outer surface extending in the second direction among a plurality of outer surfaces of the second metal layer 720. The second barrier member 752 may extend in the first direction (x-axis direction). The second barrier member 752 may correspond to a length of the second metal layer 720 in the horizontal direction (x-axis direction). The second barrier member 752 may be in direct contact with the outer surface of the second metal layer 720 as shown in the drawing. In addition, although not shown in the drawings, the second barrier member 752 may be spaced apart from the outer surface of the second metal layer 720 at a predetermined interval. In this case, the protective layer 550 may be disposed between the second barrier member 752 and the second metal layer 720.

The first barrier member 751 and the second barrier member 752 may include a material having an elastic modulus lower than that of the conductive elastic layer 740. In addition, the first barrier member 751 and the second barrier member 752 may include a material having an elastic modulus lower than that of at least one component selected from the first base layer 110, the second base layer 120, and the protective layer 550. As an example, the first barrier member 751 and the second barrier member 752 may include a metal and a polymer material. In detail, the barrier members 751 and 752 may include at least one of polypropylene (PP), polyethylene (PE), polycarbonate (PC), polyimide, polyethylene terephthalate (PET), and polyetheretherketone (PEEK).

The first and second barrier members 751 and 752 may be about 80% or less of the elastic modulus of the first base layer 110, the second base layer 120, and the protective layer 550. In detail, the elastic modulus of the first and second barrier members 751 and 752 may be about 70% or less of the elastic modulus of the components 110, 120 and 550.

The above-described protective layer 550 may be disposed around the first metal layer 710, the second metal layer 720, the conductive elastic layer 740, and the barrier members 751 and 752. The protective layer 550 may be disposed to surround the components and may be in direct contact with the components. In this case, when the barrier members 751 and 752 are spaced apart from the metal layers 710 and 7220, the protective layer 550 may be disposed between the barrier members 751 and 752 and the metal layers 710 and 720. The protective layer 550 may be disposed to surround the components to prevent the components from being exposed to the outside.

In addition, the first barrier member 751 and the second barrier member 752 may prevent the first metal layer 710 and the second metal layer 720 from being damaged. For example, when stress is applied to the mask 1000 and the mask 1000 is elastically deformed, the first base layer 110, the second base layer 120, and the protective layer 550 may be elastically deformed, and the first wiring 200 may also be deformed together. In this case, the first barrier member 751 may minimize deformation of the first base layer 110 and the protective layer 550 adjacent to the first metal layer 710, and the second barrier member 752 may minimize deformation of the second base layer 120 and the protective layer 550 adjacent to the second metal layer 720.

That is, when the mask 1000 is elastically deformed, the conductive elastic layer 740 of the first wiring 200 may be elastically deformed by external stress, and the first metal layer 710 and the second metal layer 720 may minimize the deformation by the first barrier member 751 and the second barrier member 752. Therefore, the first wiring 200 may be elastically deformed and simultaneously, may have improved reliability while effectively maintaining conductivity against external stress.

When the mask 1000 according to the fourth embodiment is elastically deformed by external stress, a shape of the first wiring 200 will be described in more detail with reference to FIGS. 27 to 30.

Referring to FIGS. 27 to 30, the mask 1000 according to the fourth embodiment may be elastically deformed by stress applied from the outside.

Figure 27:
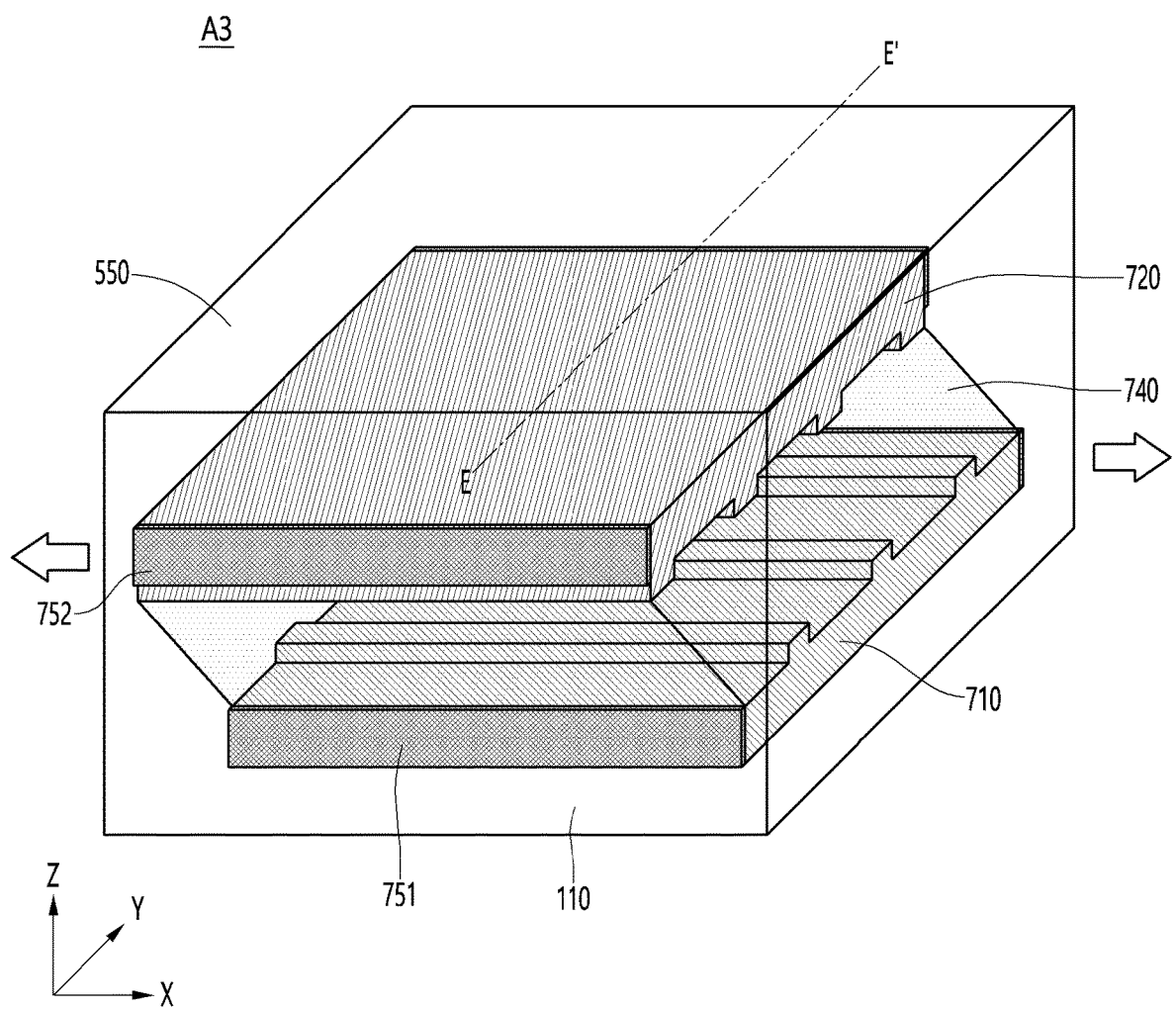
FIG. 27 is a view illustrating an example in which stress is applied to an electrode of FIG. 25 in an x-axis direction.
Figure 28:
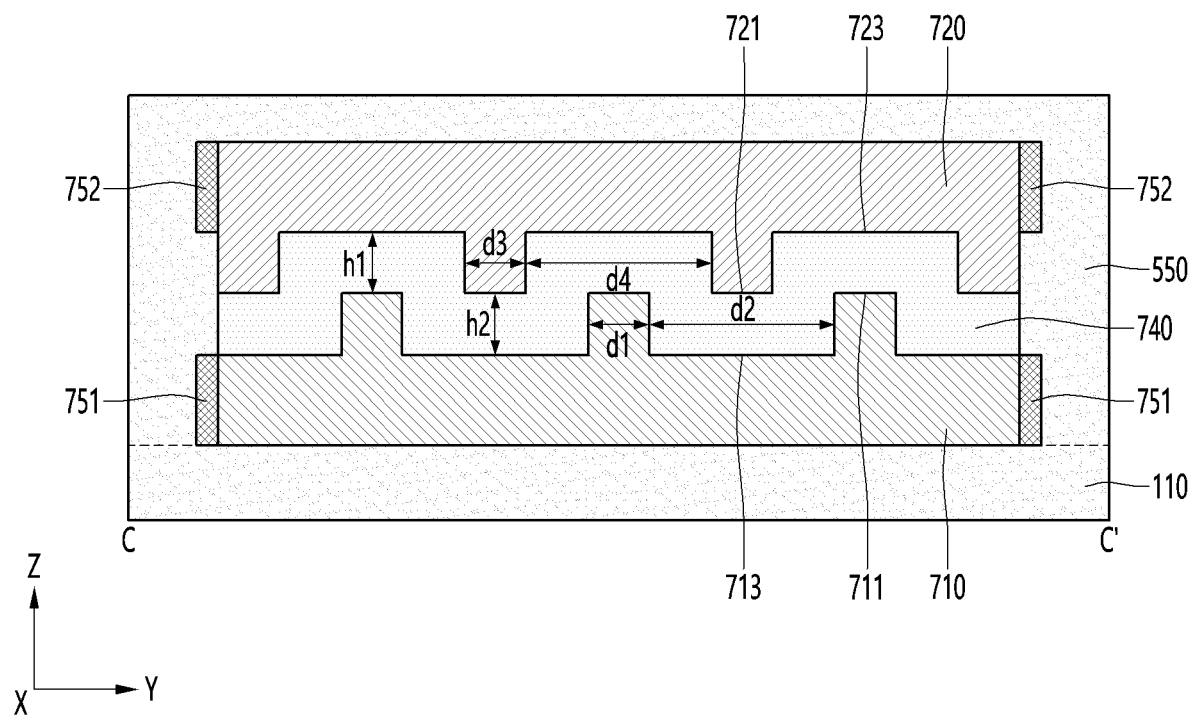
FIG. 28 is a cross-sectional view of the mask according to the fourth embodiment illustrating a cross section taken along line E-E' of FIG. 27.

Referring to FIGS. 27 and 28, the mask 1000 may be elastically deformed in the x-axis and/or -x-axis directions. As an example, when stress is applied to the mask 1000 in the x-axis direction, the conductive elastic layer 740 may be elastically deformed in the x-axis direction. In this case, when the conductive elastic layer 740 is viewed from the side, the conductive elastic layer 740 may have a parallelogram shape as shown in FIG. 8.

That is, the first base layer 110, the second base layer 120, and the protective layer 550 may be elastically deformed by the stress. In addition, the conductive elastic layer 740 may be elastically deformed by the stress, and the first metal layer 710 and/or the second metal layer 720 may move in the x-axis direction. In detail, the first protrusion 711 or the second protrusion 721 may move in the x-axis direction overlapping the second concave portion 723 or the first concave portion 713.

In addition, as the conductive elastic layer 740 is elastically deformed, a distance between the first metal layer 710 and the second metal layer 720 may be decreased. That is, the first height h1 and the second height h2 may be decreased compared to before the elastic deformation (FIGS. 26 and 27). Accordingly, the distance between the first and second metal layers 710 and 720 may be closer, and a resistance value between the first and second metal layers 710 and 720 may be decreased.

Figure 29:
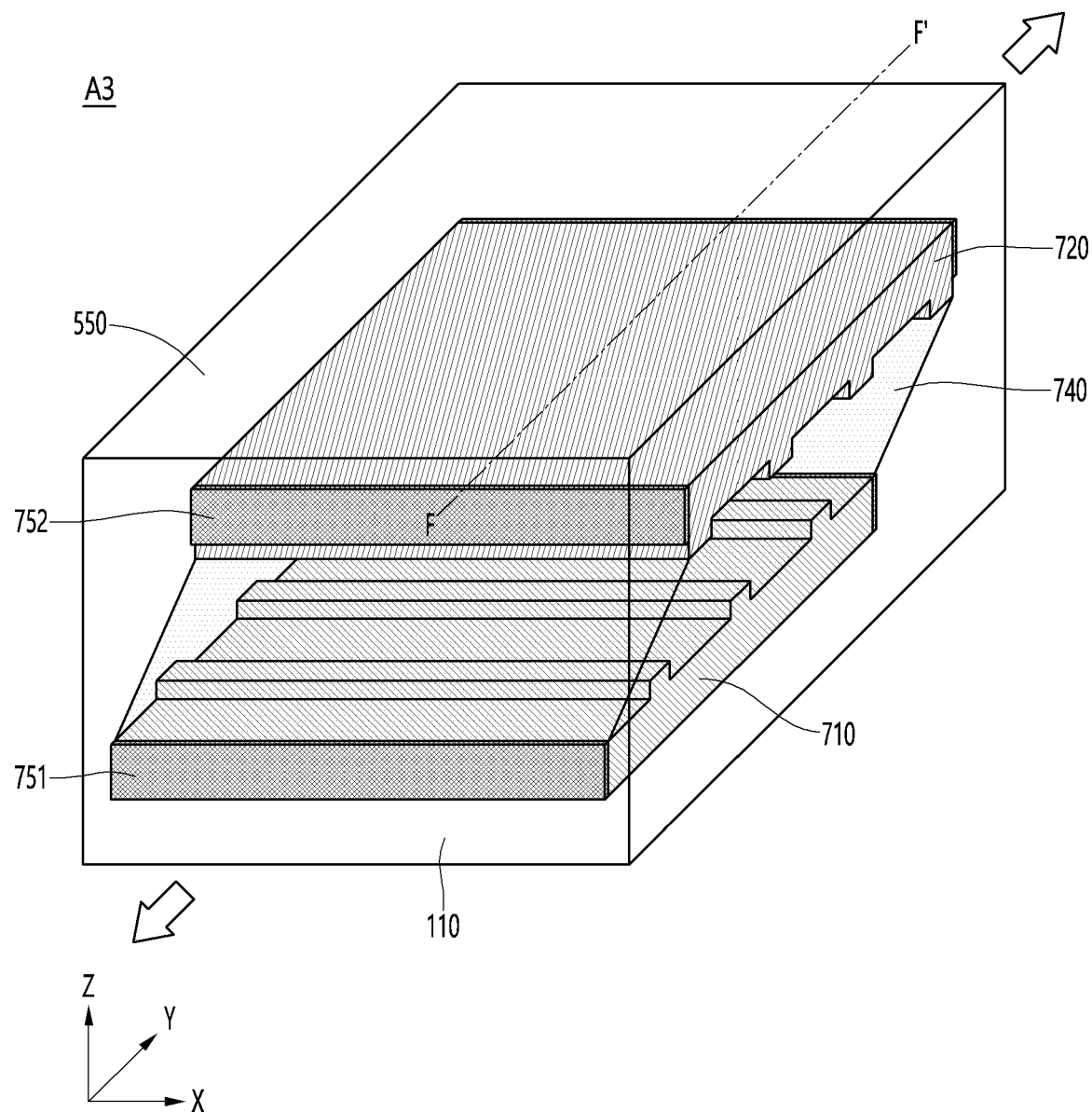
FIG. 29 is a view illustrating an example in which stress is applied to the electrode of FIG. 25 in a y-axis direction.
Figure 30:
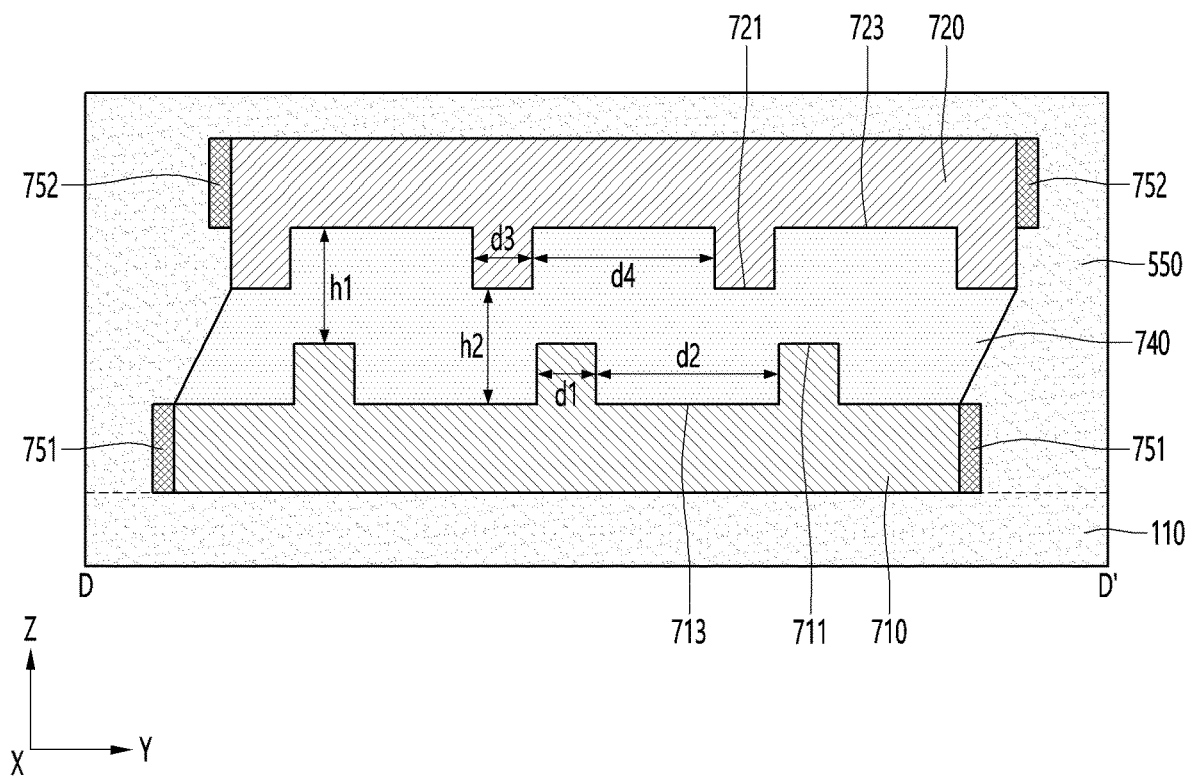
FIG. 30 is a cross-sectional view of the mask according to the fourth embodiment illustrating a cross-section taken along line F-F' of FIG. 29.

Referring to FIGS. 29 and 30, the mask 1000 may be elastically deformed in the y-axis and/or -y-axis directions. As an example, when stress is applied to the mask 1000 in the y-axis direction, the conductive elastic layer 740 may be elastically deformed in the y-axis direction. In this case, when the conductive elastic layer 740 is viewed from the side, the conductive elastic layer 740 may have a rectangular shape as shown in FIG. 29.

That is, the first base layer 110, the second base layer 120, and the protective layer 550 may be elastically deformed by the stress. In addition, the conductive elastic layer 740 may be elastically deformed by the stress, and the first metal layer 710 or the second metal layer 720 may move in the y-axis direction. In detail, the first protrusion 711 or the second protrusion 721 may move in the y-axis direction in a region overlapping the second concave portion 723 or the first concave portion 713.

In addition, as the conductive elastic layer 740 is elastically deformed, the distance between the first metal layer 710 and the second metal layer 720 may be decreased. That is, the first height h1 and the second height h2 may be decreased compared to before the elastic deformation (FIGS. 25 and 26). Accordingly, a distance between the first and second metal layers 710 and 720 may be closer, and a resistance value between the first and second metal layers 710 and 720 may decrease.

Figure 31:
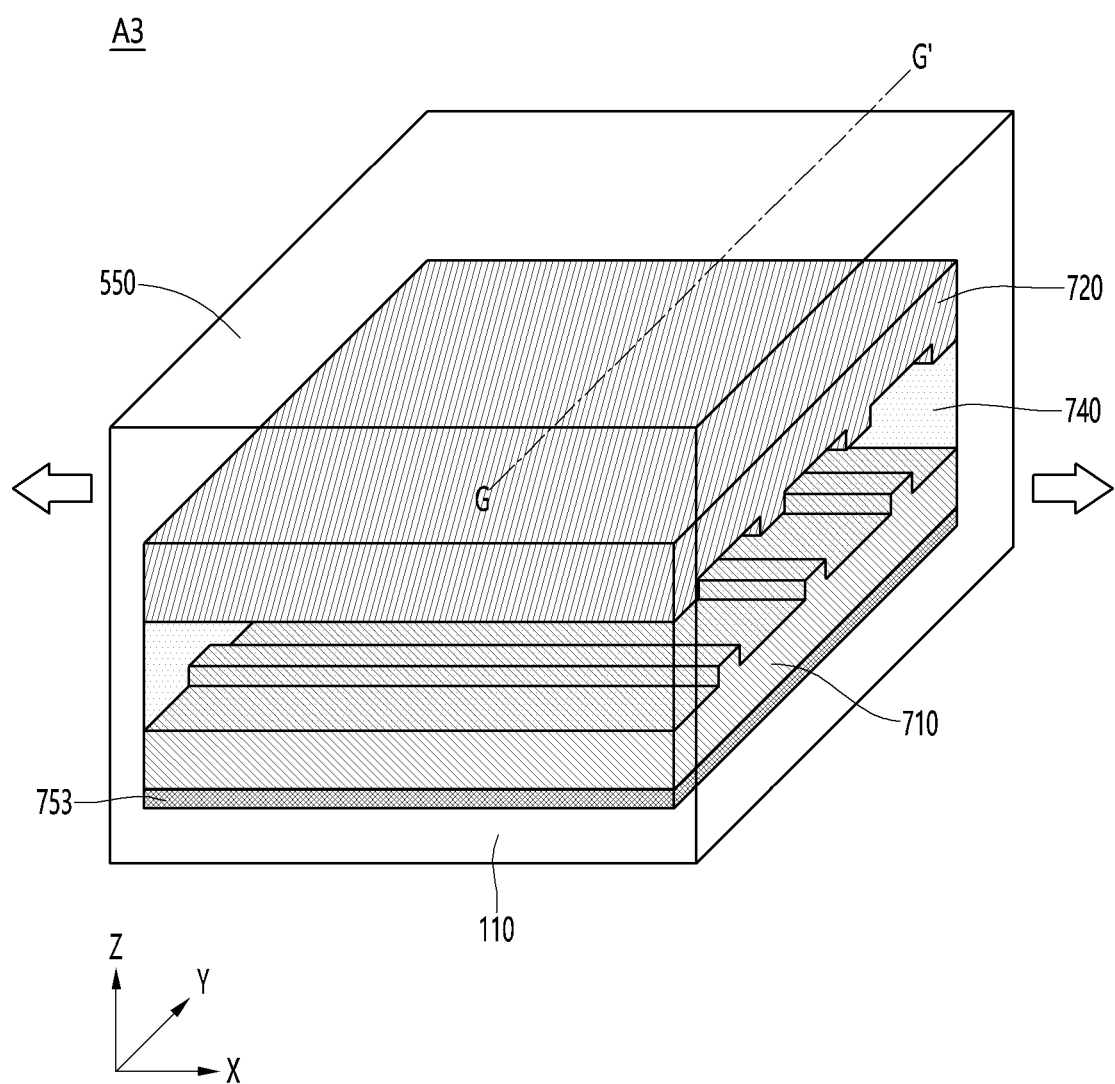
FIG. 31 is another enlarged view of the mask according to the fourth embodiment in which the region A3 in FIG. 24 is enlarged.
Figure 32:
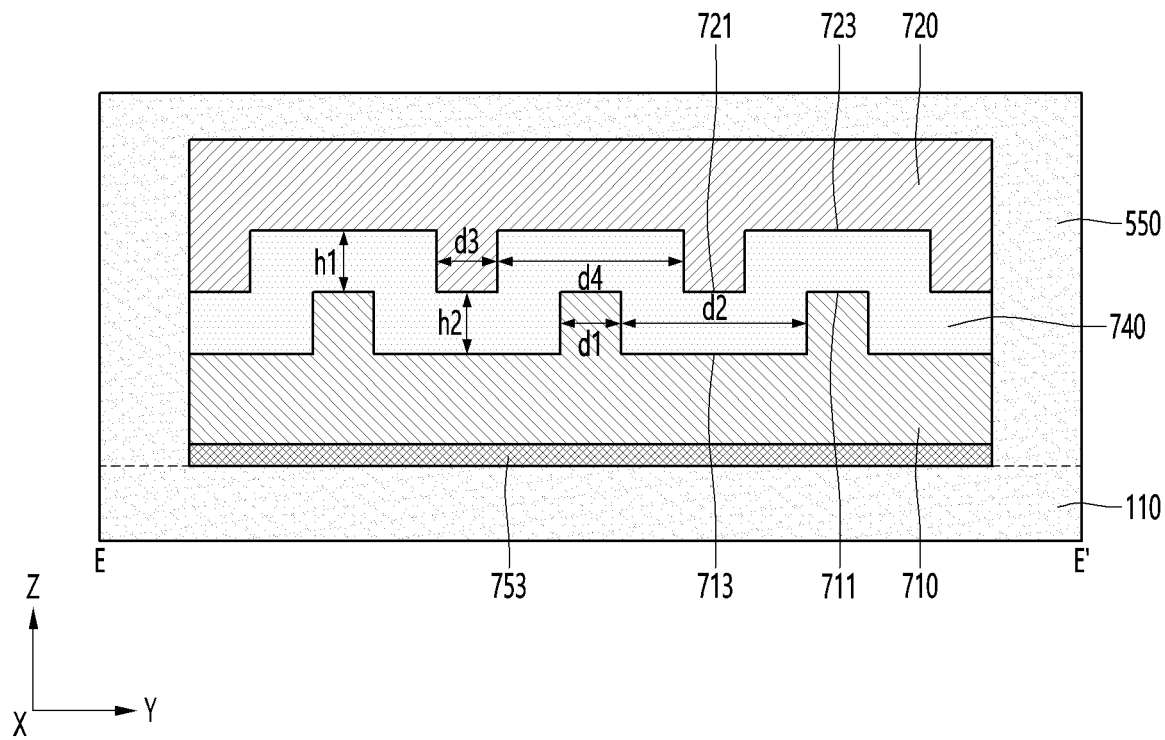
FIG. 32 is a cross-sectional view taken along line G-G' of FIG. 31.

Referring to FIGS. 31 and 32, a third barrier member 753 may be disposed on the first wiring 200. In detail, the third barrier member 753 may be disposed on the outer surface of the first metal layer 710. As an example, the third barrier member 753 may be disposed on a lower surface of the first metal layer 710. That is, the third barrier member 753 may be disposed between the first base layer 110 and the first metal layer 710.

The third barrier member 753 may have a shape corresponding to the lower surface of the first metal layer 710. In addition, the third barrier member 753 may have a size corresponding to the lower surface of the first metal layer 710. In detail, the third barrier member 753 may have the same length in the horizontal direction (x-axis and y-axis directions) as the lower surface of the first metal layer 710 and may have the same plane area.

As shown in the drawings, the third barrier member 753 may be in direct contact with the lower surface of the first metal layer 710. In addition, although not shown in the drawings, the third barrier member 753 may be spaced apart from the lower surface of the first metal layer 710 at a predetermined interval. In this case, the protective layer 550 may be disposed between the third barrier member 753 and the first metal layer 710.

The third barrier member 753 may include a material having an elastic modulus lower than that of the conductive elastic layer 740. The third barrier member 753 may include a material having an elastic modulus lower than that of at least one component selected from among the first base layer 110, the second base layer 120, and the protective layer 550. As an example, the third barrier member 753 may include a metal or polymer material. In detail, the third barrier member 753 may include at least one of polypropylene (PP), polyethylene (PE), polycarbonate (PC), polyimide (polyimide), polyethylene terephthalate polyethylene terephthalate (PET)), and polyetherether ketone (PEEK).

The third barrier member 753 may have about 80% or less of the elastic modulus of the first base layer 110, the second base layer 120, and the protective layer 550. In detail, the elastic modulus of the third barrier member 753 may be about 70% or less of the elastic modulus of the components 110, 120, and 550. Accordingly, the third barrier member 753 may minimize movement of the first metal layer 710 when the conductive elastic layer 740 is elastically deformed, and may induce the deformation of the conductive elastic layer 740 and movement of the second metal layer 720. Therefore, it is possible to prevent the first metal layer 710 and the second metal layer 720 from being damaged.

As described above, the first wiring 200 has been described with reference to FIGS. 24 to 31, but it is preferable that the second wiring 300 has the same shape as the first wiring 200 in consideration of stretchable characteristic of the mask 1000 according to the fourth embodiment.

That is, the mask 1000 according to the fourth embodiment may be elastically deformed so as to correspond to a face shape of the user when the user wears the mask. For example, the mask 1000 may be elastically deformed by the user to effectively adhere to the user's skin.

In this case, the wiring of the mask 1000 may be deformed to correspond to the elastic deformation of the mask 1000, and a wiring corresponding to the curved region such as the nose may be effectively elastically deformed to have improved reliability. In addition, the mask 1000 according to the embodiment is provided so as to elastically deform not only the base layer but also an internal wiring, so that it is possible to have improved reliability in a process in which the user repeatedly wears the mask 1000.

In addition, as the conductive elastic layer 740 is deformed, a distance between the first metal layer 710 and the second metal layer 720 may become closer. Accordingly, a resistance value between the first metal layer 710 and the second metal layer 720 may decrease. Therefore, when the user operates the mask 1000 after wearing the mask, the wirings 200 and 300 may have improved electrical characteristics.

In addition, the mask 1000 according to the fourth embodiment may sense a change in resistance value inside the first wiring 200 to determine elastic deformation information of the mask 1000, and it is possible to provide the information to the user through an indicator 910 to be described later. Accordingly, when a stress exceeding the set range is applied to the mask 1000 or elastically deformed beyond the set range, it is possible to provide a warning sound or the like to the user.

Hereinafter, a method of manufacturing a mask according to an embodiment will be described with reference to FIGS. 33 to 37.

Figure 33:
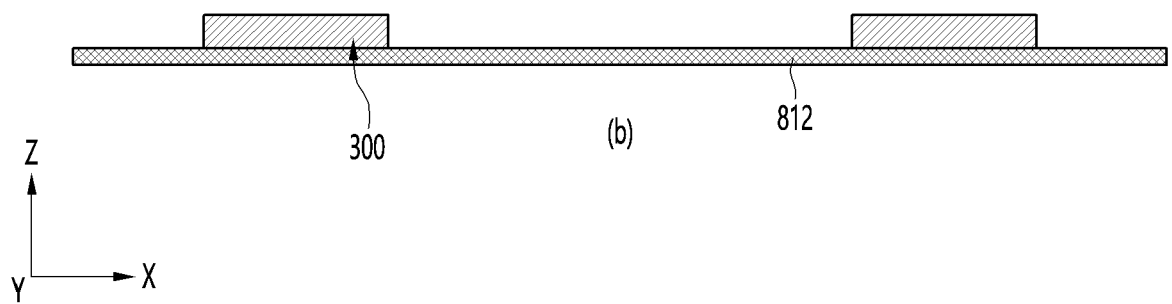

Referring to FIG. 33, the method of manufacturing the mask according to the embodiment may include forming a wiring on a protective film (S301).

The protective film may include a resin material. For example, the protective film may include a resin material such as polyethylene terephthalate (PET), polyethylene naphthalate (PEN), polyimide (PI), and the like, and may be provided in a form of a film having a predetermined thickness. In addition, the wiring may include a conductive material. As an example, the wiring may include at least one metal of aluminum (Al), copper (Cu), silver (Ag), gold (Au), chromium (Cr), nickel (Ni), molybdenum (Mo), titanium (Ti), and alloys thereof. In addition, the wiring may include a non-metal such as carbon, and the like, and may include a conductive elastic body.

The forming of the wiring (S301) may include forming the first wiring 200 on the protective film and forming the second wiring 300 on the protective film. In detail, in step S301, the first wiring 200 may be disposed on a first protective film 811, and the second wiring 300 may be disposed on a second protective film 812 different from the first protective film 811.

Figure 34:
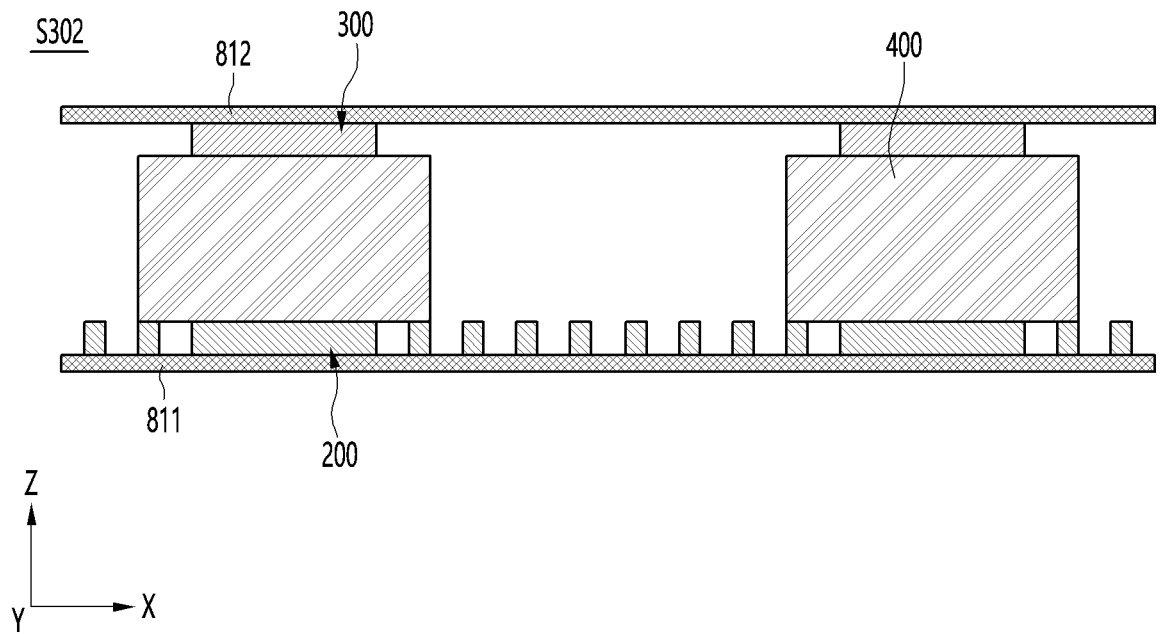

Referring to FIG. 34, the method of manufacturing the mask according to the embodiment may include disposing the piezoelectric element (S302).

The piezoelectric element 400 may include a ceramic material. For example, the piezoelectric element 400 may include at least one of ZnO, AN, LiNbO$_4$, lead antimony stannate, lead magnesium tantalate, lead nickel tantalate, titanates, tungstates, zirconates, or lead including lead zirconate titanate [Pb(Zr$_x$Ti$_{1-x}$)O$_3$(PZT)], lead lanthanum zirconate titanate (PLZT), lead niobium Zirconate titanate (PNZT), BaTiO$_3$, SrTiO$_3$, lead magnesium niobate, lead nickel niobate, lead manganese niobate, lead zinc niobate, lead including lead titanate, barium, bismuth, or niobates of strontium.

The disposing of the piezoelectric element (S302) may be disposing the piezoelectric element 400 between the first protective film 811 and the second protective film 812. The step S302 may be disposing the piezoelectric element 400 between the first wiring 200 and the second wiring 300.

The disposing of the piezoelectric element (S302) may be disposing the piezoelectric element 400 on the first wiring 200 and the second wiring 300. In the step S302, the piezoelectric element 400 may be electrically connected to the first wiring 200 and the second wiring 300.

As an example, a bonding member may be disposed between the first wiring 200 and the lower surface of the piezoelectric element 400 and between the second wiring 300 and the upper surface of the piezoelectric element 400, and the piezoelectric element 400 may be bonded to the first wiring 200 and the second wiring 300 by the bonding member. In detail, in step S302, the first bonding layer 451 may be disposed between the first wiring 200 and the lower surface of the piezoelectric element 400. The first wiring 200 and the lower surface of the piezoelectric element 400 may be bonded by the first bonding layer 451. In addition, the second bonding layer 452 may be disposed between the second wiring 300 and the upper surface of the piezoelectric element 400. The second wiring 300 and the upper surface of the piezoelectric element 400 may be bonded by the second bonding layer 452. The piezoelectric element 400 may be physically and electrically connected to the wirings 200 and 300 by the first and second bonding layers 451 and 452.

Figure 35:
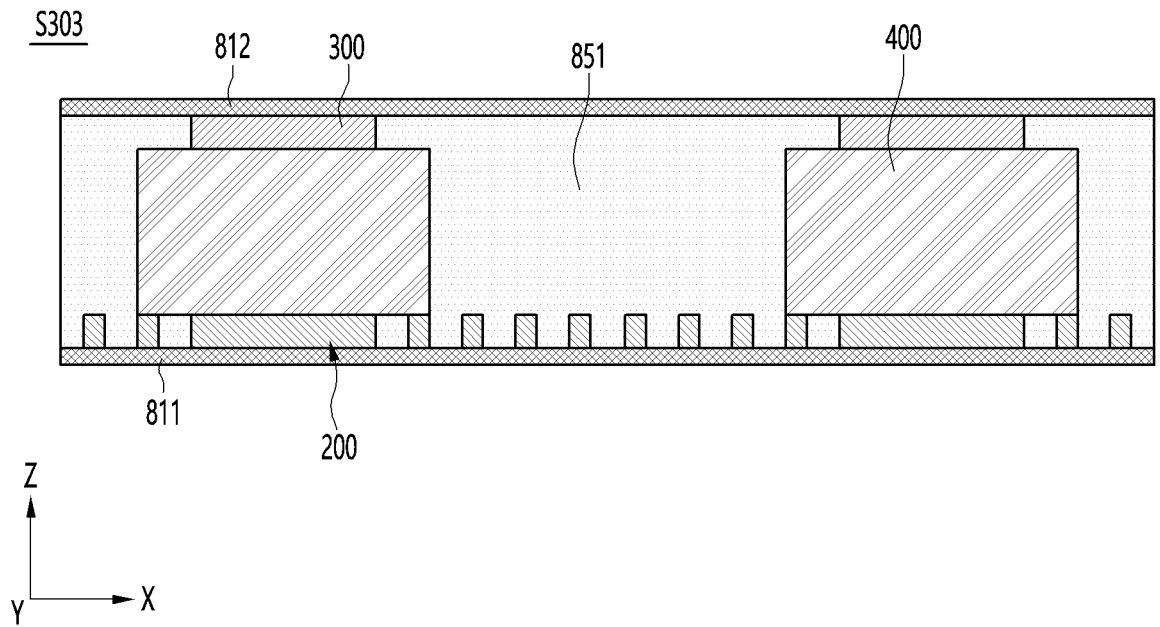

Referring to FIG. 35, the method of manufacturing the mask according to the embodiment may include sealing the piezoelectric element (S303).

The sealing of the piezoelectric element (S303) may be forming a fourth filling layer 851 between the first protective film 811 and the second protective film 812 using a filler.

The fourth filling layer 851 may include a material having softness and elasticity. For example, the fourth filling layer 851 may include at least one material of silicone, a thermoplastic resin, a thermoplastic silicone resin, a thermoplastic elastomer, a polyurethane elastomer, an ethylene vinyl acetate (EVA), a polyvinyl chloride (PVC) in which a harmless plasticizer and a stabilizer are added. The fourth filling layer 851 may be preferable to include a silicone elastomer that is relatively light, may minimize irritation upon contact with the user's skin, and has a predetermined elasticity.

In the sealing of the piezoelectric element (S303), the filler may be supplied between the first protective film 811 and the second protective film 812. Thereafter, the filler may be cured to form the fourth filler layer 851.

The fourth filling layer 851 may be disposed to surround the piezoelectric element 400. The fourth filling layer 851 may be in direct contact with the piezoelectric element 400. The fourth filling layer 851 may be formed to be thicker than the piezoelectric element 400 and may be disposed to surround the entire piezoelectric element 400. In addition, the fourth filling layer 851 may be disposed to surround the first and second wirings 200 and 300 disposed on the first and second protective films 811 and 812. The fourth filling layer 851 may be in direct contact with the first and second wirings 200 and 300. In addition, the fourth filling layer 851 may be in direct contact with the first bonding layer 451 and the second bonding layer 452.

Figure 36:
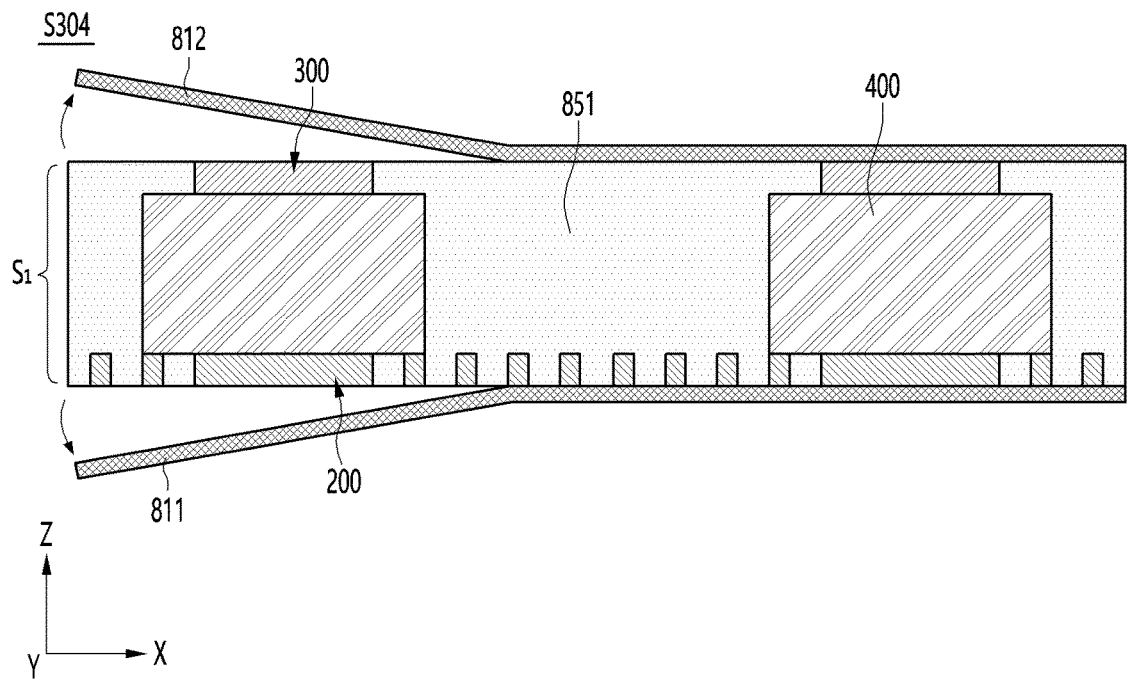

Referring to FIG. 36, the method of manufacturing the mask according to the embodiment may include removing the protective film (S304).

The removing of the protective film (S304) may be removing the first protective film 811 and the second protective film 812 and forming a structure defined as a first structure 51.

In the step S304, the first protective film 811 disposed on a lower surface of the fourth filling layer 851 may be removed. In addition, in the step S304, the second protective film 812 disposed on an upper surface of the fourth filling layer 851 may be removed. In the step S304, the first and second protective films 811 and 812 may be removed by a mechanical or chemical method, but the embodiment is not limited thereto.

After the removing of the protective film (S304), the lower and upper surfaces of the fourth filling layer 851 may be exposed. In detail, the lower surface of the first wiring 200 facing the upper surface of the first protective film 811 may be exposed. In this case, the lower surface of the fourth filling layer 851 may be disposed on the same plane as the lower surface of the first wiring 200. In addition, a lower surface of the second wiring 300 facing the upper surface of the second protective film 812 may be exposed. In this case, the upper surface of the fourth filling layer 851 may be disposed on the same plane as the lower surface of the second wiring 300.

The first structure 51 including the piezoelectric element 400, the first wiring 200, the second wiring 300, and the fourth filling layer 851 may be formed through the step S304.

Figure 37:
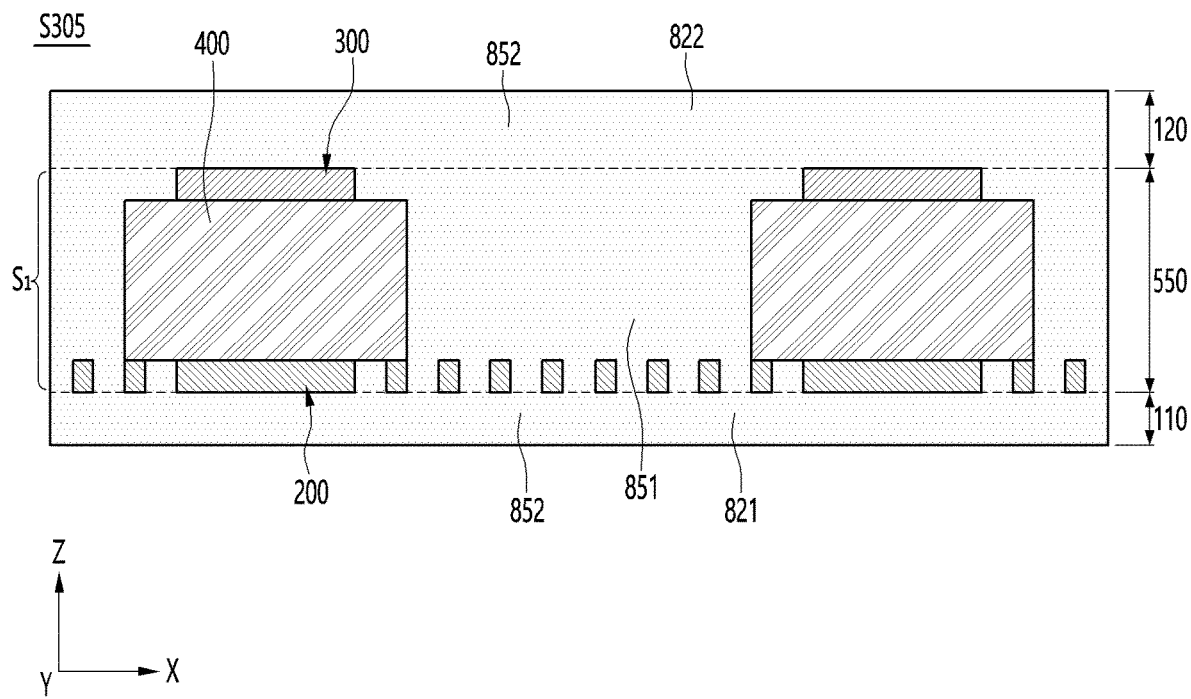

Referring to FIG. 37, the method of manufacturing the mask according to the embodiment may include forming a filling layer on the first structure (S305).

The forming of the filling layer (S305) may be forming a fifth filling layer 852 on the first structure 51 by disposing the filler on the first structure 51.

The fifth filling layer 852 may include at least one material of silicone, a thermoplastic resin, a thermoplastic silicone resin, a thermoplastic elastomer, a polyurethane elastomer, an ethylene vinyl acetate (EVA), a polyvinyl chloride (PVC) in which a harmless plasticizer and a stabilizer are added. The fifth filling layer 852 may be preferable to include a silicone elastomer that is relatively light, may minimize irritation upon contact with the user's skin, and has a predetermined elasticity.

In the step S305, the filler may be supplied around the first structure S1. As an example, in step S305, the first structure 51 may be disposed in a molding jig having an accommodating portion having a set shape and size. Thereafter, the filler may be supplied into the molding jig, and the filler may be disposed to surround the first structure 51. Thereafter, the filler may be cured to become the fifth filling layer 852. In this case, the fifth filling layer 852 may include the same material as the fourth filling layer 851. Since the fifth filling layer 852 includes the same material as the fourth filling layer 851, it is possible to have improved bonding force.

The fifth filling layer 852 may be disposed to surround upper and lower surfaces of the first structure 51. In addition, although not shown in the drawings, the fifth filling layer 852 may be disposed to surround at least one side surface of the first structure 51. For example, the fifth filling layer 852 may be disposed to surround the entire side surface of the first structure 51.

That is, the fifth filling layer 852 may be in direct contact with the upper and lower surfaces of the fourth filling layer 851. In addition, the fifth filling layer 852 may be in direct contact with a side surface of the fourth filling layer 851. In addition, the fifth filling layer 852 may be in direct contact with the first wiring 200 and the second wiring 300. The fifth filling layer 852 may be disposed to selectively surround the outer surface of the first structure S1 according to a shape and/or size of the molding jig, but the embodiment is not limited thereto.

The mask 1000 according to the embodiment including the first base layer 110, the second base layer 120, the piezoelectric element 400, the first wiring 200, the second wiring 300, and the protective layer 550 may be manufactured through the forming of the filling layer on the first structure (S305).

Therefore, the method of manufacturing the mask according to the embodiment may prevent or minimize deformation of a layer that occurs during a manufacturing process, and may improve alignment characteristics between the piezoelectric element 400 and the wirings 200 and 300.

In detail, in a method of manufacturing the conventional mask, filling layers 821 and 822 surrounding the wirings 200 and 300 were formed on the protective films 811 and 812, the protective films 811 and 812 were removed, and then the piezoelectric element and the wirings 200 and 300 were connected.

However, in the method of manufacturing of the mask according to the embodiment, the wirings 200 and 300 and the piezoelectric element 400 may be connected before forming a separate filling layer surrounding the wirings 200 and 300 on the protective films 811 and 812.

That is, in the embodiment, when the wirings 200 and 300 and the piezoelectric element 400 are connected, the separate filling layer is not disposed on the protective films 811 and 812, and thus it is possible to prevent or reduce the occurrence of an alignment failure between the piezoelectric element 400 and the wirings 200 and 300 by the ductility of the filling layer. As an example, a maximum degree at which the wirings 200 and 300 and the piezoelectric element 400 are misaligned may be about 1 mm or less based on a horizontal direction in a process of manufacturing the mask 1000. In detail, the degree of misalignment may be about 500 μm or less. Preferably, the degree of misalignment may be about 300 μm or less. That is, the embodiment may have more improved alignment characteristics compared with a conventional manufacturing method that is disposed to be misaligned up to 1.7 mm or more, and the piezoelectric element 400 may have improved reliability with the wirings 200 and 300.

In addition, in the related art, when the filling layers 821 and 822 surrounding the wirings 200 and 300 are colored, there is a problem that it is very difficult to align the wirings 200 and 300 with the piezoelectric element 400.

However, in the embodiment, the wirings 200 and 300 and the piezoelectric element 400 may be first connected before the separate filling layer is disposed, and thereafter, the fourth filling layer 851 surrounding the piezoelectric element 400 may be disposed. Accordingly, the fourth filling layer 851 surrounding the piezoelectric element 400 may be provided in various colors regardless of color.

In addition, in the related art, a pressurization process of applying a predetermined pressure for coupling between the piezoelectric element 400 and the wirings 200 and 300 was performed in disposing the piezoelectric element.

However, in the embodiment, a separate pressurization process may be omitted, and the mask 1000 may be manufactured by disposing the first structure in the molding jig and forming the fifth filling layer 852. Accordingly, the thickness of the first base layer 110 and the second base layer 120 of the mask 1000 to be manufactured, for example, a thickness of the reflective layer and the matching layer may be manufactured to a set thickness. Accordingly, the mask 1000 according to the embodiment may have uniform ultrasonic reflection characteristics and impedance characteristics.

Hereinafter, another beauty mark according to embodiments will be described with reference to FIGS. 38 and 39.

Figure 38:
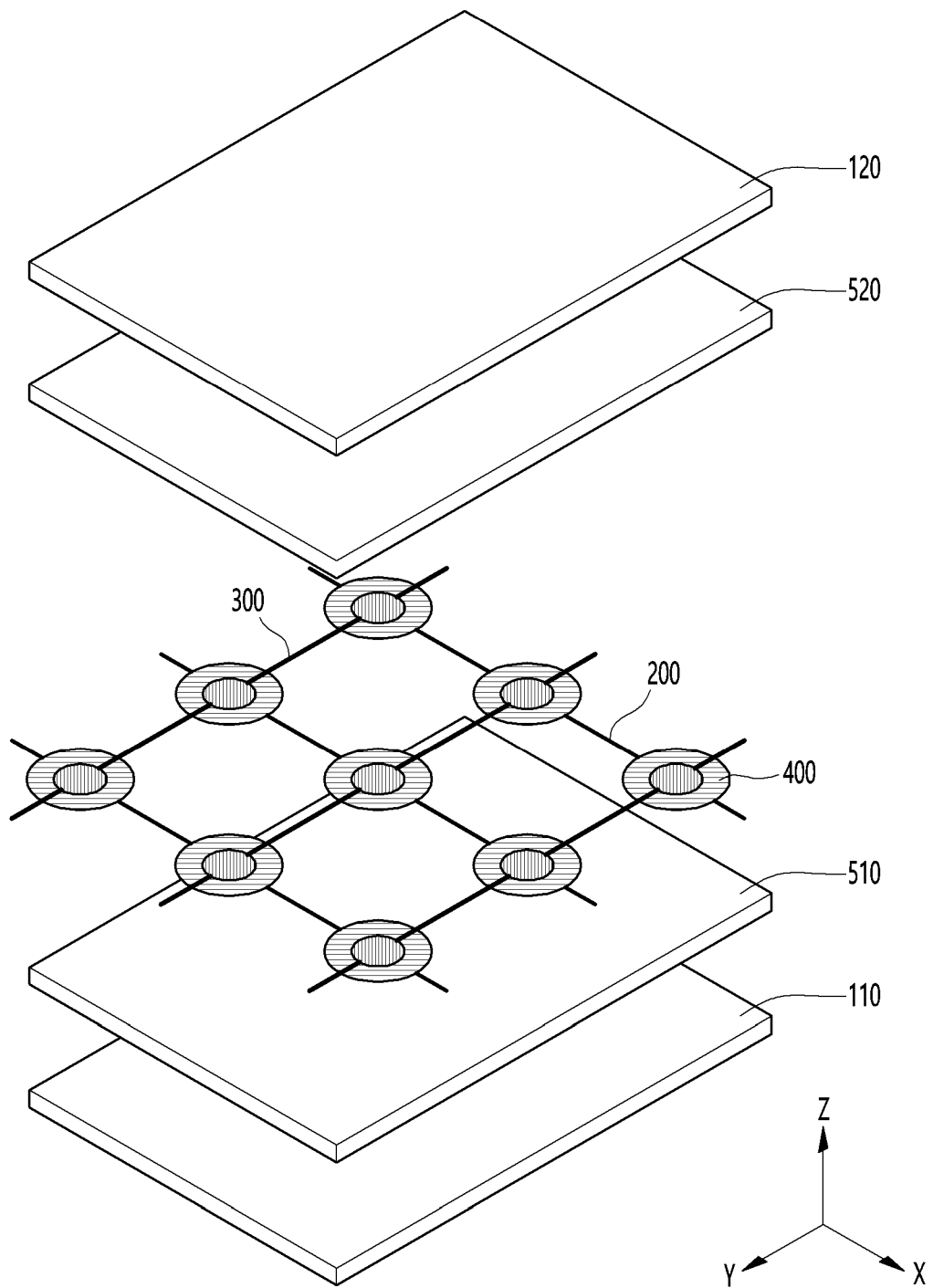
FIG. 38 is another exploded perspective view of the region A1 in FIG. 1.
Figure 39:
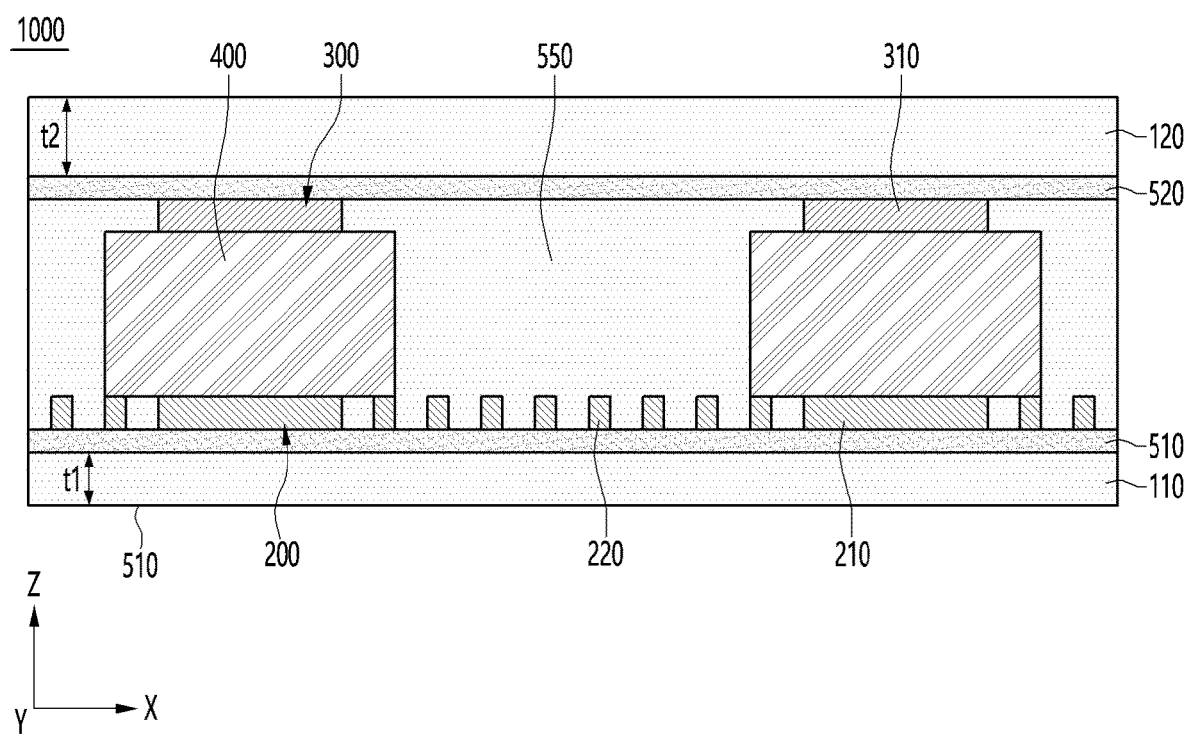
FIG. 39 is a cross-sectional view illustrating a cross section of the mask of FIG. 38.

Referring to FIGS. 38 and 39, the mask 1000 according to the embodiment may further include a first substrate 510 and a second substrate 520.

The first substrate 510 may be disposed on the first base layer 110. The first substrate 510 may be disposed between the first base layer 110 and the first wiring 200. The first substrate 510 may be in direct contact with one surface of the first base layer 110. In this case, the first wiring 200 may be spaced apart from the first base layer 110 and may be in direct contact with the first substrate 510.

The first substrate 510 may be transparent and include a material in consideration of moisture barrier properties, thermal stability, and the like. In addition, the first substrate 510 may include a material that has flexibility and is elastically deformed depending on a shape of the user's skin. As an example, the first substrate 510 may include a resin material such as polyethylene terephthalate (PET), polyethylene naphthalate (PEN), polyimide (PI), and the like. The first substrate 510 may be provided in a form of a film.

The first substrate 510 may have a thickness of about 0.5 μm to about 5 μm or less. When the thickness of the first substrate 510 is less than about 0.5 μm, there may be a problem that a region of the first substrate 510 that overlaps the components is sagged by a weight of components disposed on the first substrate 510, for example, the piezoelectric element 400 or the like. Accordingly, reliability of the first substrate 510 may be deteriorated, and a problem of alignment of the components disposed on the first substrate 510 may occur. In addition, when the thickness of the first substrate 510 exceeds about 5 μm, the overall thickness of the mask 1000 may be increased. Accordingly, there is a problem that the mask 1000 may not be elastically deformed efficiently depending on the shape of the user's skin, so that the mask 1000 may not be effectively adhered to the user's skin. Preferably, the first substrate 510 may have a thickness of about 0.5 μm to about 3 μm. When the thickness of the first substrate 510 satisfies the above-described range, the mask 1000 may be elastically deformed efficiently in a form corresponding to the user's skin, and the overall thickness and weight of the mask 1000 may be decreased while maintaining reliability and alignment characteristics.

The second substrate 520 may be disposed on the second base layer 120. The second substrate 520 may be disposed between the second base layer 120 and the second wiring 300. The second substrate 520 may be in direct contact with one surface of the second base layer 120. In this case, the second wiring 300 may be spaced apart from the second base layer 120 and may be in direct contact with the second substrate 520.

The second substrate 520 may be transparent and include a material in consideration of moisture barrier properties, thermal stability, and the like. In addition, the second substrate 520 may include a material that has flexibility and is elastically deformed depending on the shape of the user's skin. As an example, the second substrate 520 may include the resin material such as polyethylene terephthalate (PET), polyethylene naphthalate (PEN), polyimide (PI), and the like. The second substrate 520 may be provided in a form of a film. The second substrate 520 may have the same material and shape as the first substrate 510, but the embodiment is not limited thereto.

The second substrate 520 may have a thickness of about 0.5 μm to about 5 μm or less. When the thickness of the second substrate 520 is less than about 0.5 μm, there may be a problem that a region of the second substrate 520 that overlaps the components is sagged by a weight of components disposed on the second substrate 520, for example, the piezoelectric element 400 or the like. Accordingly, reliability of the second substrate 520 may be deteriorated, and a problem of alignment of the components disposed on the second substrate 520 may occur. In addition, when the thickness of the second substrate 520 exceeds about 5 μm, the overall thickness of the mask 1000 may be increased. Accordingly, there is a problem that the mask 1000 may not be elastically deformed efficiently depending on the shape of the user's skin, so that the mask 1000 may not be effectively adhered to the user's skin. Preferably, the second substrate 520 may have a thickness of about 0.5 μm to about 3 μm. When the thickness of the second substrate 520 satisfies the above-described range, the mask 1000 may be elastically deformed efficiently in a form corresponding to the user's skin, and the overall thickness and weight of the mask 1000 may be decreased while maintaining reliability and alignment characteristics. The second substrate 520 may have the same thickness as the first substrate 510, but the embodiment is not limited thereto.

In the embodiment, as the first substrate 510 and the second substrate 520 are added, the alignment characteristics of the piezoelectric element 400 may be improved. In addition, as the first substrate 510 and the second substrate 520 are added, an inflow path of moisture and foreign substances introduced from the outside to the inside may be increased, so that the mask 1000 may have improved reliability.

Figure 40:
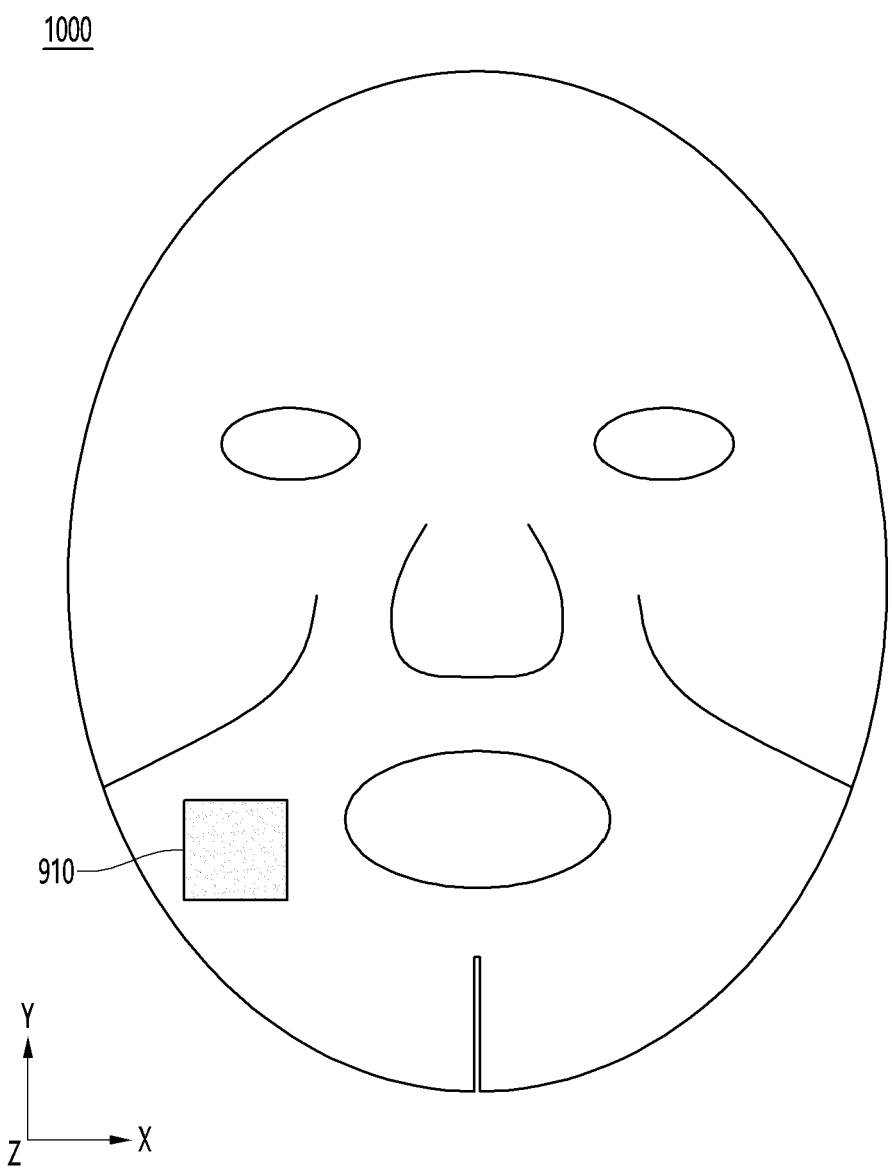
FIGS. 40 to 42 are views illustrating examples in which an indicator and a protrusion are provided to a mask according to an embodiment.
Figure 41:
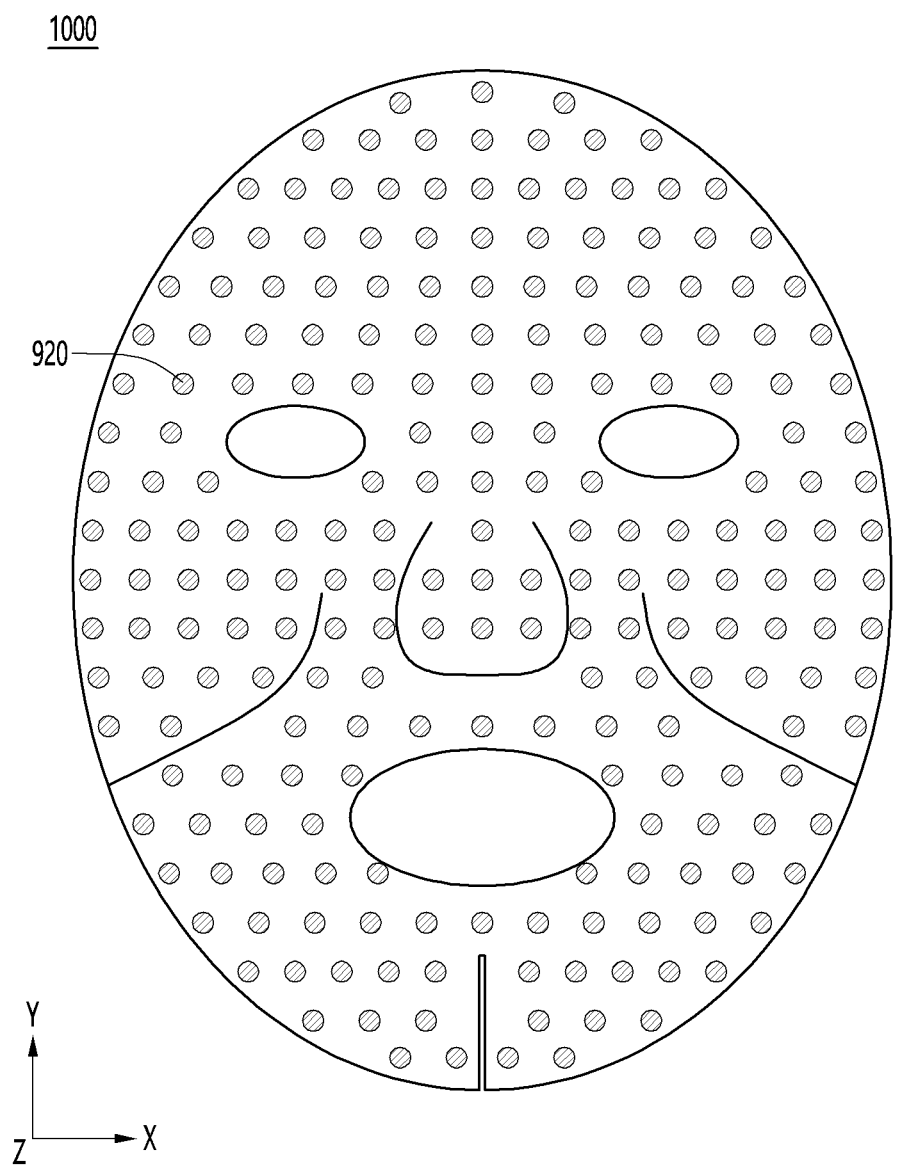
Figure 42:
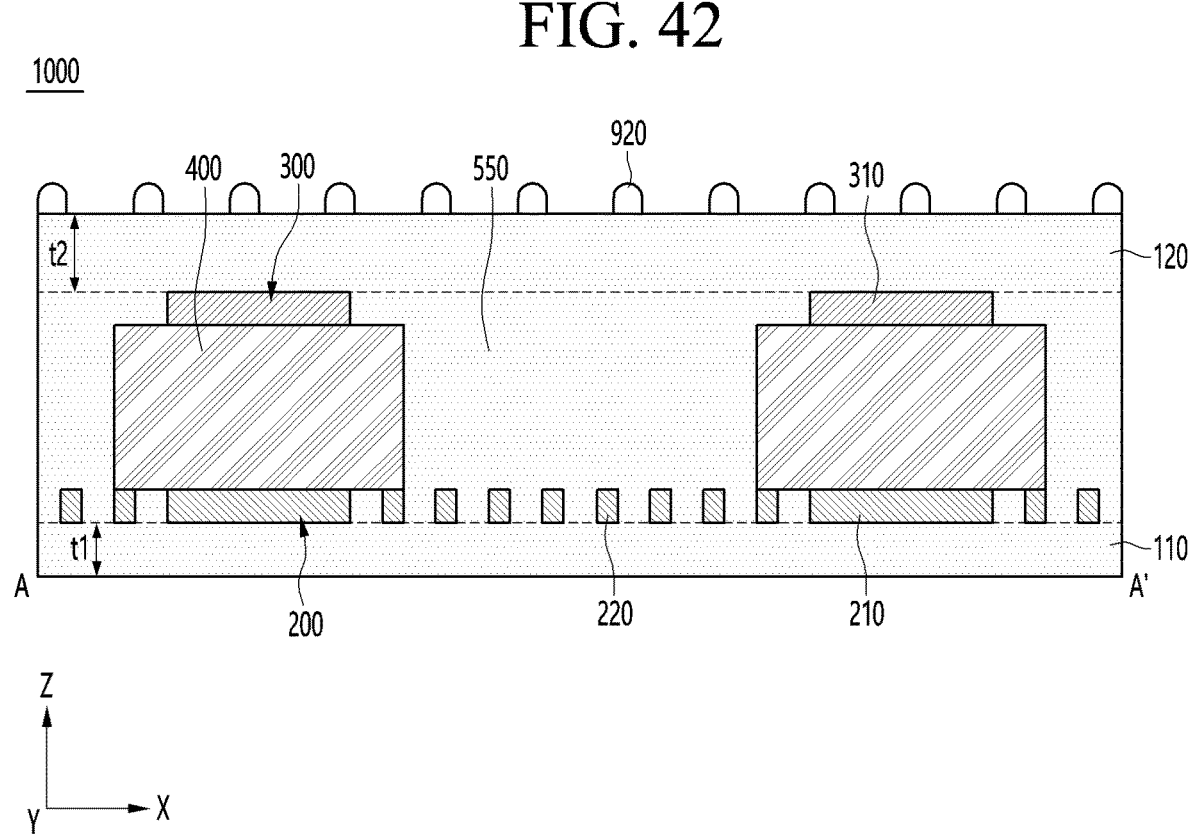

FIGS. 40 to 42 are views illustrating an example in which an indicator and a protrusion are provided on the mask according to the embodiment.

Referring to FIG. 40, the mask 1000 may include an indicator 910. The indicator 910 may include at least one of members such as an LED, a display, a buzzer, and the like that may transmit visual or auditory information to a user.

The indicator 910 may be disposed outside the mask 1000 to display an operation state of the mask 1000. As an example, the indicator 910 may provide information about the start of the operation of the mask 1000, information notifying that the operation is in progress, and information about the completion of the operation through the auditory information generated from the buzzer. In addition, the indicator 910 may display the operation state according to the light emission color of the LED. In addition, the indicator may display information on an operating frequency domain through the display.

In addition, referring to FIGS. 41 and 42, the mask 1000 may include a protrusion 920 disposed on an outer surface thereof. In detail, the protrusion 920 may be disposed on a surface of the second base layer 120 facing the user's skin. For example, the protrusion 920 may be disposed on the other surface opposite to one surface of the second base layer 120 on which the second wiring 300 is disposed.

The protrusion 920 may include a material harmless to the human body and may be disposed to protrude from the other surface of the second base layer 120 toward the user's skin. The protrusions 920 may be disposed in a form of a plurality of points spaced apart from each other on the other surface of the second base layer 120. In addition, the protrusions 920 may be disposed in a form of a plurality of straight lines or curves spaced apart from each other on the other surface of the second base layer 120. In addition, the protrusions 920 may be disposed in at least one line shape on the other surface of the second base layer 120. As an example, the protrusions 920 may be disposed in at least one spiral shape on the other surface of the second base layer 120.

When the user wears the mask 1000, the protrusion 920 may form a predetermined space between the mask 1000 and the user's skin. Accordingly, it is possible to prevent cosmetics or drugs between the mask 1000 and the skin from being pushed out to an edge region of the mask 1000 by the pressure generated when the mask 1000 are worn and/or the ultrasonic energy generated from the piezoelectric element 400. That is, the protrusion 920 may serve as a partition wall preventing cosmetics or drugs from getting out of the mask 1000. Therefore, the user may effectively inject cosmetics or drugs into the skin using the mask 1000.

Figure 43:
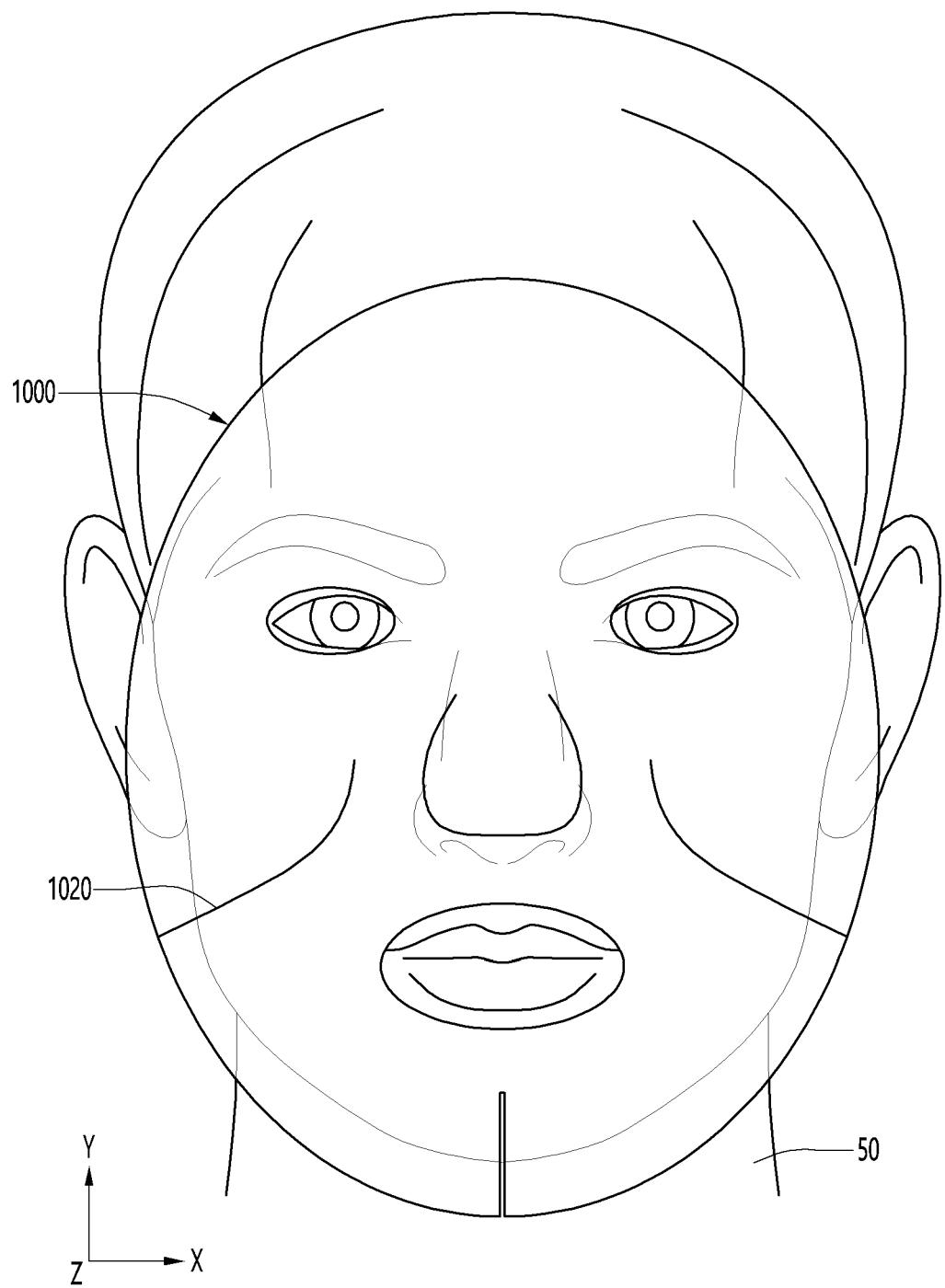
FIG. 43 is a view illustrating a user wearing the mask according to the embodiment.
Figure 44:
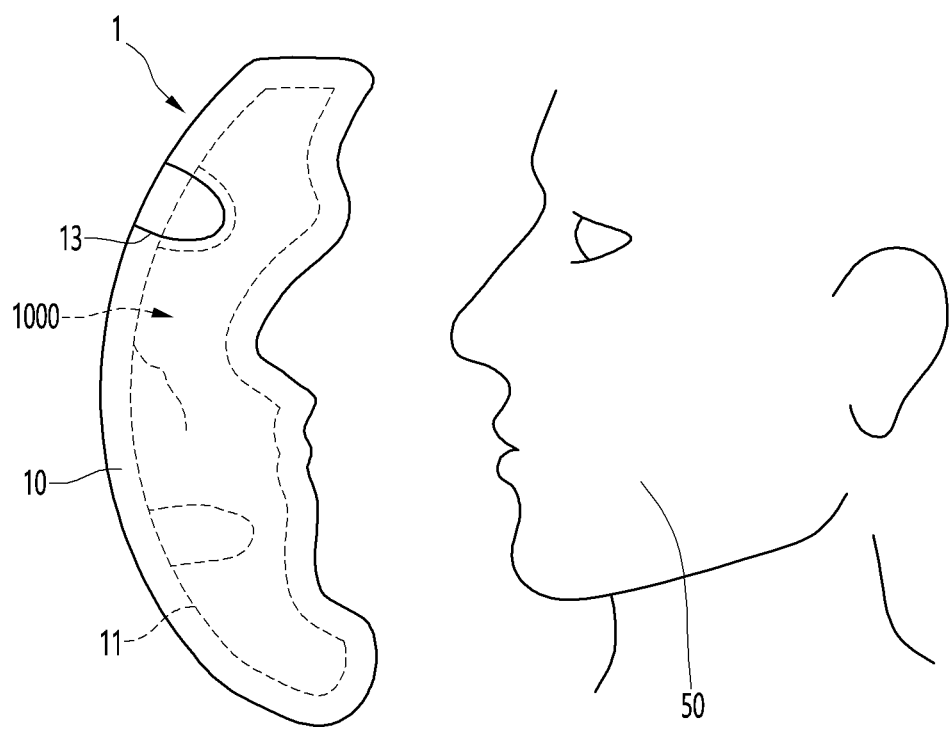
FIG. 44 is a view illustrating a skin care device to which the mask according to the embodiment is applied.

FIG. 43 is a view illustrating a user wearing the mask according to the embodiment, and FIG. 44 is a view illustrating a skin care device to which the mask according to the embodiment is applied.

Referring to FIG. 43, a user 50 may wear the mask 1000. The mask 1000 may include the above-described opening 1010, and the user 50 may secure a view through the opening 1010. In addition, the mask 1000 may include the above-described cutout portion 1020, and the mask 1000 may be effectively close-adhered to the curved skin by the cutout portion 1020. In this case, one surface of the second base layer 120 may be in direct contact with skin of the user 50. In addition, drugs or cosmetics may be disposed between the second bath layer 520 and the skin of the user 50, so that the base layer 520 may be in direct or indirect contact with the skin of the user 50.

The mask 1000 may be operated by receiving power through an external power connected to the mask 1000. In addition, the mask 1000 may be operated by receiving power through a power supply unit 1100 disposed outside the mask 1000, for example, on the other surface of the first base layer 110.

In addition, referring to FIG. 44, the mask 1000 may be applied to a skin care device 1 to operate.

In detail, referring to FIG. 44, the skin care device 1 may include a main body 10 in which one side thereof is open and including an accommodation space 11 therein.

The main body 10 may include a material that may be light and prevent damage from external impact or contact. As an example, the main body 10 may include a plastic or ceramic material, may have improved reliability from an external environment, and may protect the mask 1000 disposed inside the accommodation space 11. In addition, the main body 10 may include a viewing part 13 formed at a position corresponding to the user's eyes. The viewing part 13 is formed in a region corresponding to the opening 1010 of the mask 1000, and the user may secure an external view through the viewing part 13.

The mask 1000 may be disposed in the accommodation space 11 of the main body 10. The mask 1000 may be disposed between the main body 10 and the skin of the user 50. In detail, the first base layer 110 of the mask 1000 may be disposed to face the accommodation space 11 of the main body 10, and the second base layer 120 of the mask 1000 may be disposed to face the skin of the user 50.

The mask 1000 may be coupled to the main body 10. For example, the mask 1000 may be fixed to a set position in the accommodation space 11 by a fastening member (not shown) and may have a structure that is detachable from the main body 10.

The mask 1000 may be supplied with power through the power supply unit 1100 disposed outside the mask 1000, for example, on the other surface of the first base layer 110. Alternatively, the mask 1000 may be connected to the main body 10 to be supplied with power through the power supply unit 1100 disposed on the main body 10.

The mask 1000 may include a deformable member (not shown) disposed on the lower surface of the first base layer 110. The deformable member may be in direct contact with the first base layer 110 and may be disposed facing the accommodation space 11 of the main body 10. That is, the deformable member may be disposed between the main body 10 and the first base layer 110 of the mask 1000.

The deformable member may include a material of which shape is changed by external pressure. For example, the deformable member may include a material such as an air gap or a sponge, but the embodiment is not limited thereto, and may include various materials of which shape is changed by external pressure. Accordingly, when the user 50 puts on the skin care device 1, the deformable member may be deformed into a shape corresponding to the shape of the face of the user 50. Therefore, the ultrasonic mask 1000 and the skin of the user 50 may be effectively close-adhered to each other. In addition, when a plurality of users put on the skin care device 1, the deformable member is deformed to correspond to each face shape, so that the skin of the user 50 and the mask 1000 may be effectively close-adhered to each other.

The characteristics, structures, effects, and the like described in the above-described embodiments are included in at least one embodiment of the present invention, but are not limited to only one embodiment. Furthermore, the characteristic, structure, and effect illustrated in each embodiment may be combined or modified for other embodiments by a person skilled in the art. Therefore, it should be construed that the contents related to such combination and modification are included in the scope of the present invention.

In addition, the above description has been focused on the embodiments, but it is merely illustrative and does not limit the present invention. Those skilled in the art to which the embodiments pertain may appreciate that various modifications and applications not illustrated above are possible without departing from the essential features of the embodiment. For example, each component particularly represented in the embodiments may be modified and realized. In addition, it should be construed that differences related to such a modification and an application are included in the scope of the present invention defined in the appended claims.

The invention claimed is:

1. A mask comprising:
a first wiring disposed on a first base layer;
a piezoelectric element disposed on the first wiring;
a second wiring disposed on the piezoelectric element;
a second base layer disposed on the second wiring;
a protective layer disposed between the first and second base layers and surrounding the first wiring, the second wiring, and the piezoelectric element; and
a control unit for controlling a driving frequency of the piezoelectric element,
wherein the control unit controls the driving frequency of the piezoelectric element in a frequency band defined as a first range, and
a temperature of the piezoelectric element is changed by controlling the driving frequency by the control unit,
wherein the frequency band of the first range includes a resonant frequency of the piezoelectric element, and is lower than an anti-resonant frequency of the piezoelectric element, and
wherein a temperature of the piezoelectric element when the driving frequency is the resonant frequency of the piezoelectric element is higher than a temperature of the piezoelectric element when the driving frequency is higher than the resonant frequency of the piezoelectric element and is lower than a temperature of the piezoelectric element when the driving frequency is lower than the resonant frequency of the piezoelectric element.

2. The mask of claim 1, wherein the first range satisfies the following [Equation 1], and a constant k value below is 0.2 to 0.3

$$fo = fr \pm k^*(fa - fr)$$ [Equation 1]

(fo: driving frequency of piezoelectric element, fr: resonant frequency of piezoelectric element, k: constant, fa: anti-resonant frequency of piezoelectric element).

3. The mask of claim 2, wherein the constant k value is 0.22 to 0.27.

4. The mask of claim 1, wherein the control unit sets a first frequency defined as a frequency band higher than the resonant frequency of the piezoelectric element as the driving frequency to reduce the temperature of the piezoelectric element.

5. The mask of claim 1, wherein the control unit sets a second frequency defined as a frequency band lower than the resonant frequency of the piezoelectric element as the driving frequency to increase the temperature of the piezoelectric element.

6. The mask of claim 1, further comprising a sensing unit for sensing a temperature of the mask.

7. The mask of claim 1, further comprising:
a first substrate disposed between the first base layer and the first wiring; and
a second substrate disposed between the second base layer and the second wiring.

8. The mask of claim 1, wherein the first base layer, the second base layer, and the protective layer include the same material.

9. The mask of claim 1, wherein a thickness of the first base layer is equal to or smaller than a thickness of the second base layer.

10. The mask of claim 9, wherein the thickness of the first base layer and the second base layer is 50 μm to 10 mm.

11. The mask of claim 1, wherein at least one of the first wiring and the second wiring includes a curvature pattern of 3R to 20R (mm).

12. The mask of claim 1, wherein the piezoelectric element generates ultrasonic energy of 10 KHz to 1 MHz.

13. A temperature control method of a mask including a plurality of operation modes,
wherein the mask includes:
a control unit for controlling a driving frequency of a piezoelectric element; and
a sensing unit for sensing a temperature of the mask,
the temperature control method comprising:
setting the operation mode;
setting the driving frequency of the piezoelectric element; and
operating at the set driving frequency,
wherein the control unit controls the driving frequency of the piezoelectric element in a frequency band defined as a first range,
a temperature of the piezoelectric element is changed by controlling the driving frequency by the control unit,
wherein the frequency band of the first range includes a resonant frequency of the piezoelectric element, and is lower than an anti-resonant frequency of the piezoelectric element, and
wherein a temperature of the piezoelectric element when the driving frequency is the resonant frequency of the piezoelectric element is higher than a temperature of the piezoelectric element when the driving frequency is higher than the resonant frequency of the piezoelectric element and is lower than a temperature of the piezoelectric element when the driving frequency is lower than the resonant frequency of the piezoelectric element.

14. The method of claim 13, wherein the first range satisfies the following [Equation 1], and a constant k value below is 0.2 to 0.3

$$fo=fr\pm k*(fa-fr) \qquad \text{[Equation 1]}$$

(fo: driving frequency of piezoelectric element, fr: resonant frequency of piezoelectric element, k: constant, fa: anti-resonant frequency of piezoelectric element).

15. The method of claim 14, wherein when a heating mode is set in the setting of the operation mode, the control unit sets a frequency band lower than the resonant frequency of the piezoelectric element as the driving frequency in the setting of the driving frequency.

16. The method of claim 14, wherein when a cooling mode is set in the setting of the operation mode, the control unit sets a frequency band higher than the resonant frequency of the piezoelectric element as the driving frequency in the setting of the driving frequency.

17. The method of claim 15, wherein the operating at the driving frequency includes sensing the temperature of the mask, and when the temperature of the mask is greater than or equal to a set temperature in the sensing of the temperature, the control unit corrects the driving frequency of the piezoelectric element to a frequency band greater than the driving frequency currently in operation.

18. The method of claim 13, wherein the sensing unit senses a surface temperature of the mask in contact with a user's skin.

19. A skin care device comprising:
a main body in which one side thereof is open and including an accommodation space inside the open region; and
a mask disposed in the open region and connected to the main body,
wherein the mask includes a mask according to claim 1.

* * * * *